(12) United States Patent
Oestergaard et al.

(10) Patent No.: US 9,370,583 B2
(45) Date of Patent: Jun. 21, 2016

(54) COAGULATION FACTOR VII POLYPEPTIDES

(71) Applicant: Novo Nordisk HealthCare AG, Zurich (CH)

(72) Inventors: Henrik Oestergaard, Oelstykke (DK); Prafull S. Gandhi, Ballerup (DK); Ole Hvilsted Olsen, Broenshoej (DK); Carsten Behrens, Koebenhavn N (DK); Paul L. DeAngelis, Edmond, OK (US); Friedrich Michael Haller, Norman, OK (US)

(73) Assignee: NOVO NORDISK HEALTHCARE AG, Zurich (CH)

( * ) Notice: Subject to any disclaimer, the term of this patent is extended or adjusted under 35 U.S.C. 154(b) by 0 days.

(21) Appl. No.: 14/936,224

(22) Filed: Nov. 9, 2015

(65) Prior Publication Data
US 2016/0120992 A1 May 5, 2016

Related U.S. Application Data

(63) Continuation of application No. 14/514,794, filed on Oct. 15, 2014.

(60) Provisional application No. 61/895,438, filed on Oct. 25, 2013.

(30) Foreign Application Priority Data

Oct. 15, 2013 (EP) .................... 13188715
Feb. 12, 2014 (EP) .................... 14154875

(51) Int. Cl.
*A61K 38/36* (2006.01)
*C07K 14/745* (2006.01)
*A61P 7/00* (2006.01)
*A61K 47/48* (2006.01)

(52) U.S. Cl.
CPC ........... *A61K 47/4823* (2013.01); *A61K 38/36* (2013.01)

(58) Field of Classification Search
CPC ................... A61K 38/36; A61K 47/4823
See application file for complete search history.

(56) References Cited

U.S. PATENT DOCUMENTS

| | | | |
|---|---|---|---|
| 6,806,063 B2 | 10/2004 | Pedersen et al. | |
| 7,371,543 B2 | 5/2008 | Pedersen et al. | |
| 7,511,024 B2 | 3/2009 | Pedersen et al. | |
| 7,517,974 B2 | 4/2009 | Pedersen et al. | |
| 2003/0044908 A1 | 3/2003 | Persson | |
| 2006/0040856 A1 | 2/2006 | DeFrees et al. | |
| 2009/0291890 A1 | 11/2009 | Madison et al. | |
| 2010/0036001 A1 | 2/2010 | DeAngelis | |
| 2012/0093840 A1 | 4/2012 | Ostergaard et al. | |
| 2013/0004524 A1 | 1/2013 | Buchardt et al. | |
| 2013/0040888 A1 | 2/2013 | Peschke et al. | |
| 2015/0105321 A1 | 4/2015 | Oestergaard et al. | |
| 2015/0225711 A1 | 8/2015 | Behrens et al. | |
| 2015/0259665 A1 | 9/2015 | Behrens et al. | |

FOREIGN PATENT DOCUMENTS

| | | |
|---|---|---|
| WO | 0158935 A2 | 8/2001 |
| WO | 02/22776 A2 | 3/2002 |
| WO | 03031464 A2 | 4/2003 |
| WO | 2005/014035 A2 | 2/2005 |
| WO | 2005/075635 A2 | 8/2005 |
| WO | 2006/127896 A2 | 11/2006 |
| WO | 2006/134174 A2 | 12/2006 |
| WO | 2007022512 A2 | 2/2007 |
| WO | 2007/031559 A2 | 3/2007 |
| WO | 2008/025856 A2 | 3/2008 |
| WO | 2008/074032 A1 | 6/2008 |
| WO | 2008127702 A2 | 10/2008 |
| WO | 2009126307 A2 | 10/2009 |
| WO | 2010/030342 A2 | 3/2010 |
| WO | 2011092242 A1 | 8/2011 |
| WO | 2011101277 A1 | 8/2011 |
| WO | 2012/007324 A2 | 1/2012 |
| WO | 2012035050 A2 | 3/2012 |
| WO | 2014/060401 | 4/2014 |
| WO | 2014060397 A1 | 4/2014 |
| WO | 2014140103 A2 | 9/2014 |

OTHER PUBLICATIONS

Agersoe .H. et al., Recombinant human factor VIIa (rFVIIa) cleared principally by antithrombin following intravenous administration in hemophilia patients. J. Thromb. Haemost. vol. 9, No. 2, Year (2011), pp. 333-338.
Database Geneseq [Online]; Jan. 7, 2010,; "Human factor VII (FVII) mutein, SEQ:346.", XP002722258,; retrieved from EBI accession No. GSP:AXS64259; Database accession No. AXS64259; * sequence *; & WO 2009/126307 A2 (Catalyst Biosciences; Inc [US]; Madison Edwin L [US]; Thanos; Christophe) Oct. 15, 2009.
Database UniProt [Online] Sep. 18, 2013 "RecName: Full=Coagulation factor VII; EC=3.4.21.21; AltName: Full=Serum prothrombin conversion accelerator; Contains: RecName: Full=Factor VII light chain; Contains: RecName: Full=Factor VII heavy chain;", XP002722259, retrieved from EBI accession No. UNIPROT:P22457 Database accession No. P22457* sequence * & Hiroyuki Takeya et al: "Bovine Factor VII . . . Amino Acid Sequence" J. Biol. Chem, Oct. 15, 1988, pp. 14868-14877 [retrieved on Mar. 25, 2014].
Database UniProt [Online]; Sep. 18, 2013, "SubName: Full=Uncharacterized protein;", XP002722260,; retrieved from EBI accession No. UNIPROT:G3VNT5, Database accession No. G3VNT5; * sequence *; & W. Miller et al: "Genetic diversity and population structure of the endangered; marsupial *Sarcophilus harrisii* (Tasmanian devil) ", Proceedings of the National Academy of Sciences, vol. 108. No. 30, Year 2011, pp. 12348-12353. XP055109905.; ISSN: 0027-8424. 001: 10. 1073/pnas. 1102838108.

(Continued)

*Primary Examiner* — Julie Ha
*Assistant Examiner* — Li Ni Komatsu
(74) *Attorney, Agent, or Firm* — Jianjie Hu

(57) ABSTRACT

The present invention relates to modified coagulation Factor VII polypeptides exhibiting increased resistance to antithrombin inactivation and enhanced proteolytic activity. The present invention also relates to polynucleotide constructs encoding such polypeptides, vectors and host cells comprising and expressing such polynucleotides, pharmaceutical compositions, uses and methods of treatment.

10 Claims, 19 Drawing Sheets

(56) References Cited

OTHER PUBLICATIONS

De Paula et al, Recombinant factor Vlla analog (vatreptacog alfa [activated]); for treatment of joint bleeds in hemophilia patients with inhibitors: a randomized controlled trial, Journal of Thrombosis and Haemostasis, 10, Year 2012, pp. 81-89.
DeAngelis Paul L., HEPtune: A Process of Conjugating a Naturally Occurring Sugar Molecule, Heparosan, to a Drug for Enhanced Drug Delivery, Drug develpment and delivery drug delivery technology, vol. 13, No. 1, Jan. 2013. Retrieved from the internet. ; http://drugdev.com/Main/Back-Issues/-HEPtune-A-Process-of-Conjugating-a-Naturally-Occu-160.aspx; [retrieved on Oct. 15, 2014].
Ditte M. Karpf et al., Prolonged half-life of glycoPEGylated rFVlla variants compared to native rFVlla, Thrombosis Research, vol. 128, No. 2, Year 2011, pp. 191-195.
H. J. Metzner et al., Extending the pharmacokinetic half-life of coagulation factors by fusion to recombinant albumin, Thrombosis and Haemostasis, vol. 110, No. 5, Year 2013, pp. 931-939.
Harvey, SB et al., Mutagenesis of the y-Carboxyglutamic Acid Domain of Human Factor VII to Generate Maximum Enhancement of the Membrane Contact Site. J. Biol. Chem. 278, Year 2003, pp. 8363-8369.
Huntington,J. A., Mechanisms of glycosaminoglycan activation of the serpins in; hemostasis. J. Thromb. Haemost. vol. 1, No. 7, Year 2003, pp. 1535-1549.
Kounnas,M.Z. et al., Cellular internalization and degradation of antithrombin III-thrombin, heparin cofactor II-thrombin, and alpha 1-antitrypsin-trypsin complexes is mediated by the low density lipoprotein receptor-related protein. J. Biol. Chem. vol. 271, No. 11 Year 1996, pp. 6523-6529.
Lollar,P. et al., Clearance of thrombin from circulation in rabbits by; high-affinity binding sites on endothelium. Possible role in the inactivation of thrombin by; antithrombin III., J. Clin. Invest, vol. 66, No. 6, Year 1980, pp. 1222-1230.
Narita,M., et al. The low-density lipoprotein receptor-related protein (LRP) mediates clearance of coagulation factor Xa in vivo. Blood 91, No . 2, Year 1998, pp. 555-560.
Nayak,R.C et al., Endothelial cell protein C receptor cellular localization and trafficking:; potential functional implications. Blood, 114, No. 9, Year 2009, pp. 1974-1986.
Olson,S.T. et al., Accelerating ability of synthetic oligosaccharides on; antithrombin inhibition of proteinases of the clotting and fibrinolytic systems. Comparison; with heparin and low-molecular-weight heparin. Thromb Haemost vol. 92, Year 2004, pp. 929-939.
Persson Egon et al: "Assignment of molecular properties of a superactive coagulation factor Vlla variant to individual amino acid changes" European Journal of Biochemistry, vol. 269, No. 23, Year 2002, pp. 5950-5955.
Rao, L.V. et al., Binding of factor Vlla to tissue factor permits rapid antithrombin III/heparin inhibition of factor Vlla. Blood 81, No. 10, Year 1993, pp. 2600-2607.
Rao, L.V. et al., Regulation of tissue factor-factor Vlla expression on; cell surfaces: a role for tissue factor-factor Vlla endocytosis. Mol. Cell Biochem. vol. 253, No. 1-2,Year 2003, pp. 131-140.

Wildgoose,P. et al., Measurement of basal levels of factor Vlla in hemophilia A and B patients. Blood 80, No. 1, Year 1992, pp. 25-28.
Deangelis P L "HEPtune: A process of conjugating a Naturally occurring sugar molecule, Heparosan to a drug for enhanced drug delivery",Journal: Drug Development & Delivery,Year Jan. 1, 2013,pp. 1-4, XP002691459, Retrieved from the Internet : URL:http://www.drugdeliverytech.com/ME2/dirmod.asp?sid=&nm=&type=Publishing&mod=Publications%3A%3AArticle&mid=8F3A7027421841978FI8BE895F87F791&tier=4&id=A96E9B93B79B42F4A3FIAD34C03507AF.
Ditte M Karpf et al: "Prolonged h a l f-l i fe of glycoPEGylated rFVlla variants compared to native rFVlla".Journal :Thrombosis Research,Year Aug. 1, 2011 vol. 128. No. 2, pp. 191-195,XP002691140.
Dufner G et al.Base- and Sugar-Modified Cytidine Monophosphate N-Acetylneuraminic Acid (CMP-Neu5Ac) Analogues—Synthesis and Studies with alpha(2-6)-Sialyltransferase from Rat Liver.Journal Eur. J. Org. Chem Year 2000, pp. 1467-1482 XP055124461, Retrieved from the Internet: URL :http://onlinelibrary.wiley.com/doi/10.1002/%28SICI%291099-0690%28200004%292000:8%3C1467::AID-EJOCI467%3E3.0.CO;2-E/pdf[retrieved on Jun. 20, 2014].
Malmstrom J, Characterization of 40 kDa poly(ethylene glycol) polymers by proton transfer reaction QTOF mass spectrometry and 1H-NMR spectroscopy, Analytical Bioanalytical Chemistry, Year2012, vol. 403, pp. 1167-1177.
Stennicke H. R et al.A novel B-domain O-glycoPEGylated FVIII (N8-GP) demonstrates full efficacy and prolonged effect in hemophilic mice models, Journal : Blood, Year 2013, vol. 121 Issue11, pp. 2108-2016.
Stennicke HR et al.Generation and biochemical characterization of glycoPEGylated factor Vlla derivatives, Journal : Thrombosis haemostatis, Year 2008, vol. 100, Issue 5 pp. 920-928.
Coagulopathy treatment, from http://www.healthgrades.com/conditions/coagulopathy—treatments, p. 1, accessed Dec. 5, 2014.
Morrissey J. H. et al., Quantitation of Activated Factor VI1 Levels in Plasma Using a Tissue Factor Mutant Selectively Deficient in Promoting Factor VII Activation, Journal: Blood, Year: 1993, vol. 18, No. 3, pp. 734-744.
Karpf D. M. et al., Prolonged half-life of glycoPEGylated rFVIIa variants compared to native rFVIIa, Journal: Thrombosis Research, Year: 2011, vol. 128, pp. 191-195.
Harlan T et al., Caisson Biotech: Innovation in Drug Delivery Using a Naturally Occurring Sugar Molecule, Journal: Drug Development & Delivery, Year: 2012, vol. 12, No. 6, pp. 59-61.
Bouley J. et al., Hustling on Half-lives, Journal: Drug Discovery News, vol. 8, No. 6, Year: 2012, whole document.
Kelsen K., Novo Nordisk, Caisson Biotech announces license agreement, Journal: Drug Discovery News, Year: 2012, the whole document.
Deangelis P. L., HEPtune: A Process of Conjugating a Naturally Occurring Sugar Molecule, Heparosan, to a Drug for Enhanced Drug Delivery, Journal: Drug Development & Delivery, Year: 2013, pp. 1-4.
Chavaroche, A. et al. "Production Methods for Heparosan, a Precursor of Heparin and Heparan Sulfate." Carbohydrate Polymers. 2013 vol. 93 pp. 38-47.

```
                                16        30        40        50        60        70
                                153       167       176       186       196       210
Human      (SEQ ID NO: 2)   IVGGKVCPKGECPWQVLLLVNGAQLCGGTLINTIWVVSAAHCFDKIKNWRNLIAVLGEHD
Chimpanzee (SEQ ID NO: 3)   IVGGKVCPKGECPWQVLLLVNGAQLCGGTLINTIWVVSAAHCFDKIKNWRNLIAVLGEHD
Dog        (SEQ ID NO: 4)   IVGGKVCPKGECPWQAAVKVDGKLLCGGTLLCGGTLIDAAWVSAAHCFERIKNWKNLITVVLGEHD
Porcine    (SEQ ID NO: 5)   IVGGHVCPKGECPWQAMLKLKGALLCGGTLLNTSWVVSAAHCFDRIRSWKDLTVVLGEHD
Bovine     (SEQ ID NO: 6)   IVGGHVCPKGECPWQAVLKINGLLCGGTLVGPAWVSAAHCFERLRSRGNLTAVLGEHD
Mouse      (SEQ ID NO: 7)   IVGGNVCPKGECPWQAVLKINGLLCGAVLLDARWIVTAAHCFDNIRYWGNITVVMGEHD
Rat        (SEQ ID NO: 8)   IVGGYVCPKGECPWQAVLKFNEALLCGAVLLDTRWIVTAAHCFDKFGKIVNITVVLGEHD
Rabbit     (SEQ ID NO: 9)   IVGGKVCPKGECPWQAALMNGSTLLCGGSLLDTHWVVSAAHCFDKLSSLRNLITIVLGEHD
                            ****  *************       *  ***  ** *   * *******  *   * ** ****

80        90       100       110       120       129
                                220       230       240       250       260       269
Human                       LSEHDGDEQSRRVAQVIIPSTYVPGTTNHDIALLRLHQPVVLTDHVVPLCLPERIFSERT
Chimpanzee                  LSEHDGDEQSRRVAQVIIPSTYVPGTTNHDIALLRLHQPVVLTDHVVPLCLPERIFSERT
Dog                         LSEDDGDEQERHVARVIVPDKYIPLKTNHDIALLHLHRTPVAYTDHVVPLCLPEKTFSERT
Porcine                     LSKDEGDEQERPVAQVFVPDKYVPGKTDHDLALVRLARPVALTDHVVPLCLPERSFSERT
Bovine                      LSRVEGPEQERRVAQIIVPKQYVPGQTDHDVALLQLAQPVALGDHVAPLCLPDPDFADQT
Mouse                       FSEKDGDEQVRRRVTQVIMPDKYIRGKINHDIALLRLHRPVTFTDYVVPLCLPEKSFSENT
Rat                         FSEKEGTEQVRLVEQVIMPNKYTRGRIDHDIALVRLHRPVTFTDYVVPLCLPERAFSENT
Rabbit                      LSEHEGDEQVRHVAQLIMPDKYVPGKTDHDIALLRLLQPAALTNNVVPLCLPERNFSEST
                            .*       *    *  ** .*     * .  **.**..*    *  ******* *.. *

137       150       160       170       180
                               280       292       302       312       327
Human                       LAFVRFSLVSGWGQLLDRGATALELMVLNVPRLMTQDCLQQSRKVGDSPNITEYMFCAGY
Chimpanzee                  LAFVRFSLVSGWGQLLDRGATALELMVLNVPRLMTQDCLQQSRKVGDSPNITEYMFCAGY
Dog                         LAFIRFSTVSGWGRLLDRGATALQLMAIDVPRVMTQDCQEQSRRRSGSPAITENMFCAGY
Porcine                     LAFIRFSAVSGWGRLLDRGAKARVLMAIQVPRLMTQDCLEQARRRPGSPSITDNMFCAGY
Bovine                      LAFVRFSAVSGWGRLLERGVTARKLMVVLVPRLLTQDCLQQSRQRPGGPVVTDNMFCAGY
Mouse                       LARIRFSRVSGWGQLLDRGATALELMSIEVPRLMTQDCLEHAKHSSNTPKITENMFCAGY
Rat                         LASIRFSRVSGWGQLLDRGATALELMVIEVPRLMTQDCLEHAKHSANTPRITENMFCAGY
Rabbit                      LATIRFSRVSGWGQLLYRGALARELMAIDVPRLMTQDCVEQSEHKPGSPEVTGNMFCAGY
                            ** .*** ****** ** **.    **   ***.****    .    *.  * *******
```

Fig. 1

```
             190       200       210       220       230       240
             339       349       359       368       379       389
Human     SDGSKDSCKGDSGGPHATHYRGTWYLTGIVSWGQGCATVGHFGVYTRVSQYIEWLQKLMR
Chimpanzee SDGSKDSCKGDSGGPHATHYRGTWYLTGIVSWGQGCASVGHFGVYTRVSQYIEWLQKLMR
Dog       LDGSKDACQGDSGGPHATKFQGTWYLTGVVSWGEGCAAEGHFGVYTRVSQYIEWLRQLMV
Porcine   LDGSKDACKGDSGGPHATRFRGTWFLTGVVSWGEGCAATGRFGVYTRVSRYTAWLLGLMS
Bovine    SDGSKDACKGDSGGPHATRFRGTWFLTGVVSWGEGCAAAGHFGIYTRVSRYTAWLRQLM-
Mouse     MDGTKDACKGDSGGPHATHYHGTWYLTGVVSWGEGCAAIGHIGVYTRVSQYIDWLVRHM-
Rat       MDGTKDACKGDSGGPHATHYHGTWYLTGVVSWGEGCAAIGHIGVYTRVSQYIDWLVKYM-
Rabbit    LDGSKDACKGDSGGPHATSYHGTWYLTGVVSWGEGCAAVGHVGVYTRVSRYTEWLSRLMR
          ..**.*.:*******  :.*** *** *.****.****:.. *.:. ******.*  **  *

250
             399
Human      SEPRP-GVLLRAPF-P
Chimpanzee SEPRP-GVLLRAPF-P
Dog        SSHTLR-GLLRAPL-P
Porcine    APPPSEGLLRAPL-P
Bovine     GHPPSRQGFFQVPLLP
Mouse      -DSKLQVGVFRLPL-L
Rat        -DSKLRVGISRVSL-L
Rabbit     S--KLHHGIQRHPF-P
                 :         
```

Fig. 1 (cont.)

COAGULATION FACTOR VII POLYPEPTIDES

CROSS-REFERENCE TO RELATED APPLICATIONS

This application is a continuation of U.S. application Ser. No. 14/514,794, filed Oct. 15, 2014, which claims priority under 35 U.S.C. §119 of U.S. Provisional Application 61/895,438, filed Oct. 25, 2013; this application further claims priority of European Application 13188715.0, filed Oct. 15, 2013, and European Application 14154875.0, filed Feb. 12, 2014; the contents of all above-named applications are incorporated herein by reference.

TECHNICAL FIELD

The present invention relates to coagulation Factor VII (Factor VII) polypeptides having pro-coagulant activity. It also relates to pharmaceutical compositions comprising such polypeptides, methods of treatment and uses of such polypeptides.

SEQUENCE LISTING

SEQ ID NO. 1: Wild type human coagulation Factor VII.
SEQ ID NO. 2: Protease domain of human coagulation Factor VII.
SEQ ID NO. 3: Protease domain of hominin (chimpanzee) coagulation Factor VII.
SEQ ID NO. 4: Protease domain of canine (dog) coagulation Factor VII.
SEQ ID NO. 5: Protease domain of porcine (pig) coagulation Factor VII.
SEQ ID NO. 6: Protease domain of bovine (cattle) coagulation Factor VII.
SEQ ID NO. 7: Protease domain of murine (mouse) coagulation Factor VII.
SEQ ID NO. 8: Protease domain of murine (rat) coagulation Factor VII.
SEQ ID NO. 9: Protease domain of lapine (rabbit) coagulation Factor VII.

The instant application contains a Sequence Listing which has been submitted in ASCII format via EFS-Web and is hereby incorporated by reference in its entirety. Said ASCII copy, created on Nov. 5, 2015, is named 8719US03_SeqList and is 22 kilobytes in size.

BACKGROUND OF INVENTION

An injury to a blood vessel activates the haemostatic system that involves complex interactions between cellular and molecular components. The process that eventually causes the bleeding to stop is known as haemostasis. An important part of haemostasis is coagulation of the blood and the formation of a clot at the site of the injury. The coagulation process is highly dependent on the function of several protein molecules. These are known as coagulation factors. Some of the coagulation factors are proteases which can exist in an inactive zymogen or an enzymatically active form. The zymogen form can be converted to its enzymatically active form by specific cleavage of the polypeptide chain catalyzed by another proteolytically active coagulation factor.

Factor VII is a vitamin K-dependent plasma protein synthesized in the liver and secreted into the blood as a single-chain glycoprotein. The Factor VII zymogen is converted into an activated form (Factor VIIa) by specific proteolytic cleavage at a single site, i.e. between R152 and I153 of SEQ ID NO: 1, resulting in a two chain molecule linked by a single disulfide bond. The two polypeptide chains in Factor VIIa are referred to as light and heavy chain, corresponding to residues 1-152 and 153-406, respectively, of SEQ ID NO: 1 (wild type human coagulation Factor VII). Factor VII circulates predominantly as zymogen, but a minor fraction is in the activated form (Factor VIIa).

The blood coagulation process can be divided into three phases: initiation, amplification and propagation. The initiation and propagation phases contribute to the formation of thrombin, a coagulation factor with many important functions in haemostasis. The coagulation cascade starts if the single-layered barrier of endothelial cells that line the inner surface of blood vessels becomes damaged. This exposes subendothelial cells and extravascular matrix proteins to which platelets in the blood will stick to. If this happens, Tissue Factor (TF) which is present on the surface of sub-endothelial cells becomes exposed to Factor VIIa circulating in the blood. TF is a membrane-bound protein and serves as the receptor for Factor VIIa. Factor VIIa is an enzyme, a serine protease, with intrinsically low activity. However, when Factor VIIa is bound to TF, its activity increases greatly. Factor VIIa interaction with TF also localizes Factor VIIa on the phospholipid surface of the TF bearing cell and positions it optimally for activation of Factor X to Xa. When this happens, Factor Xa can combine with Factor Va to form the so-called "prothombinase" complex on the surface of the TF bearing cell. The prothrombinase complex then generates thrombin by cleavage of prothrombin. The pathway activated by exposing TF to circulating Factor VIIa and leading to the initial generation of thrombin is known as the TF pathway. The TF:Factor VIIa complex also catalyzes the activation of Factor IX to Factor IXa. Then activated Factor IXa can diffuse to the surface of platelets which are sticking to the site of the injury and have been activated. This allows Factor IXa to combine with FVIIIa to form the "tenase" complex on the surface of the activated platelet. This complex plays a key role in the propagation phase due to its remarkable efficiency in activating Factor X to Xa. The efficient tenase catalyzed generation of Factor Xa activity in turn leads to efficient cleavage of prothrombin to thrombin catalyzed by the prothrombinase complex.

If there are any deficiencies in either Factor IX or Factor VIII, it compromises the important tenase activity, and reduces the production of the thrombin which is necessary for coagulation. Thrombin formed initially by the TF pathway serves as a pro-coagulant signal that encourages recruitment, activation and aggregation of platelets at the injury site. This results in the formation of a loose primary plug of platelets. However, this primary plug of platelets is unstable and needs reinforcement to sustain haemostasis. Stabilization of the plug involves anchoring and entangling the platelets in a web of fibrin fibres.

The formation of a strong and stable clot is dependent on the generation of a robust burst of local thrombin activity. Thus, deficiencies in the processes leading to thrombin generation following a vessel injury can lead to bleeding disorders e.g. haemophilia A and B. People with haemophilia A and B lack functional Factor VIIIa or Factor IXa, respectively. Thrombin generation in the propagation phase is critically dependent on tenase activity, i.e. requires both Factor VIIIa and FIXa. Therefore, in people with haemophilia A or B proper consolidation of the primary platelet plug fails and bleeding continues.

Replacement therapy is the traditional treatment for hemophilia A and B, and involves intravenous administration of Factor VIII or Factor IX. In many cases, however, patients develop antibodies (also known as inhibitors) against the infused proteins, which reduce or negate the efficacy of the treatment. Recombinant Factor VIIa (Novoseven®) has been approved for the treatment of hemophilia A or B patients with inhibitors, and also is used to stop bleeding episodes or prevent bleeding associated with trauma and/or surgery. Recombinant Factor VIIa has also been approved for the treatment of patients with congenital Factor VII deficiency. It has been proposed that recombinant FVIIa operates through a TF-independent mechanism. According to this model, recombinant FVIIa is directed to the surface of the activated blood platelets by virtue of its Gla-domain where it then proteolytically activates Factor X to Xa thus by-passing the need for a functional tenase complex. The low enzymatic activity of FVIIa in the absence of TF as well as the low affinity of the Gla-domain for membranes could explain the need for supraphysiological levels of circulating FVIIa needed to achieve haemostasis in people with haemophilia.

Recombinant Factor VIIa has an in vivo functional half-life of 2-3 hours which may necessitate frequent administration to resolve bleedings in patients. Further, patients often only receive Factor VIIa therapy after a bleed has commenced, rather than as a precautionary measure, which often impinges upon their general quality of life. A recombinant Factor VIIa variant with a longer in vivo functional half-life would decrease the number of necessary administrations, support less frequent dosing and thus holds the promise of significantly improving Factor VIIa therapy to the benefit of patients and care-holders.

WO02/22776 discloses Factor VIIa variants with enhanced proteolytic activity compared to wild-type FVIIa. It has been demonstrated in clinical trials that a Factor VII polypeptide comprising substitutions disclosed in WO02/22776 shows a favourable clinical outcome in terms of efficacy of a variant with enhanced proteolytic activity (de Paula et al (2012) *J Thromb Haemost*, 10:81-89).

WO2007/031559 discloses Factor VII variants with reduced susceptibility to inhibition by antithrombin.

WO2009/126307 discloses modified Factor VII polypeptides with altered procoagulant activity.

In general, there are many unmet medical needs in people with coagulopathies. The use of recombinant Factor VIIa to promote clot formation underlines its growing importance as a therapeutic agent. However, recombinant Factor VIIa therapy still leaves significant unmet medical needs, a recombinant Factor VIIa polypeptides having improved pharmaceutical properties, for example increased in vivo functional half-life and enhanced or higher activity, would meet some of these needs.

SUMMARY OF THE INVENTION

The present invention provides Factor VII polypeptides that are designed to have improved pharmaceutical properties. In one broad aspect, the invention relates to Factor VII polypeptides exhibiting increased in vivo functional half-life as compared to human wild-type Factor VIIa. In another broad aspect, the invention relates to Factor VII polypeptides with enhanced activity as compared to human wild-type Factor VIIa. In a further broad aspect, the invention relates to Factor VII polypeptides exhibiting increased resistance to inactivation by endogenous plasma inhibitors, particularly antithrombin, as compared to human wild-type Factor VIIa.

Provided herein are Factor VII polypeptides with increased in vivo functional half-life which comprise a combination of mutations conferring resistance to antithrombin inactivation and enhanced or little or no loss of proteolytic activity. In a particularly interesting aspect of the present invention the Factor VII polypeptides are coupled to one or more "half-life extending moieties" to increase the in vivo functional half-life.

In one aspect, the invention relates to a Factor VII polypeptide comprising two or more substitutions relative to the amino acid sequence of human Factor VII (SEQ ID NO:1), wherein T293 is replaced by Lys (K), Arg (R), Tyr (Y) or Phe (F) and L288 is replaced by Phe (F), Tyr (Y), Asn (N), or Ala (A) and/or W201 is replaced by Arg (R), Met (M) or Lys (K) and/or K337 is replaced by Ala (A) or Gly (G).

The Factor VII polypeptide of the invention may comprise a substitution of T293 with Lys (K) and a substitution of L288 with Phe (F). The Factor VII polypeptide may comprise a substitution of T293 with Lys (K) and a substitution of L288 with Tyr (Y). The Factor VII polypeptide may comprise a substitution of T293 with Arg (R) and a substitution of L288 with Phe (F). The Factor VII polypeptide may comprise a substitution of T293 with Arg (R) and a substitution of L288 with Tyr (Y). The Factor VII polypeptide may comprise, or may further comprise, a substitution of K337 with Ala (A). The Factor VII polypeptide may comprise a substitution of T293 with Lys (K) and a substitution of W201 with Arg (R).

In an interesting embodiment the invention relates to Factor VII polypeptides coupled with at least one half-life extending moiety.

In another aspect, the invention relates to methods for producing the Factor VII polypeptides of the invention.

In a further aspect, the invention relates to pharmaceutical compositions comprising a Factor VII polypeptide of the invention.

The general object of the present invention is to improve currently available treatment options in people with coagulopathies and to obtain Factor VII polypeptides with improved therapeutic utility.

One object that the present invention has is to obtain Factor VII polypeptides with prolonged in vivo functional half-life while maintaining a pharmaceutically acceptable proteolytic activity. To achieve this, the Factor VII polypeptides of the present invention comprise a combination of mutations conferring reduced susceptibility to inactivation by the plasma inhibitor antithrombin while substantially preserving proteolytic activity; in particularly interesting embodiments of the present invention the Factor VII polypeptides are also coupled to one or more "half-life extending moieties".

Medical treatment with the modified Factor VII polypeptides of the present invention offers a number of advantages over the currently available treatment regimes, such as longer duration between injections, lower dosage, more convenient administration, and potentially improved haemostatic protection between injections.

BRIEF DESCRIPTION OF THE DRAWINGS

FIG. 1 shows amino acid sequence alignment of the FVIIa protease domain from different species.

FIG. 6A shows SDS-PAGE analysis of final FVIIa conjugates. Gel was loaded with HiMark HMW standard (lane 1); FVIIa (lane 2); 13k-HEP-[C]-FVIIa (lane 3); 27k-HEP-[C]-FVIIa (lane 4); 40k-HEP-[C]-FVIIa (lane 5); 52k-HEP-[C]-FVIIa (lane 6); 60k-HEP-[C]-FVIIa (lane 7); 65k-HEP-[C]-FVIIa (lane 8); 108k-HEP-[C]-FVIIa (lane 9) and 157k-HEP-[C]-FVIIa407C (lane 10). FIG. 6B shows SDS-PAGE of glycoconjugated 52k-HEP-[N]-FVIIa. Gel was loaded with HiMark HMW standard (lane 1), ST3Gal3 (lane 2), FVIIa (lane 3), asialo FVIIa (lane 4), and 52k-HEP-[N]-FVIIa (lane 5). [N]-denotes Factor conjugates where HEParosan is attached to the N-glycan. [C]-Denotes Factor conjugates where Heparosan is attached to a cystein residue.

DETAILED DESCRIPTION

Figure 2:
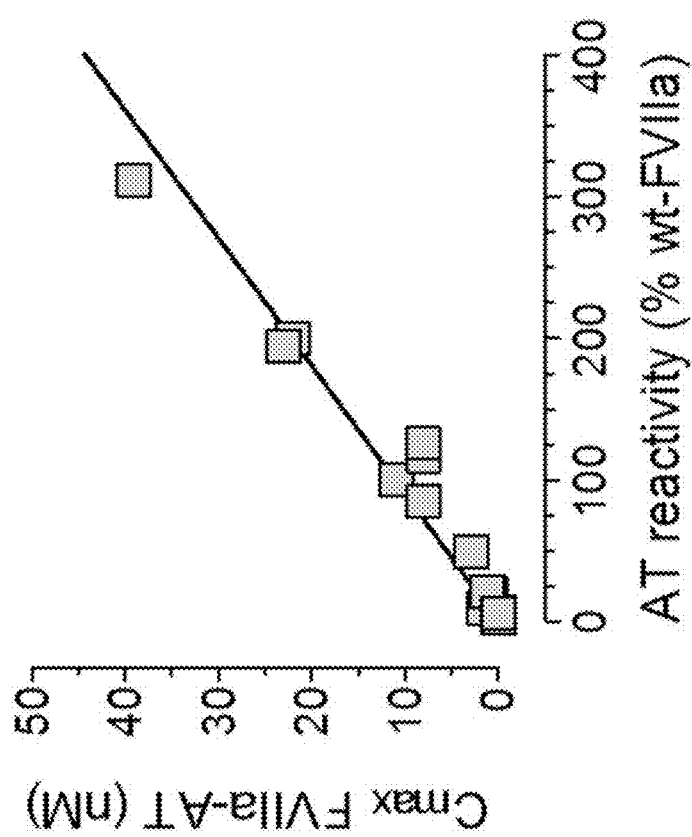
FIG. 2 shows the correlation between in vitro antithrombin reactivity with the in vivo accumulation of FVIIa-antithrombin complexes.

The present invention relates to the design and use of Factor VII polypeptides exhibiting improved pharmaceutical properties.

In one aspect, the present invention relates to the design and use of Factor VII polypeptides exhibiting increased in vivo functional half-life, reduced susceptibility to inactivation by the plasma inhibitor antithrombin and enhanced or preserved proteolytic activity. It has been found by the inventors of the present invention that specific combinations of mutations in human Factor VII in combination with conjugation to half-life extending moieties confer the above mentioned properties. The Factor VII polypeptides of the invention have an extended functional half-life in blood which is therapeutically useful in situations where a longer lasting pro-coagulant activity is wanted. Such Factor VII polypeptides comprise a substitution of T293 with Lys (K), Arg (R), Tyr (Y) or Phe (F). In this aspect, the invention relates to a Factor VII polypeptide comprising two or more substitutions relative to the amino acid sequence of human Factor VII (SEQ ID NO:1), wherein T293 is replaced by Lys (K), Arg (R), Tyr (Y) or Phe (F) and L288 is replaced by Phe (F), Tyr (Y), Asn (N), Ala (A), or Trp (W). The invention also relates to a Factor VII polypeptide comprising two or more substitutions relative to the amino acid sequence of human Factor VII (SEQ ID NO:1), wherein T293 is replaced by Lys (K), Arg (R), Tyr (Y) or Phe (F) and W201 is replaced by Arg (R), Met (M), or Lys (K). Furthermore, the invention relates to a Factor VII polypeptide comprising two or more substitutions relative to the amino acid sequence of human Factor VII (SEQ ID NO:1), wherein T293 is replaced by Lys (K), Arg (R), Tyr (Y) or Phe (F) and K337 is replaced by Ala (A) or Gly (G). Optionally, Factor VII polypeptides of the invention may further comprise substitution of Q176 with Lys (K), Arg (R) or Asn (N). Optionally, Factor VII polypeptides of the invention may further comprise substitution of Q286 with Asn (N). In another aspect, the present invention relates to the design and use of Factor VII polypeptides exhibiting enhanced proteolytic activity. It has been found by the inventors of the present invention that specific mutations in human Factor VII at positions L288 and/or W201 confer enhanced proteolytic activity to Factor VII polypeptides. In this aspect, the invention relates to a Factor VII polypeptide comprising one or more substitutions relative to the amino acid sequence of human Factor VII (SEQ ID NO: 1), wherein L288 is replaced by Phe (F), Tyr(Y), Asn (N), Ala (A) or Trp (W), with the proviso that the polypeptide does not have the following pair of substitutions: L288N/R290S or L288N/R290T. Further according to this aspect, the invention relates to a Factor VII polypeptide comprising one or more substitutions relative to the amino acid sequence of human Factor VII (SEQ ID NO:1), characterized in that one substitution is where W201 is replaced by Arg (R), Met (M) or Lys (K).

Factor VII

Coagulation Factor VII (Factor VII) is a glycoprotein primarily produced in the liver. The mature protein consists of 406 amino acid residues defined by SEQ ID NO: 1 (also disclosed in, for example, in U.S. Pat. No. 4,784,950) and is composed of four domains. There is an N-terminal gamma-carboxyglutamic acid (Gla) rich domain followed by two epidermal growth factor (EGF)-like domains and a C-terminal trypsin-like serine protease domain. Factor VII circulates in plasma, predominantly as a single-chain molecule. Factor VII is activated to Factor VIIa by cleavage between residues Arg152 and Ile153, resulting in a two-chain protein held together by a disulphide bond. The light chain contains the Gla and EGF-like domains, while the heavy chain is the protease domain. Specific Glu (E) residues, i.e. E6, E7, E14, E16, E19, E20, E25, E26, E29 and E35, according to SEQ ID NO: 1 in Factor VII may be post-translationally gamma-carboxylated. The gamma-carboxyglutamic acid residues in the Gla domain are required for coordination of a number of calcium ions, which maintain the Gla domain in a conformation mediating interaction with phospholipid membranes.

The terms FVII and "Factor VII" herein refers to the uncleaved single-chain zymogen, Factor VII, as well as the cleaved, two-chain and thus activated protease, Factor VIIa. "Factor VII" includes natural allelic variants of Factor VII that may exist and differ from one individual to another. A human wild-type Factor VII sequence is provided in SEQ ID NO: 1. The term "Factor VII polypeptide" herein refers to the uncleaved single chain zymogen polypeptide variant of Factor VII (as described herein), as well as the cleaved, two chain and thus activated protease.

Factor VII and Factor VII polypeptides may be plasma-derived or recombinantly produced, using well known methods of production and purification. The degree and location of glycosylation, gamma-carboxylation and other post-translational modifications may vary depending on the chosen host cell and its growth conditions.

Factor VII Polypeptides

The terms "Factor VII" or "FVII" denote Factor VII polypeptides.

The term "Factor VII polypeptide" encompasses wild type Factor VII molecules as well as Factor VII variants, Factor VII conjugates and Factor VII that has been chemically modified. Such, variants, conjugates and chemically modified Factor VII may exhibit substantially the same, or improved, activity relative to wild-type human Factor VIIa.

The term "activity" of a Factor VII polypeptide, as used herein, refers to any activity exhibited by wild-type human Factor VII, and includes, but is not limited to, coagulation or coagulant activity, pro-coagulant activity, proteolytic or catalytic activity such as to effect Factor X activation or Factor IX activation; ability to bind TF, Factor X or Factor IX; and/or ability to bind to phospholipids. These activities can be assessed in vitro or in vivo using recognized assays, for example, by measuring coagulation in vitro or in vivo. The results of such assays indicate that a polypeptide exhibits an activity that can be correlated to activity of the polypeptide in vivo, in which in vivo activity can be referred to as biological activity. Assays to determine activity of a Factor VII polypeptide are known to those of skill in the art. Exemplary assays to assess the activity of a FVII polypeptide include in vitro proteolysis assays, such as those described in the Examples, below.

The terms "enhanced, or preserved activity", as used herein, refer to Factor VIIa polypeptides that exhibit substantially the same or increased activity compared to wild type human Factor VIIa, for example i) substantially the same or increased proteolytic activity compared to recombinant wild type human Factor VIIa in the presence and/or absence of TF; ii) to Factor VII polypeptides with substantially the same or increased TF affinity compared to recombinant wild type human Factor VIIa; iii) to Factor VII polypeptides with substantially the same or increased affinity for the activated platelet; or iv) Factor VII polypeptides with substantially the same or increased affinity/ability to bind to Factor X or Factor IX compared to recombinant wild type human Factor VIIa. For example preserved activity means that the amount of activity that is retained is or is about 10%, 20%, 30%, 40%, 50%, 60%, 70%, 80%, 90%, 100% or more of the activity compared to wild type human Factor VIIa. For example enhanced activity means that the amount of activity that is retained is or is about 110%, 120%, 130%, 140%, 150%, 160%, 170%, 180%, 190%, 200%, 300%, 400%, 500%, 1000%, 3000%, 5000%, 10 000%, 30 000% or more of the activity compared to wild type human Factor VIIa.

The term "Factor VII variant", as used herein, is intended to designate a Factor VII having the sequence of SEQ ID NO: 1, wherein one or more amino acids of the parent protein have been substituted by another naturally occurring amino acid and/or wherein one or more amino acids of the parent protein have been deleted and/or wherein one or more amino acids have been inserted in the protein and/or wherein one or more amino acids have been added to the parent protein. Such addition can take place either at the N- or at the C-terminus of the parent protein or both. In one embodiment a variant is at least 95% identical with the sequence of SEQ ID NO: 1. In another embodiment a variant is at least 80, 85, 90, 95, 96, 97, 98 or 99% identical with the sequence of SEQ ID NO: 1. As used herein, any reference to a specific position refers to the corresponding position in SEQ ID NO: 1.

In some embodiments, the Factor VII variants of this invention have an enhanced or preserved activity compared to wild type human Factor VIIa.

The terminology for amino acid substitutions used in this description is as follows. The first letter represents the amino acid naturally present at a position of SEQ ID NO:1. The following number represent the position in SEQ ID NO:1. The second letter represents the different amino acid substituting the natural amino acid. An example is K197A-Factor VII, wherein the Lysine at position 197 of SEQ ID NO:1 is replaced by a Alanine.

In the present context the three-letter or one-letter abbreviations of the amino acids have been used in their conventional meaning as indicated in below. Unless indicated explicitly, the amino acids mentioned herein are L-amino acids. Abbreviations for amino acids:

| Amino acid | Three-letter code | One-letter code |
|---|---|---|
| Glycine | Gly | G |
| Proline | Pro | P |
| Alanine | Ala | A |
| Valine | Val | V |
| Leucine | Leu | L |
| Isoleucine | Ile | I |

| Amino acid | Three-letter code | One-letter code |
|---|---|---|
| Methionine | Met | M |
| Cysteine | Cys | C |
| Phenylalanine | Phe | F |
| Tyrosine | Tyr | Y |
| Tryptophan | Trp | W |
| Histidine | His | H |
| Lysine | Lys | K |
| Arginine | Arg | R |
| Glutamine | Gln | Q |
| Asparagine | Asn | N |
| Glutamic Acid | Glu | E |
| Aspartic Acid | Asp | D |
| Serine | Ser | S |
| Threonine | Thr | T |

The term "Factor VII conjugates" as used herein, is intended to designate a Factor VII polypeptide, in which one or more of the amino acids and/or one or more of the attached glycan moieties have been chemically and/or enzymatically modified, such as by alkylation, glycosylation, acylation, ester formation, disulfide bond formation, or amide formation.

In some embodiments, the Factor VII conjugates of the invention exhibit substantially the same or enhanced biological activity relative to wild-type Factor VII.

Enhanced Proteolytic Activity

Factor VII polypeptides with certain mutations of residues L288 and W201 have, surprisingly, been shown by the inventors to exhibit enhanced proteolytic activity.

The Factor VII variant K337A, as described in WO02/22776, has been described to have enhanced proteolytic activity. The Factor VII variants L305V and L305I, as described in WO03/027147, have also been described to have higher intrinsic activity.

The proteolytic activity may be determined by any suitable method known in the art as further discussed below.

For example enhanced proteolytic activity means that the amount of activity that is retained is or is about 110%, 120%, 130%, 140%, 150%, 160%, 170%, 180%, 190%, 200%, 300%, 400%, 500%, 1000%, 3000%, 5000%, 10 000%, 30 000% or more of the activity compared to wild type human Factor VIIa.

Half-Life—Resistance to Inactivation by Plasma Inhibitors

Besides in vivo clearance, in vivo functional half-life is of importance to the period of time during which the compound is "therapeutically available" in the body. The circulating half-life of recombinant human wild type Factor VIIa is about 2.3 hours ("Summary Basis for Approval for NovoSeven©", FDA reference number 96 0597).

The term "in vivo functional half-life" is used in its normal meaning, i.e., the time required for reducing the biological activity of the Factor VII polypeptide remaining in the body/target organ with 50% in the terminal phase, or the time at which the activity of the Factor VII polypeptide is 50% of its initial value. Alternative terms to in vivo half-life include terminal half-life, plasma half-life, circulating half-life, circulatory half-life, and clearance half-life. Half-life may be determined by suitable methods known in the art, such as that described in Example 17 and those described in Introduction to Pharmacokinetics and Pharmacodynamics: The Quantitative Basis of Drug Therapy (Thomas N. Tozer, Malcolm Rowland).

The term "increased" as used about the in vivo functional half-life or plasma half-life is used to indicate that the relevant half-life of the polypeptide is increased relative to that of a reference molecule, such as wild-type human Factor VIIa as determined under comparable conditions.

In some embodiments, the Factor VII polypeptides of the invention exhibit increased in vivo functional half-life relative to wild-type human Factor VIIa. For instance the relevant half-life may be increased by at least about 25%, such as by at least about 50%, e.g., by at least about 100%, 150%, 200%, 500%, 1000%, 3000%, 5000%, 10 000%, 30 000% or more.

Despite the detailed understanding of the biochemistry and pathophysiology of the coagulation cascade, the mechanistic basis for the clearance of the individual coagulation factors from circulation remains largely unknown. The marked differences in the circulating half-lives of Factor VII and its activated form Factor VIIa compared with zymogen and enzyme forms of other vitamin K-dependent proteins suggest the existence of specific and distinct clearance mechanisms for Factor VIIa. Two types of pathways appear to be operable in the clearance of Factor VIIa—one resulting in elimination of the intact protein, the other mediated by plasma inhibitors and leading to proteolytic inactivation.

Antithrombin III (antithrombin, AT) is an abundant plasma inhibitor and targets most proteases of the coagulation system, including Factor VIIa. It is present at micromolar concentrations in plasma and belongs to the serpin family of serine protease inhibitors that irreversibly bind and inactivate target proteases by a suicide substrate mechanism. The inhibition by antithrombin appears to constitute the predominant clearance pathway of recombinant Factor VIIa in vivo following intravenous administration. In a recent study of the pharmacokinetics of recombinant Factor VIIa in haemophilia patients, about 60% of the total clearance could be attributed to this pathway (Agerso et al. (2011) *J Thromb Haemost,* 9, 333-338).

In some embodiments, the Factor VII polypeptides of the invention exhibit increased resistance to inactivation by the endogenous plasma inhibitors, particularly antithrombin, relative to wild-type human Factor VIIa.

It has been found by the inventors of the present invention that by combining the two groups of mutations mentioned above, i.e. mutations conferring increased AT resistance and mutations conferring enhanced proteolytic activity, an increased or preserved activity is achieved while maintaining high resistance to inhibitor inactivation. That is, the Factor VII polypeptides of the present invention comprising a combination of mutations exhibit increased resistance to antithrombin inactivation as well as substantially preserved proteolytic activity. When the Factor VII polypeptides of the invention are conjugated with one or more half-life extending moieties a surprisingly improved effect on half-life extension is achieved. Given these properties, such conjugated Factor VII polypeptides of the invention exhibit increased circulatory half-life while maintaining a pharmaceutically acceptable proteolytic activity. Consequently, a lower dose of such conjugated Factor VII polypeptide may be required to obtain a functionally adequate concentration at the site of action and thus it will be possible to administer a lower dose and/or with lower frequency to the subject having bleeding episodes or needing enhancement of the normal haemostatic system.

Additional Modifications

The Factor VII polypeptides of the invention may comprise further modifications, in particular further modifications which confer additional advantageous properties to the Factor VII polypeptide. Thus, in addition to the amino acid substitutions mentioned above, the Factor VII polypeptides of the invention may for example comprise further amino acid modification, e.g. one further amino acid substitution. In one such embodiment, the Factor VII polypeptide of the invention has an additional mutation or addition selected from the group R396C, Q250C, and 407C, as described e.g. in WO2002077218.

The Factor VII polypeptides of the invention may comprise additional modifications that are or are not in the primary sequence of the Factor VII polypeptide. Additional modifications include, but are not limited to, the addition of a carbohydrate moiety, the addition of a half-life extending moiety, e.g. the addition of a, PEG moiety, an Fc domain, etc. For example, such additional modifications can be made to increase the stability or half-life of the Factor VII polypeptide.

Half-Life Extending Moieties or Groups

The term "half-life extending moieties" are herein used interchangeably and understood to refer to one or more chemical groups attached to one or more amino acid site chain functionalities such as —SH, —OH, —COOH, —CONH2, —NH2, and/or one or more N- and/or O-glycan structures and that can increase in vivo functional half-life of proteins/polypeptides when conjugated/coupled to these proteins/polypeptides.

The in vivo functional half-life may be determined by any suitable method known in the art as further discussed below (Example 17).

Examples of half-life extending moieties include: Biocompatible fatty acids and derivatives thereof, Hydroxy Alkyl Starch (HAS) e.g. Hydroxy Ethyl Starch (HES), Poly Ethylen Glycol (PEG), Poly (Glyx-Sery)n (HAP), Hyaluronic acid (HA), Heparosan polymers (HEP), Phosphorylcholine-based polymers (PC polymer), Fleximers, Dextran, Poly-sialic acids (PSA), Fc domains, Transferrin, Albumin, Elastin like (ELP) peptides, XTEN polymers, PAS polymers, PA polymers, Albumin binding peptides, CTP peptides, FcRn binding peptides and any combination thereof.

In a particularly interesting embodiment, the Factor VII polypeptide of the invention is coupled with one or more half-life extending moieties.

In one embodiment, a cysteine-conjugated Factor VII polypeptide of the invention have one or more hydrophobic half-life extending moieties conjugated to a sulfhydryl group of a cysteine introduced in the Factor VII polypeptide. It is furthermore possible to link half-life extending moieties to other amino acid residues.

In one embodiment, the Factor VII polypeptide of the invention is disulfide linked to tissue factor, as described e.g. in WO2007115953.

In another embodiment, the Factor VII polypeptide of the invention is a Factor VIIa variant with increased platelet affinity.

Heparosan Conjugates

Factor VII polypeptide heparosan conjugates according to the present invention may have one or more Heparosan polymer (HEP) molecules attached to any part of the FVII polypeptide including any amino acid residue or carbohydrate moiety of the Factor VII polypeptide. Examples of such conjugates are provided in WO2014/060397, which is herein incorporated by reference. Chemical and/or enzymatic methods can be employed for conjugating HEP to a glycan on the Factor VII polypeptide. An example of an enzymatic conjugation process is described e.g. in WO03031464. The glycan may be naturally occurring or it may be engineered in, e.g. by introduction of an N-glycosylation motif (NXT/S where X is any naturally occurring amino acid) in the amino acid sequence of Factor VII using methods well known in the art.

"Cysteine-HEP Factor VII polypeptide conjugates" according to the present invention have one or more HEP molecules conjugated to a sulfhydryl group of a cysteine residue present or introduced in the FVII polypeptide.

In one interesting embodiment of the invention, the Factor VII polypeptide is coupled to a HEP polymer. In one embodiment the HEP polymer coupled to the Factor VII polypeptide has a molecular weight in a range selected from 13-65 kDa, 13-55 kDa, 25-55 kDa, 25-50 kDa, 25-45 kDa, 30-45 kDa, 36-44 kDa and 38-42 kDa, or a molecular weight of 40 kDa.

In one interesting embodiment of the invention, the Factor VII polypeptide is coupled to a HEP polymer on an N-glycan of the Factor VII polypeptide.

In a further embodiment of the invention, two HEP polymers are coupled to the same Factor VII polypeptide via N-glycans. In this embodiment each of the HEP polymer coupled to the Factor VII polypeptide has a molecular weight in a range selected from 13-65 kDa, 13-55 kDa, 25-55 kDa, 25-50 kDa, 25-45 kDa, 30-45 kDa, 36-44 kDa and 38-42 kDa, or a molecular weight of 40 kDa. Preferably, the polymers have identical molecular weight.

In a specific embodiment two 20 kDa-HEP polymers are coupled to the same Factor VII polypeptide via its N-glycans.

In a specific embodiment two 30 kDa-HEP polymers are coupled to the same Factor VII polypeptide via its N-glycans.

In a specific embodiment two 40 kDa-HEP polymers are coupled to the same Factor VII polypeptide via its N-glycans.

Heparosan Polymers

Figure 5A:
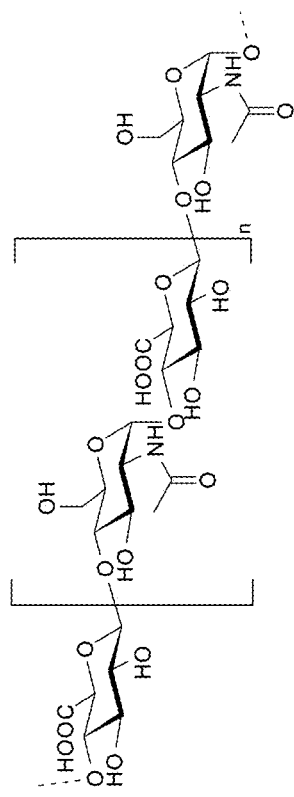
FIG. 5A shows structure of heparosan.

Heparosan (HEP) is a natural sugar polymer comprising (-GlcUA-beta1,4-GlcNAc-alpha1,4-) repeats (see FIG. 5A). It belongs to the glycosaminoglycan polysaccharide family and is a negatively charged polymer at physiological pH. It can be found in the capsule of certain bacteria but it is also found in higher vertebrates, where it serves as precursor for the natural polymers heparin and heparan sulphate. Although not proven in detail, heparosan is believed to be degraded in the lysosomes. An injection of a 100 kDa heparosan polymer labelled with Bolton-Hunter reagents has shown that heparosan is secreted as smaller fragments in body fluids/waste (US 2010/0036001).

Heparosan polymers and methods of making such polymers are described in US 2010/0036001, the content of which is incorporated herein by reference. In accordance with the present invention, the heparosan polymer may be any heparosan polymer described or disclosed in US 2010/0036001.

For use in the present invention, heparosan polymers can be produced by any suitable method, such as any of the methods described in US 2010/0036001 or US 2008/0109236. Heparosan can be produced using bacterial-derived enzymes. For example, the heparosan synthase PmHS1 of *Pasteurella multocida* Type D polymerises the heparosan sugar chain by transferring both GlcUA and GlcNAc. The *Escherichia coli* K5 enzymes KfiA (alpha GlcNAc transferase) and KfiC (beta GlcUA transferase) can together also form the disaccharide repeat of heparosan.

A heparosan polymer for use in the present invention is typically a polymer of the formula (-GlcUA-beta1,4-GlcNAc-alpha1,4-)$_n$.

The size of the heparosan polymer may be defined by the number of repeats n in this formula. The number of said repeats n may be, for example, from 2 to about 5000. The number of repeats may be, for example 50 to 2000 units, 100 to 1000 units or 200 to 700 units. The number of repeats may be 200 to 250 units, 500 to 550 units or 350 to 400 units. Any of the lower limits of these ranges may be combined with any higher upper limit of these ranges to form a suitable range of numbers of units in the heparosan polymer.

The size of the heparosan polymer may be defined by its molecular weight. The molecular weight may be the average molecular weight for a population of heparosan polymer molecules, such as the weight average molecular mass.

Molecular weight values as described herein in relation to size of the heparosan polymer may not, in practise, exactly be the size listed. Due to batch to batch variation during heparosan polymer production, some variation is to be expected. To encompass batch to batch variation, it is therefore to be understood, that a variation around +/−10%, 9%, 8%, 7%, 6%, 5%, 4%, 3%, 2% or 1% around target HEP polymer size should be expected. For example HEP polymer size of 40 kDa denotes 40 kDa+/−10%, e.g. 40 kDa could for example in practise mean 38.8 kDa, 41.5 kDa or 43.8 kDa The heparosan polymer may have a molecular weight of, for example, 500 Da to 1,000 kDa. The molecular weight of the polymer may be 500 Da to 650 kDa, 5 kDa to 750 kDa, 10 kDa to 500 kDa, 15 kDa to 550 kDa or 25 kDa to 250 kDa.

The molecular weight may be selected at particular levels within these ranges in order to achieve a suitable balance between activity of the Factor VII polypeptide and half-life or mean residence time of the conjugate. For example, the molecular weight of the polymer may be in a range selected from 15-25 kDa, 25-35 kDa, 35-45 kDa, 45-55 kDa, 55-65 kDa or 65-75 kDa.

More specific ranges of molecular weight may be selected. For example, the molecular weight may be 20 kDa to 35 kDa, such as 22 kDa to 32 kDa such as 25 kDa to 30 kDa, such as about 27 kDa. The molecular weight may be 35 to 65 kDa, such as 40 kDa to 60 kDa, such as 47 kDa to 57 kDa, such as 50 kDa to 55 kDa such as about 52 kDa. The molecular weight may be 50 to 75 kDa such as 60 to 70 kDa, such as 63 to 67 kDa such as about 65 kDa.

In particularly interesting embodiments, the heparosan polymer of the Factor VII conjugate, of the invention, has a size in a range selected from 13-65 kDa, 13-55 kDa, 25-55 kDa, 25-50 kDa, 25-45 kDa, 30-45 kDa and 38-42 kDa.

Any of the lower limits of these ranges of molecular weight may be combined with any higher upper limit from these ranges to form a suitable range for the molecular weight of the heparosan polymer in accordance with the invention.

The heparosan polymer may have a narrow size distribution (i.e. be monodisperse) or a broad size distribution (i.e. be polydisperse). The level of polydispersity (PDI) may be represented numerically based on the formula Mw/Mn, where Mw=weight average molecular mass and Mn=number average molecular weight. The polydispersity value using this equation for an ideal monodisperse polymer is 1. Preferably, a heparosan polymer for use in the present invention is monodisperse. The polymer may therefore have a polydispersity that is about 1, the polydispersity may be less than 1.25, preferably less than 1.20, preferably less than 1.15, preferably less than 1.10, preferably less than 1.09, preferably less than 1.08, preferably less than 1.07, preferably less than 1.06, preferably less than 1.05.

The molecular weight size distribution of the heparosan may be measured by comparison with monodisperse size standards (HA Lo-Ladder, Hyalose LLC) which may be run on agarose gels.

Alternatively, the size distribution of heparosan polymers may be determined by high performance size exclusion chromatography-multi angle laser light scattering (SEC-MALLS). Such a method can be used to assess the molecular weight and polydispersity of a heparosan polymer.

Figure 5B:
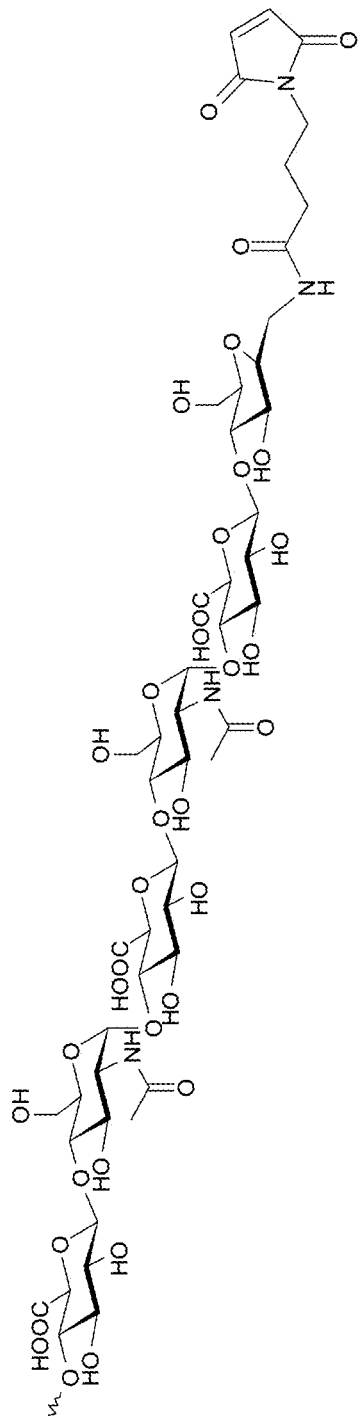
FIG. 5B shows structure of a heparosan polymer with maleimide functionality at its reducing end.
Figure 6B:
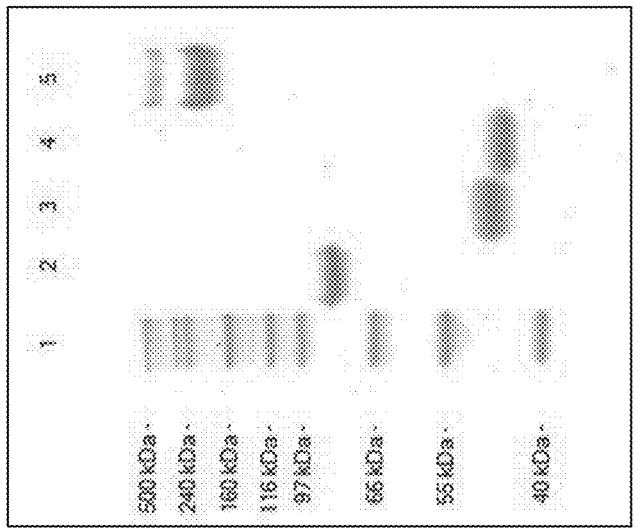
FIG. 6A and FIG. 6B show assessment of conjugate purity by SDS-PAGE.
Figure 6A:
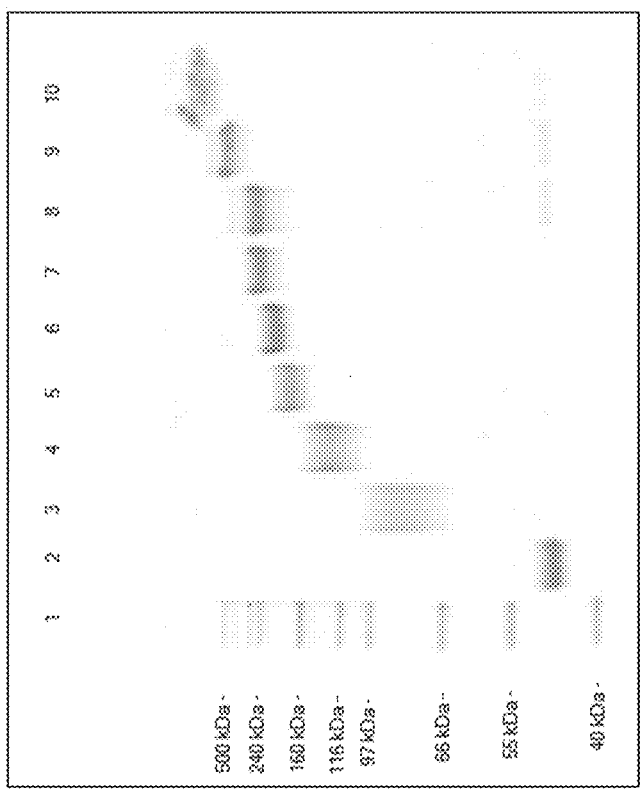
Figure 7:
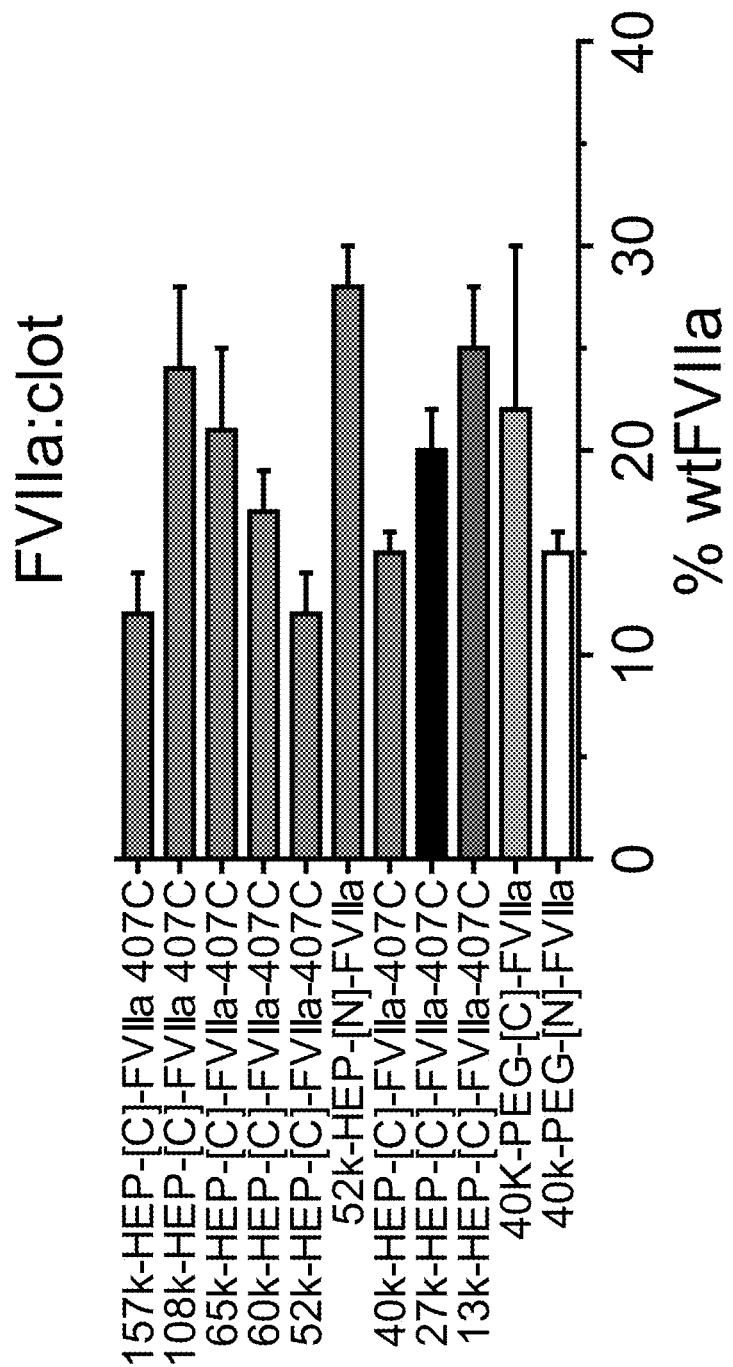
FIG. 7: Analysis of FVIIa clotting activity levels of heparosan conjugates and glycoPEGylated FVIIa references.
Figure 8:
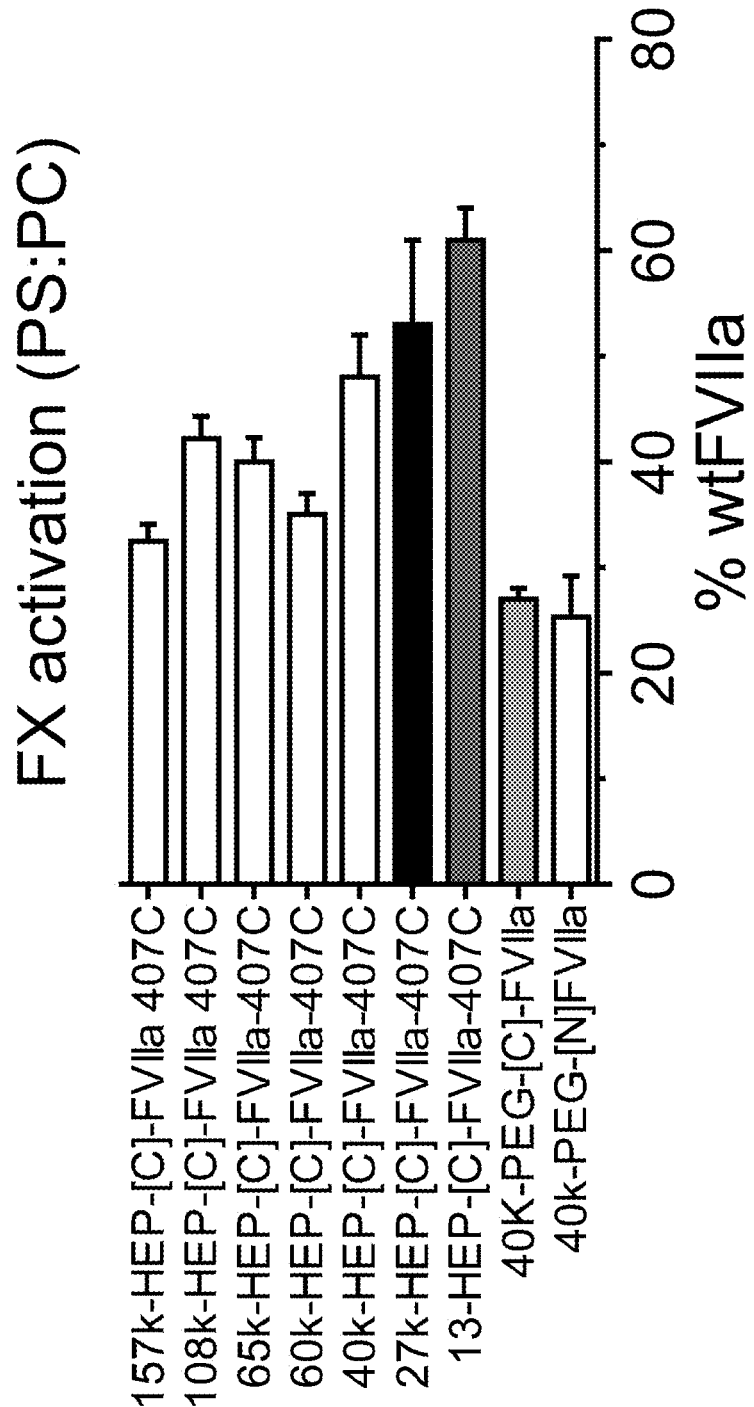
FIG. 8: Proteolytic activity of heparosan conjugates and glycoPEGylated FVIIa references.
Figure 9:
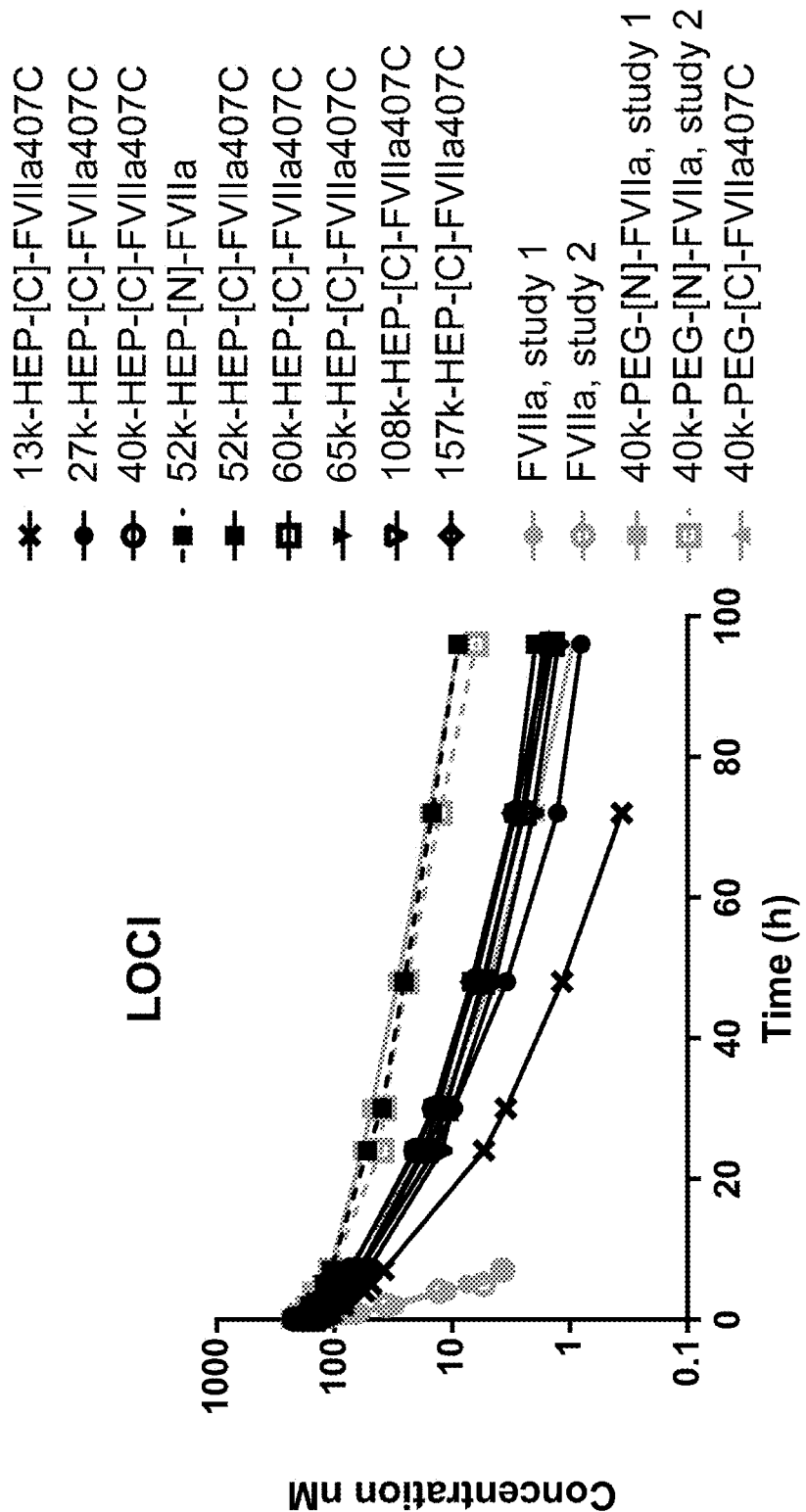
FIG. 9: PK results (LOCI) in Sprague Dawley rats. Comparison of unmodified FVIIa (2 studies), 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C, glycoconjugated 52k-HEP-[N]-FVIIa and reference molecules (40 kDa-PEG-[N]-FVIIa (2 studies) and 40 kDa-PEG-[C]-FVIIa407C). Data are shown as mean±SD (n=3-6) in a semilogarithmic plot. [N]-denotes Factor conjugates where HEParosan is attached to the N-glycan. [C]-Denotes Factor conjugates where Heparosan is attached to a cystein residue.
Figure 10:
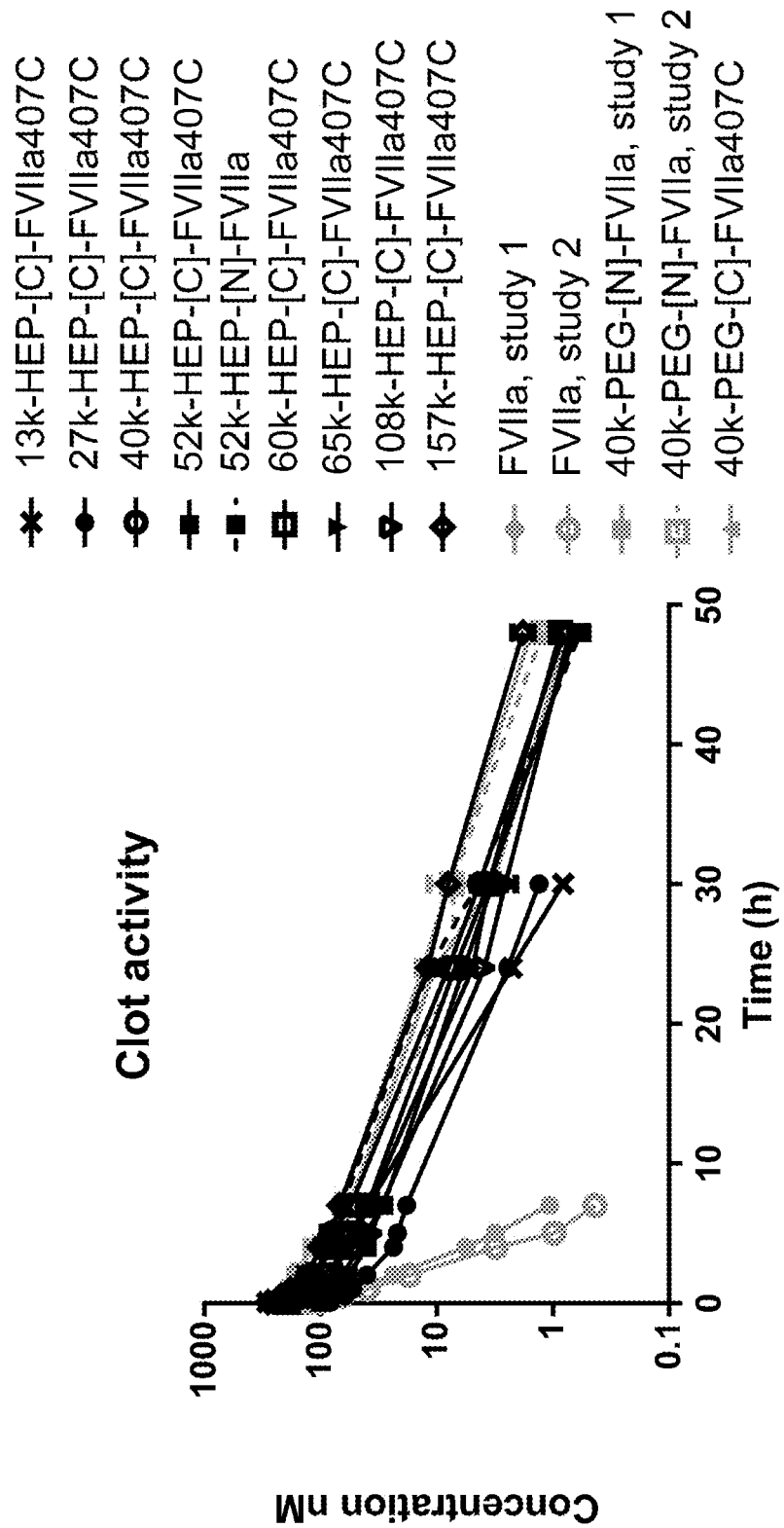
FIG. 10: PK results (Clot Activity) in Sprague Dawley rats. Comparison of unmodified FVIIa (2 studies), 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C, glycoconjugated 52k-HEP-[N]-FVIIa and reference molecules (40 kDa-PEG-[N]-FVIIa (2 studies) and 40 kDa-PEG-[C]-FVIIa407C). Data are shown in a semilogarithmic plot. [N]-denotes Factor conjugates where HEParosan is attached to the N-glycan. [C]-Denotes Factor conjugates where Heparosan is attached to a cystein residue.
Figure 11:
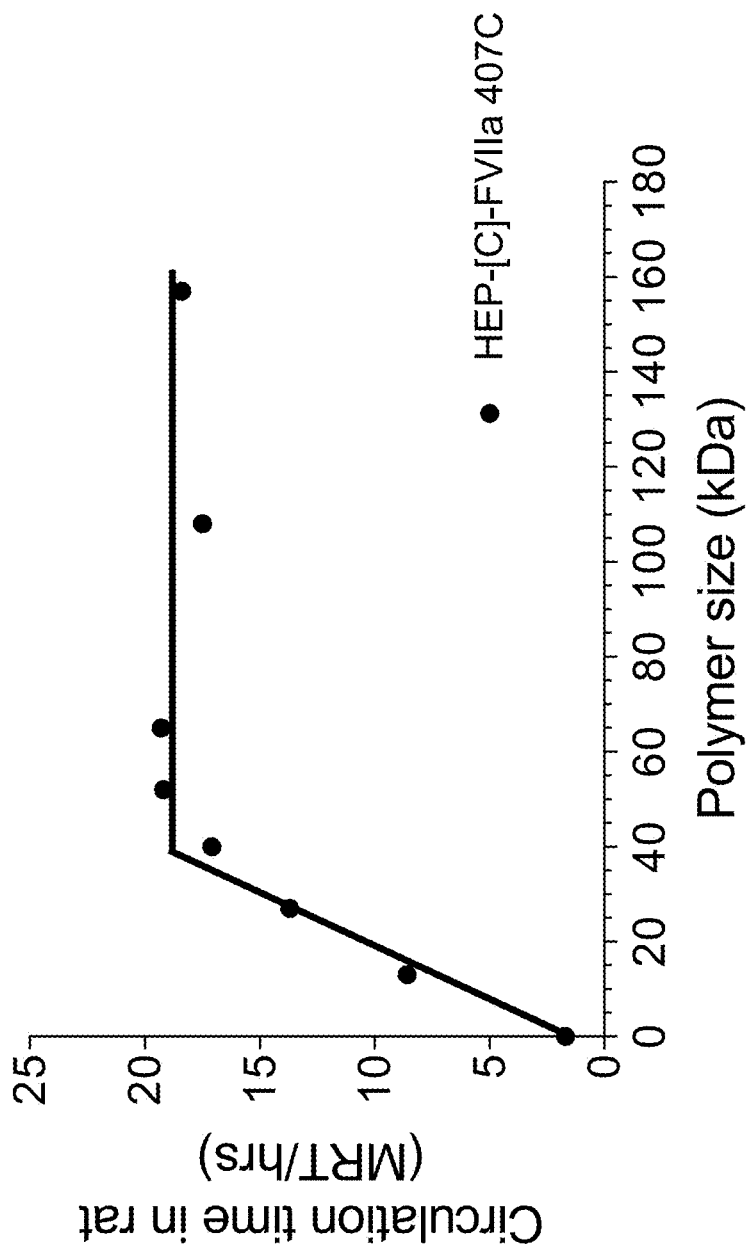
FIG. 11: Relationship between HEP-size and mean residence time (MRT) for a number of HEP-[C]-FVIIa407C conjugates. MRT values from PK studies are plotted against heparosan polymer size of conjugates. The plot represent values for non-conjugated FVIIa, 13k-HEP-[C]-FVIIa407C, 27k-HEP-[C]-FVIIa407C, 40k-HEP-[C]-FVIIa407C, 52k-HEP-[C]-FVIIa407C, 65k-HEP-[C]-FVIIa407C, 108k-HEP-[C]-FVIIa407C and 157k-HEP-[C]-FVIIa407C. MRT (LOCI) was calculated by non-compartmental methods using Phoenix WinNonlin 6.0 (Pharsight Corporation). [N]-denotes Factor conjugates where HEParosan is attached to the N-glycan. [C]-Denotes Factor conjugates where Heparosan is attached to a cystein residue.

Polymer size may be regulated in enzymatic methods of production. By controlling the molar ratio of heparosan acceptor chains to UDP sugar, it is possible to select a final heparosan polymer size that is desired The heparosan polymer may further comprise a reactive group to allow its attachment to a Factor VII polypeptide. A suitable reactive group may be, for example, an aldehyde, alkyne, ketone, maleimide, thiol, azide, amino, hydrazide, hydroxylamine, carbonate ester, chelator or a combination of any thereof. For example, FIG. 5B illustrates a heparosan polymer comprising a maleimide group.

As set out in the Examples, maleimide or aldehyde functionalized heparosan polymers of defined size may be prepared by an enzymatic (PmHS1) polymerization reaction using the two sugar nucleotides UDP-GlcNAc and UDP-GlcUA in equimolar amount. A priming trisaccharide (GlcUA-GlcNAc-GlcUA)NH$_2$ may be used for initiating the reaction, and polymerization run until depletion of sugar nucleotide building blocks. Terminal amine (originating from the primer) may then be functionalized with suitable reactive groups such as a reactive group as described above, such as a maleimide functionality for conjugation to free cysteines or aldehydes for reductive amination to amino groups. The size of the heparosan polymers can be pre-determined by variation in sugar nucleotide: primer stoichiometry. The technique is described in detail in US 2010/0036001.

The reactive group may be present at the reducing or non-reducing termini or throughout the sugar chain. The presence of only one such reactive group is preferred when conjugating the heparosan polymer to the polypeptide.

Methods for Preparing FVII-HEP Conjugates

For example, WO 03/031464 describes methods for remodelling the glycan structure of a polypeptide, such as a Factor VII or Factor VIIa polypeptide and methods for the addition of a modifying group such as a water soluble polymer to such a polypeptide. Such methods may be used to attach a heparosan polymer to a Factor VII polypeptide in accordance with the present invention.

As set out in the Examples, a Factor VII polypeptide may be conjugated to its glycan moieties using sialyltransferase. For enablement of this approach, a HEP polymer first need to be linked to a sialic acid cytidine monophosphate. Glycylsialic acid cytidine monophosphate (GSC) is a suitable starting point for such chemistry, but other sialic acid cytidine monophosphate or fragments of such can be used. Examples set out methods for covalent linking HEP polymers to GSC molecules. By covalent attachment, a HEP-GSC (HEP conjugated glycylsialic acid cytidine monophosphate) molecule is created that can be transferred to glycan moieties of FVIIa.

Factor VII-heparosan conjugates may be purified once they have been produced. For example, purification may comprise affinity chromatography using immobilised mAb directed towards the Factor VII polypeptide, such as mAb directed against the calcified gla-domain on FVIIa. In such an affinity chromatography method, unconjugated HEP-polymer may be removed by extensive washing of the column. FVII may be released from the column by releasing the FVII from the antibody. For example, where the antibody is specific to the calcified gla-domain, release from the column may be achieved by washing with a buffer comprising EDTA.

Size exclusion chromatography may be used to separate Factor VII-heparosan conjugates from unconjugated Factor VII.

Pure conjugate may be concentrated by ultrafiltration.

Final concentrations of Factor VII-heparosan conjugate resulting from a process of production may be determined by, for example, HPLC quantification, such as HPLC quantification of the FVII light chain.

In connection with the present invention, it is shown that it is possible to link a carbohydrate polymer such as HEP via a maleimido group to a thio-modified GSC molecule and transfer the reagent to an intact glycosyl group on a glycoprotein by means of a sialyltransferase, thereby creating a linkage that contains a cyclic succinimide group.

Succinimide based linkages, however, may undergo hydrolytic ring opening when the conjugate is stored in aqueous solution for extended time periods (Bioconjugation Techniques, G. T. Hermanson, Academic Press, 3rd edition 2013 p. 309) and while the linkage may remain intact, the ring opening reaction will add undesirable heterogeneity in form of regio- and stereo-isomers to the final conjugate.

It follows from the above that it is preferable to link the half-life extending moiety to the glycoprotein in such a way that 1) the glycan residue of the glycoprotein is preserved in intact form, and 2) no heterogenicity is present in the linker part between the intact glycosyl residue and the half-life extending moiety.

There is a need in the art for methods of conjugating two compounds, such as a half-life extending moiety such as HEP to a protein or protein glycan, wherein the compounds are linked such that a stable and isomer free conjugate is obtained.

In one aspect the present invention provides a stable and isomer free linker for use in glycylsialic acid cytidine monophosphate (GSC) based conjugation of HEP to FVII. The GSC starting material used in the current invention can be synthesised chemically (Dufner, G. Eur. J. Org. Chem. 2000, 1467-1482) or it can be obtained by chemoenzymatic routes as described in WO07056191. The GSC structure is shown below:

GSC

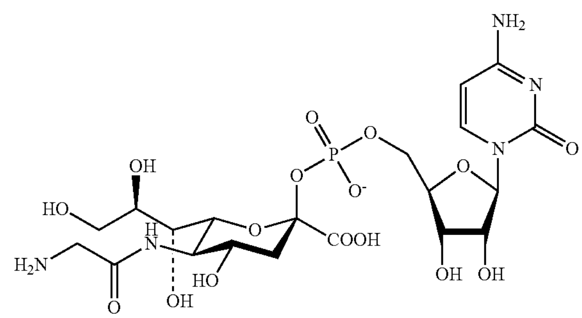

In one embodiment conjugates according to the present invention comprise a linker comprising the following structure:

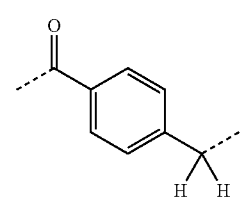

hereinafter also referred to as sublinker or sublinkage—that connects a HEP-amine and GSC in one of the following ways:

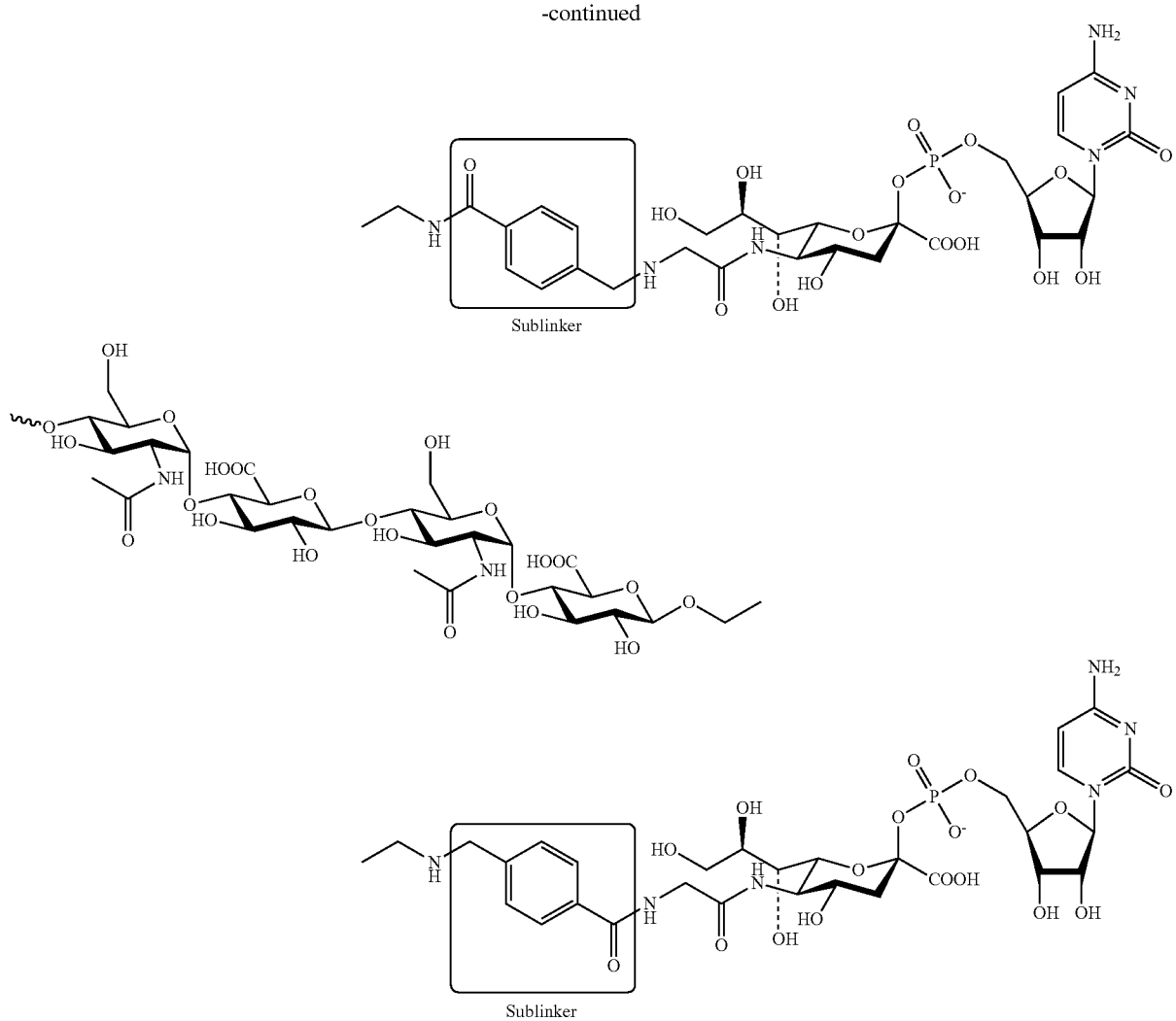

The highlighted 4-methylbenzoyl sublinker thus makes up part of the full linking structure linking the half-life extending moiety to a target protein. The sublinker is as such a stable structure compared to alternatives, such as succinimide based linkers (prepared from maleimide reactions with sulfhydryl groups) since the latter type of cyclic linkage has a tendency to undergo hydrolytic ring opening when the conjugate is stored in aqueous solution for extended time periods (Bioconjugation Techniques, G. T. Hermanson, Academic Press, 3$^{rd}$ edition 2013 p. 309). Even though the linkage in this case (e.g. between HEP and sialic acid on a glycoprotein) may remain intact, the ring opening reaction will add heterogeneity in form of regio- and stereo-isomers to the final conjugate composition.

One advantage associated with conjugates according to the present invention is thus that a homogenous composition is obtained, i.e. that the tendency of isomer formation due to linker structure and stability is significantly reduced. Another advantage is that the linker and conjugates according to the invention can be produced in a simple process, preferably a one-step process.

Isomers are undesirable since these can lead to a heterogeneous product and increase the risk for unwanted immune responses in humans.

The 4-methylbenzoyl sublinkage as used in the present invention between HEP and GSC is not able to form sterio- or regio isomers. HEP polymers can as mentioned earlier be prepared by a synchronised enzymatic polymerisation reaction (US 20100036001). This method use heparan synthetase I from *Pasturella multocida* (PmHS1) which can be expressed in *E. coli* as a maltose binding protein fusion constructs. Purified MBP-PmHS1 is able to produce monodisperse polymers in a synchronized, stoichiometrically controlled reaction, when it is added to an equimolar mixture of sugar nucleotides (GlcNAc-UDP and GlcUA-UDP). A trisaccharide initiator (GlcUA-GlcNAc-GlcUA) is used to prime the reaction, and polymer length is determined by the primer: sugar nucleotide ratios. The polymerization reaction will run until about 90% of the sugar nucleotides are consumed. Polymers are isolated from the reaction mixture by anion exchange chromatography, and subsequently freeze-dried into stable powder.

Processes for preparation of functional HEP polymers are described in US 20100036001 which for example lists aldehyde-, amine- and maleimide functionalized HEP reagents. US 20100036001 is hereby incorporated by reference in its entirety as if fully set forth herein. A range of other functionally modified HEP derivatives are available using similar chemistry. HEP polymers used in certain embodiments of the present invention are initially produced with a primary amine handle at the reducing terminal according to methods described in US20100036001.

Amine functionalized HEP polymers (i.e. HEP having an amine-handle) prepared according US20100036001 can be converted into a HEP-benzaldehyde by reaction with N-succinimidyl 4-formylbenzoate and subsequently coupled to the glycylamino group of GSC by a reductive amination reaction. The resulting HEP-GSC product can subsequently be enzymatically conjugated to a glycoprotein using a sialyltransferase.

For example, said amine handle on HEP can be converted into a benzaldehyde functionality by reaction with N-succinimidyl 4-formylbenzoate according to the below scheme:

For example, GSC can be reacted under pH neutral conditions with N-succinimidyl 4-formylbenzoate to provide a GSC compound that contains a reactive aldehyde group (see for example WO2011101267). The aldehyde derivatized GSC compound (GSC-benzaldehyde) can then be reacted with HEP-amine and reducing agent to form a HEP-GSC reagent.

Figure 13:
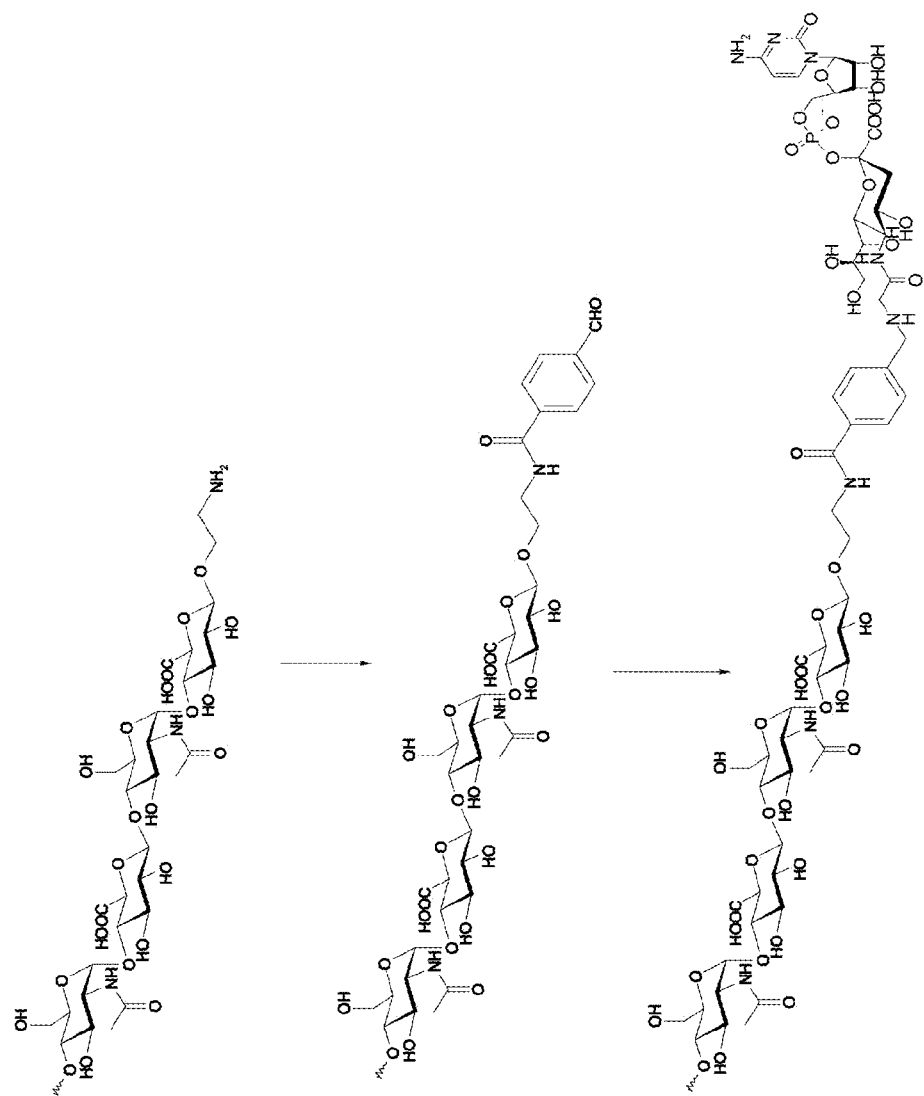
FIG. 13: Functionalization of heparosan (HEP) polymer with a benzaldehyde group and subsequent reaction with glycylsialic acid cytidine monophosphate (GSC) in a reductive amination reaction.
Figure 14:
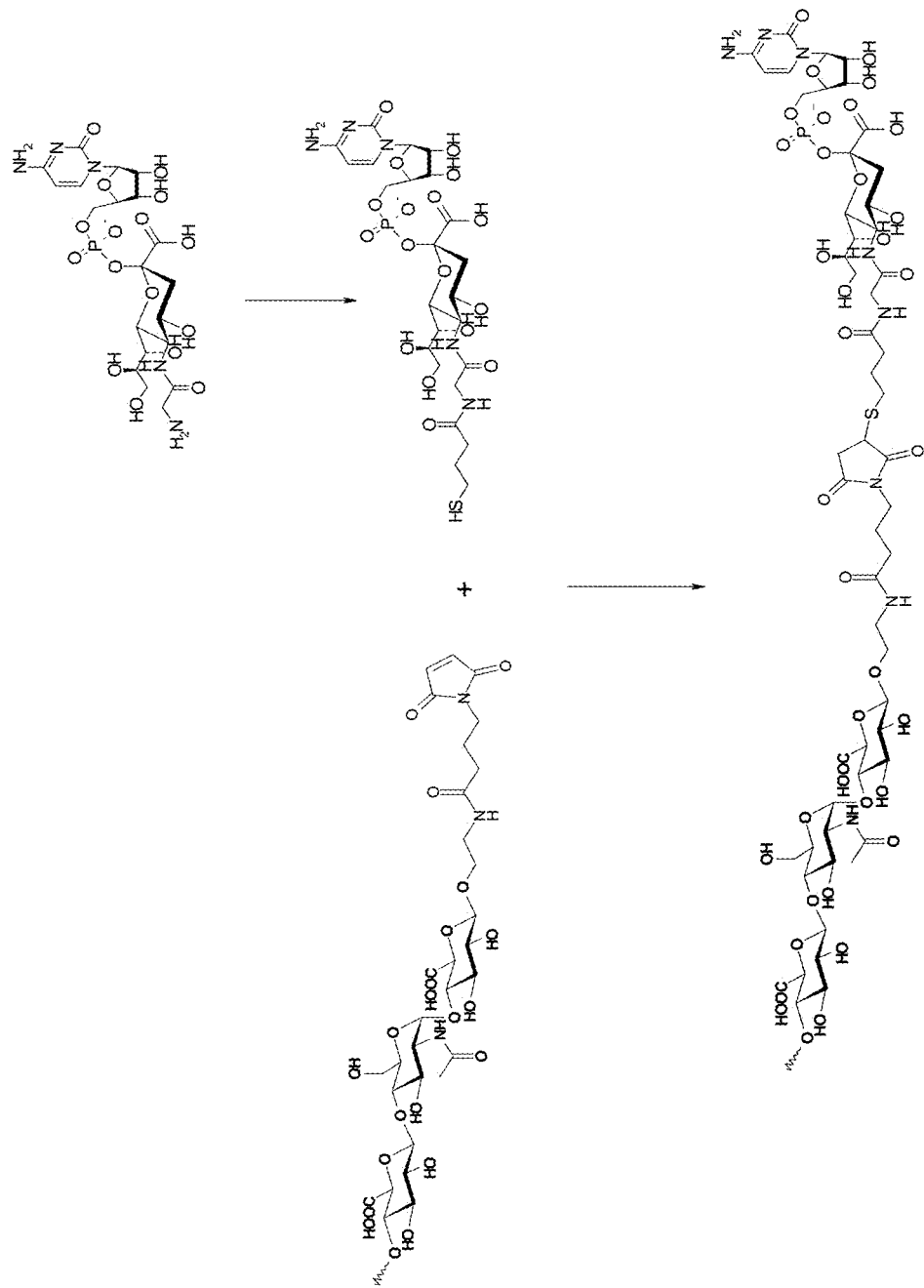
FIG. 14: Functionalization of glycylsialic acid cytidine monophosphate (GSC) with a thio group and subsequent reaction with a maleimide functionalized heparosan (HEP) polymer.

The above mentioned reaction may be reversed, so that the HEP-amine is first reacted with N-succinimidyl 4-formylbenzoate to form an aldehyde derivatized HEP-polymer, which subsequently is reacted directly with GSC in the presence of a reducing agent. In practice this eliminates the tedious chromatographic handling of GSC-CHO. This route of synthesis is depicted in FIG. 13.

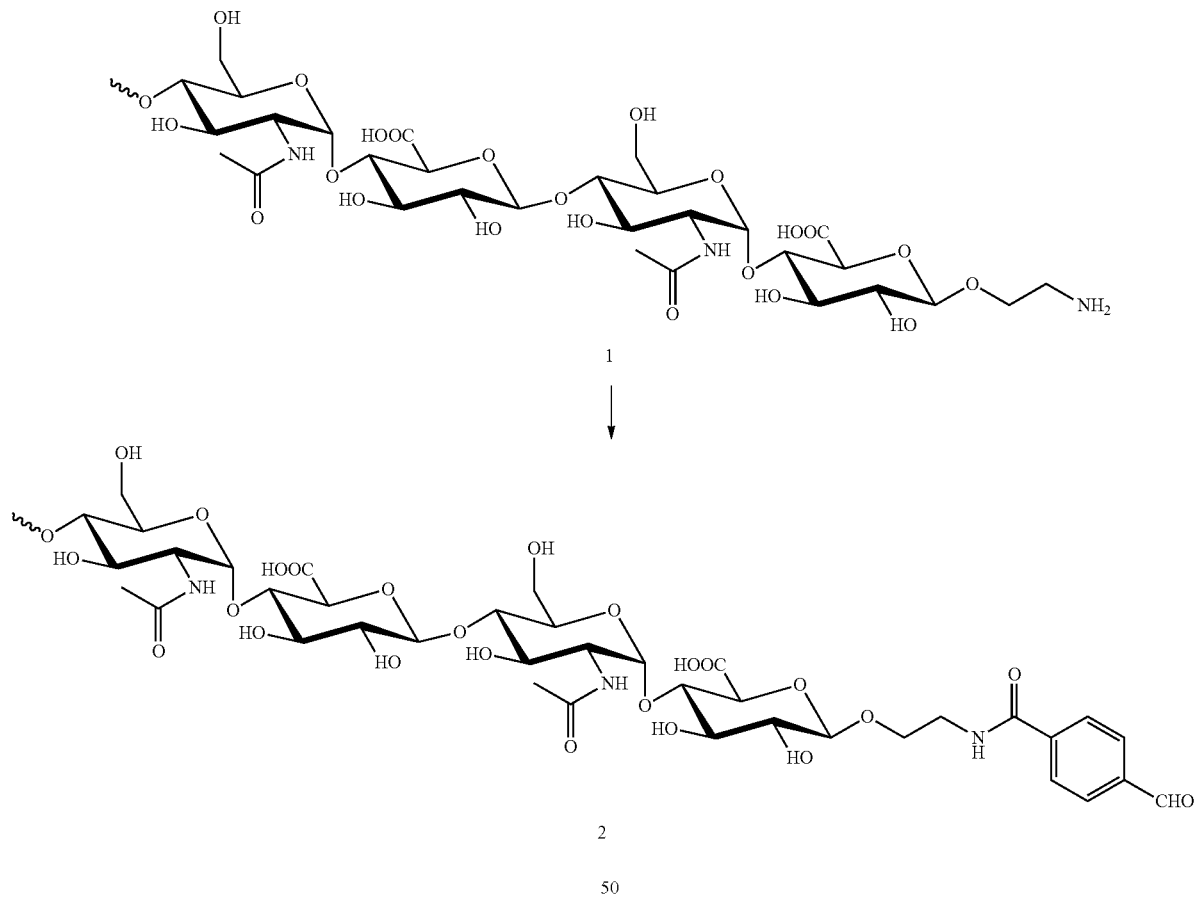

The conversion of HEP amine (1) to the 4-formylbenzamide compound (2) in the above scheme may be carried out by reaction with acyl activated forms of 4-formylbenzoic acid.

N-succinimidyl may be chosen as acyl activation group but a number of other acyl activation groups are known to the skilled person. Non-limited examples include 1-hydroxy-7-azabenzotriazole-, 1-hydroxy-benzotriazole-, pentafluorophenyl-esters as know from peptide chemistry.

Figure 12:
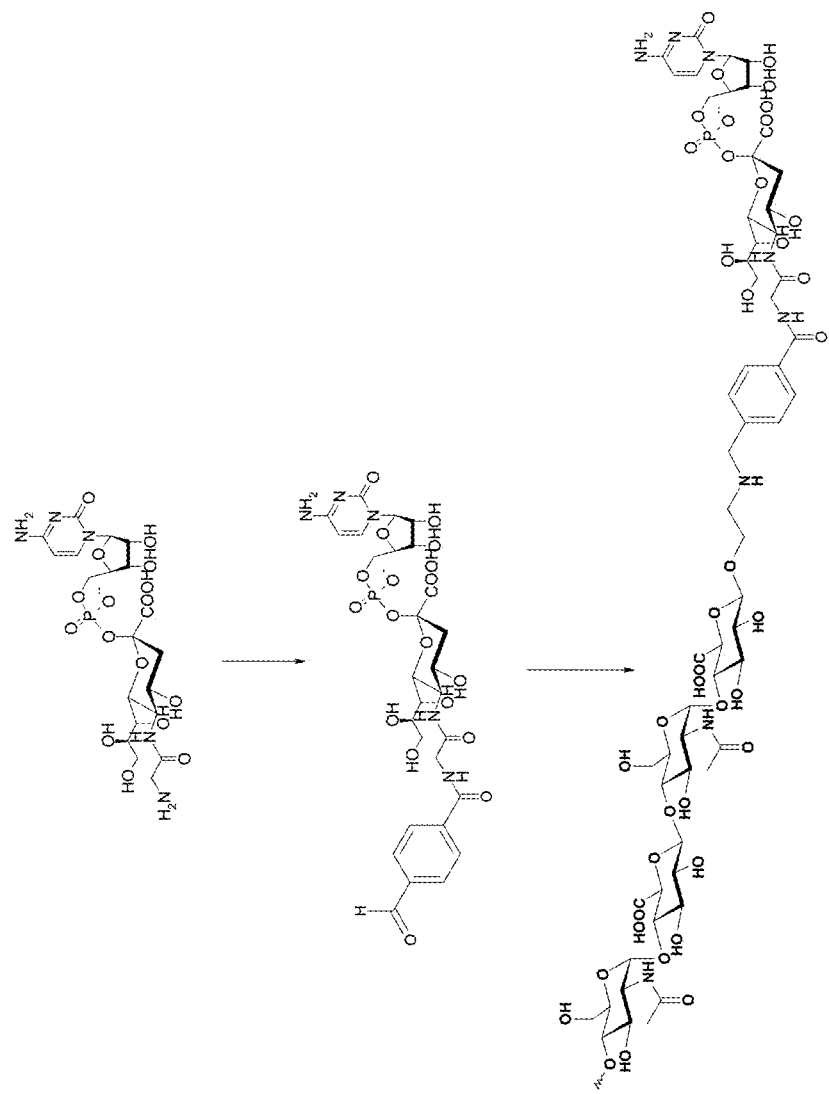
FIG. 12 Functionalization of glycylsialic acid cytidine monophosphate (GSC) with a benzaldehyde group. GSC is acylated with 4-formylbenzoic acid and subsequently reacted with heparosan (HEP)-amine by a reductive animation reaction.

HEP reagents modified with a benzaldehyde functionality can be kept stable for extended time periods when stored frozen (−80° C.) in dry form. Alternatively, a benzaldehyde moiety can be attached to the GSC compound, thereby resulting in a GSC-benzaldehyde compound suitable for conjugation to an amine functionalized half-life extending moiety. This route of synthesis is depicted in FIG. 12.

Thus, in one embodiment of the present invention HEP-benzaldehyde is coupled to GSC by reductive amination.

Reductive amination is a two-step reaction which proceeds as follows: Initially an imine (also known as Schiff-base) is formed between the aldehyde component and the amine component (in the present embodiment the glycyl amino group of GSC). The imine is then reduced to an amine in the second step. The reducing agent is chosen so that it selectively reduces the formed imine to an amine derivative.

A number of suitable reducing reagents are available to the skilled person. Non-limiting examples include sodium cyanoborohydride (NaBH3CN), sodium borohydride (NaBH4), pyridin boran complex (BH3:Py), dimethylsulfide boran complex (Me2S:BH3) and picoline boran complex.

Although reductive amination to the reducing end of carbohydrates (for example to the reducing termini of HEP polymers) is possible, it has generally been described as a slow and inefficient reaction (JC. Gildersleeve, Bioconjug Chem. 2008 Jul. 19(7): 1485-1490). Side reactions, such as the Amadori reaction, where the initially formed imine rearrange to a keto amine are also possible, and will lead to heterogenicity which as previously discussed is undesirable in the present context.

Aromatic aldehydes such as benzaldehydes derivatives are not able to form such rearrangement reactions as the imine is unable to enolize and also lack the required neighbouring hydroxy group typically found in carbohydrate derived imines. Aromatic aldehydes such as benzaldehydes derivatives are therefore particular useful in reductive amination reactions for generating isomer free HEP-GSC reagent.

A surplus of GSC and reducing reagent is optionally used in order to drive reductive amination chemistry fast to completion. When the reaction is completed, the excess (non-reacted) GSC reagent and other small molecular components such as excess reducing reagent can subsequently be removed by dialysis, tangential flow filtration or size exclusion chromatography.

Both the natural substrate for sialyltransferases, Sia-CMP, and the GSC derivatives are multifunctional molecules that are charged and highly hydrophilic. In addition, they are not stable in solution for extended time periods especially if pH is below 6.0. At such low pH, the CMP activation group necessary for substrate transfer is lost due to acid catalyzed phosphate diester hydrolysis. Selective modification and isolation of GSC and Sia-CMP derivatives thus require careful control of pH, as well as fast and efficient isolation methods, in order to avoid CMP-hydrolysis.

In the present invention, large half-life extending moieties are conjugated to GSC using reductive amination chemistry. Arylaldehydes, such as benzaldehyde modified half-life extending moieties have been found optimal for this type of modification, as they efficiently can react with GSC under reductive amination conditions.

As GSC may undergo hydrolysis in acid media, it is important to maintain a near neutral or slightly basic environment during the coupling to HEP-benzaldehydes. HEP polymers and GSC are both highly water soluble and aqueous buffer systems are therefore preferable for maintaining pH at a near neutral level. A number of both organic and inorganic buffers may be used, however, the buffer components should preferably not be reactive under reductive amination conditions. This exclude for instance organic buffer systems containing primary and—to lesser extend—secondary amino groups. The skilled person will know which buffers are suitable and which are not. Some examples of suitable buffers are shown in table 1 below:

TABLE 1

Buffers

| Common Name | pKa at 25° C. | Buffer Range | Full Compound Name |
|---|---|---|---|
| Bicine | 8.35 | 7.6-9.0 | N,N-bis(2-hydroxyethyl)glycine |
| Hepes | 7.48 | 6.8-8.2 | 4-2-hydroxyethyl-1-piperazineethanesulfonic acid |
| TES | 7.40 | 6.8-8.2 | 2-{[tris(hydroxy-methyl)methyl]amino}ethanesulfonic acid |
| MOPS | 7.20 | 6.5-7.9 | 3-(N-morpholino)propanesulfonic acid |
| PIPES | 6.76 | 6.1-7.5 | piperazine-N,N'-bis(2-ethanesulfonic acid) |
| MES | 6.15 | 5.5-6.7 | 2-(N-morpholino)ethanesulfonic acid |

By applying this method, GSC reagents modified with half-life extending moieties, having isomer free stable linkages can efficient be prepared, and isolated in a simple process that minimize the chance for hydrolysis of the CMP activation group.

By reacting either of said compounds with each other a HEP-GSC conjugate comprising a 4-methylbenzoyl sublinker moiety may be created.

Figure 15:
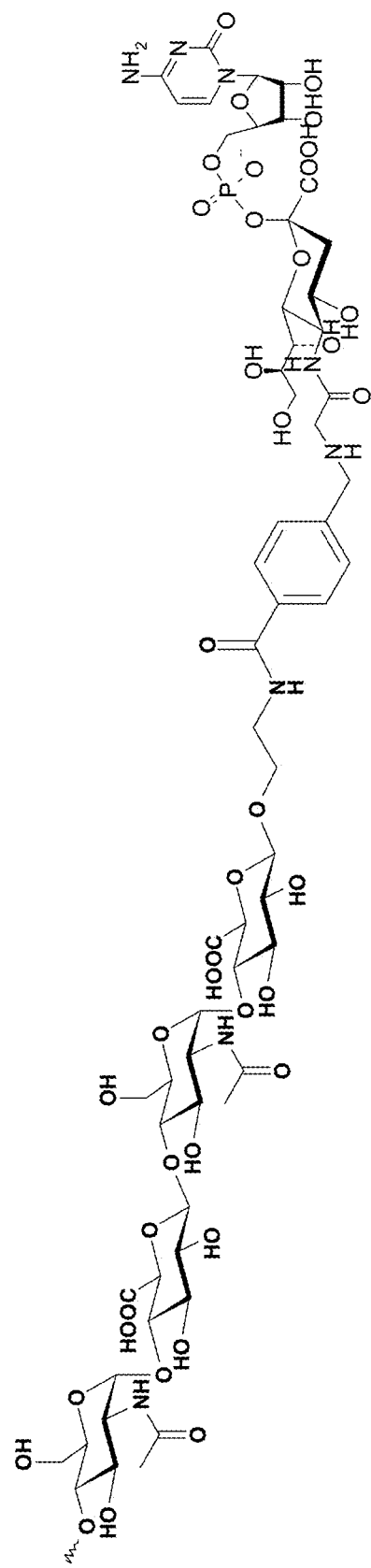
FIG. 15: Heparosan (HEP)—glycylsialic acid cytidine monophosphate (GSC).
Figure 16:
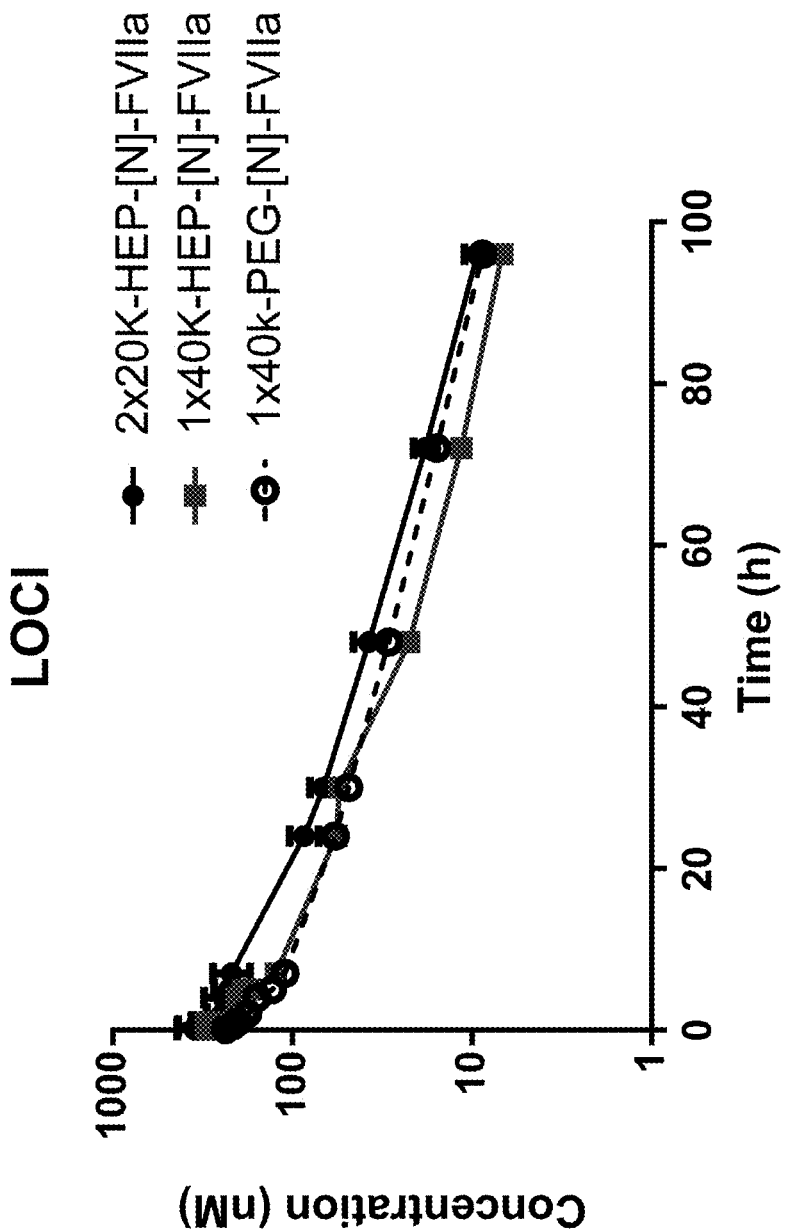
FIG. 16: PK results (LOCI) in Sprague Dawley rats. Comparison of 2×20K-HEP-[N]-FVIIa; 1×40K-HEP-[N]-FVIIa and 1×40k-PEG-[N]-FVIIa in a semilogarithmic plot. Data are shown as mean±SD (n=3-6).
Figure 17:
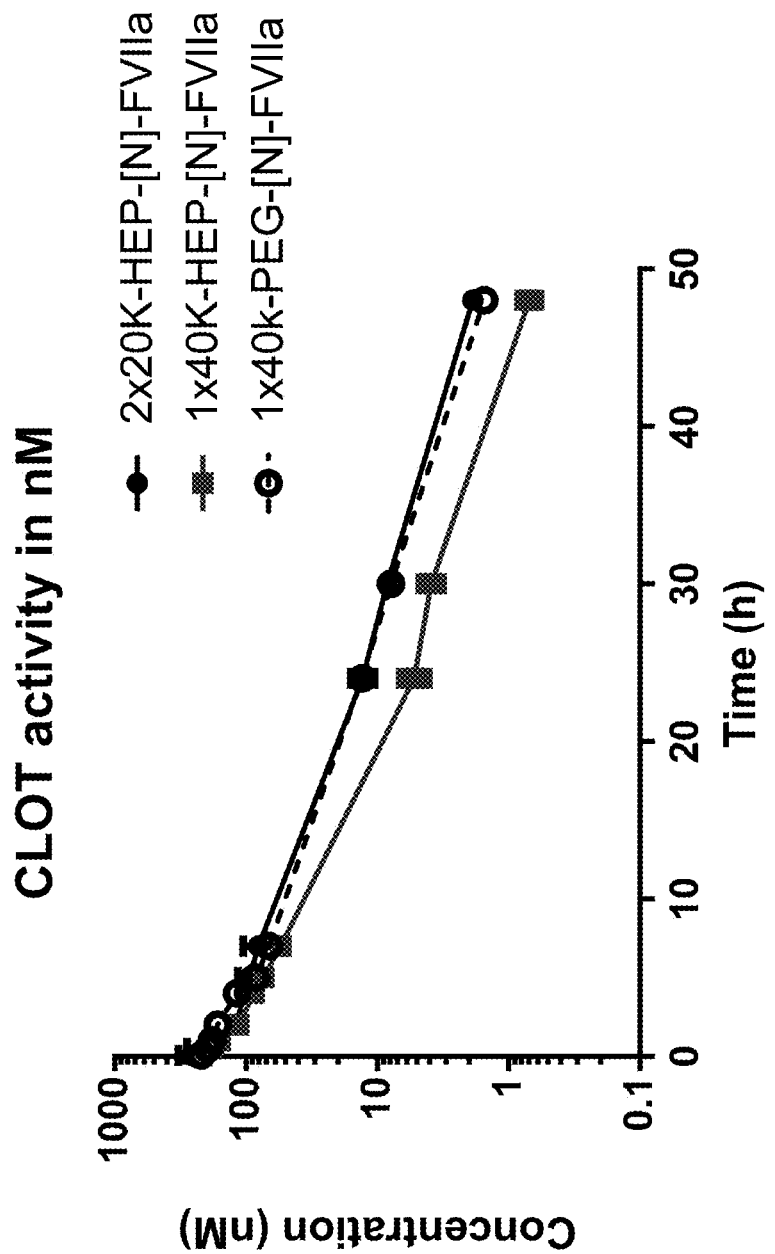
FIG. 17: PK results (Clot Activity) in Sprague Dawley rats. Comparison of 2×20K-HEP-[N]-FVIIa; 1×40K-HEP-[N]-FVIIa and 1×40k-PEG-[N]-FVIIa in a semilogarithmic plot.

GSC may also be reacted with thiobutyrolactone, thereby creating a thiol modified GSC molecule (GSC-SH). As demonstrated in the present invention, such reagents may be reacted with maleimide functionalized HEP polymers to form HEP-GSC reagents. This synthesis route is depicted in FIG. 15. The resulting product has a linkage structure comprising succinimide.

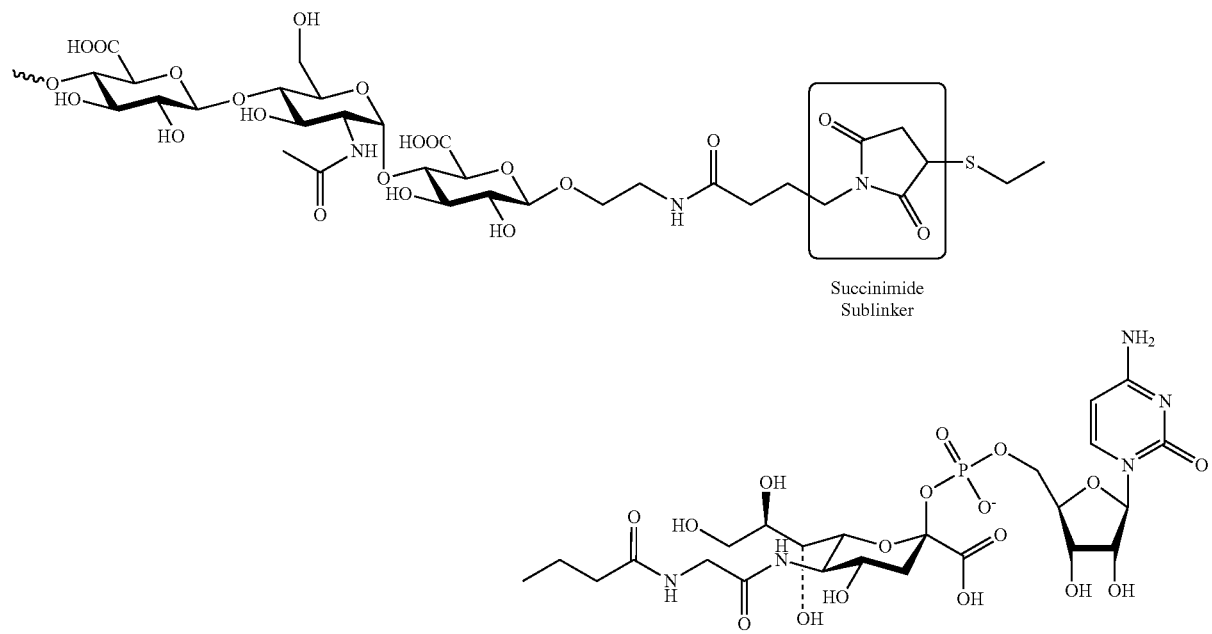

Succinimide Sublinker

However, succinimide based (sub)linkages may undergo hydrolytic ring opening inter alia when the modified GSC reagent is stored in aqueous solution for extended time periods and while the linkage may remain intact, the ring opening reaction will add undesirable heterogeneity in form of regio- and stereo-isomers.

Methods of Glycoconjugation

Conjugation of a HEP-GSC conjugate with a (poly)-peptide may be carried out via a glycan present on residues in the (poly)-peptide backbone. This form of conjugation is also referred to as glycoconjugation.

Methods based on sialyltransferase have over the years proven to be mild and highly selective for modifying N-glycans or O-glycans on blood coagulation factors, such as coagulation factor FVII.

In contrast to conjugation methods based on cysteine alkylations, lysine acylations and similar conjugations involving amino acids in the protein backbone, conjugation via glycans is an appealing way of attaching larger structures such as polymers of protein/peptide fragments to bioactive proteins with less disturbance of bioactivity. This is because glycans being highly hydrophilic generally tend to be oriented away from the protein surface and out in solution, leaving the binding surfaces that are important for the proteins activity free.

The glycan may be naturally occurring or it may be inserted via e.g. insertion of an N-linked glycan using methods well known in the art.

GSC is a sialic acid derivative that can be transferred to glycoproteins by the use of sialyltransferases. It can be selectively modified with substituents such as PEG on the glycyl amino group and still be enzymatically transferred to glycoproteins by use of sialyltransferases. GSC can be efficiently prepared by an enzymatic process in large scale (WO07056191).

Sialyltransferases

Sialyltransferases are a class of glycosyltransferases that transfer sialic acid from naturally activated sialic acid (Sia)—CMP (cytidine monophosphate) compounds to galactosyl-moieties on e.g. proteins. Many sialyltransferases (ST3GalIII, ST3GalI, ST6GalNAcI) are capable of transfer of sialic acid—CMP (Sia-CMP) derivatives that have been modified on the C5 acetamido group inter alia with large groups such as 40 kDa PEG (WO03031464). An extensive, but non-limited list of relevant sialyltransferases that can be used with the current invention is disclosed in WO2006094810, which is hereby incorporated by reference in its entirety.

Figure 18:
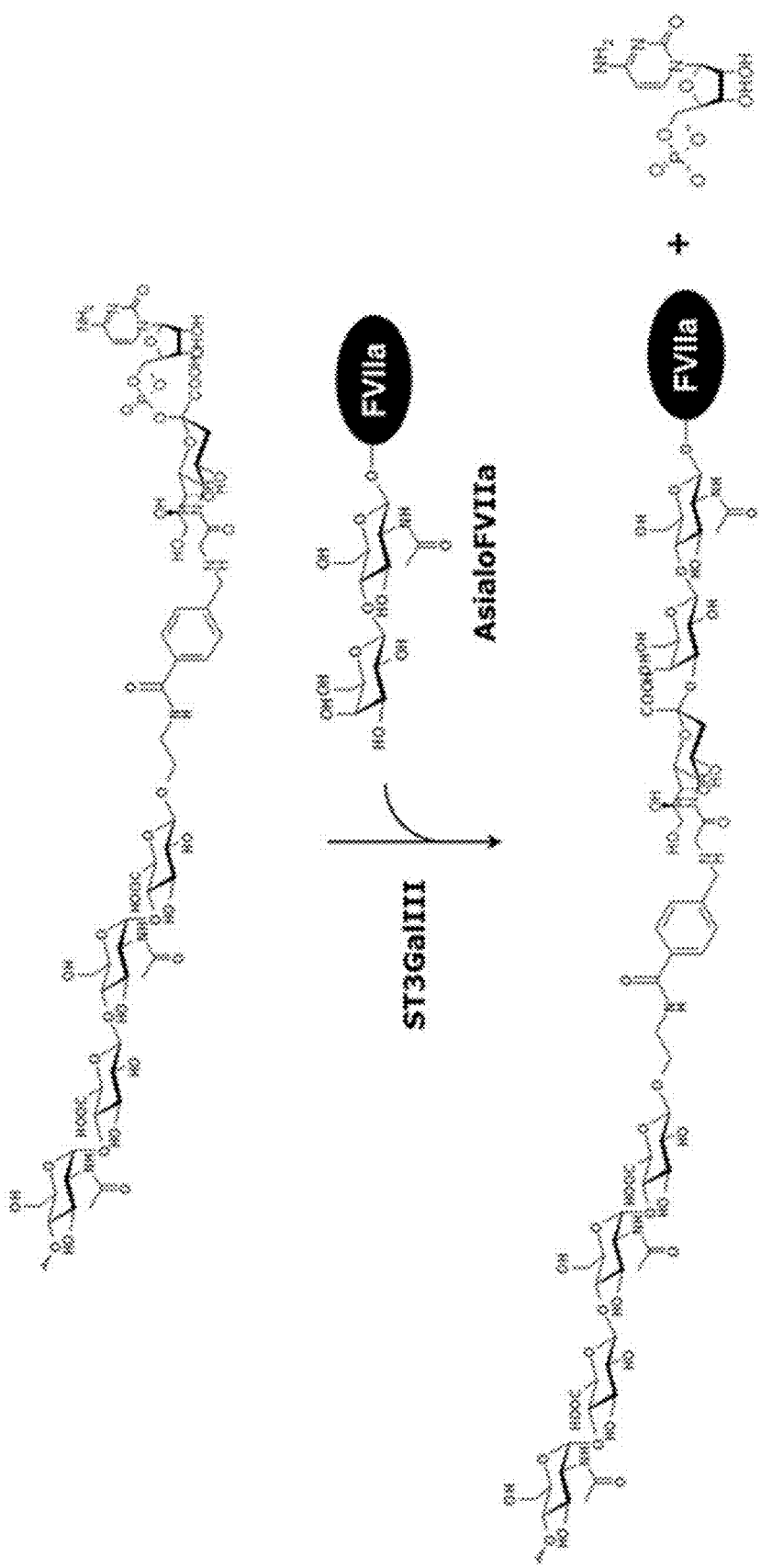
FIG. 18: Reaction scheme wherein an asialoFVIIa glycoprotein is reacted with HEP-GSC in the presence of a ST3GalIII sialyltransferase.

In one aspect of the present invention, terminal sialic acids on glycoproteins can be removed by sialidase treatment to provide asialo glycoproteins. Asialo glycoproteins and GSC modified with the half-life extending moiety together will act as substrates for sialyltransferases. The product of the reaction is a glycoprotein conjugate having the half-life extending moiety linked via an intact glycosyl linking group—in this case an intact sialic acid linker group. A reaction scheme wherein an asialo FVIIa glycoprotein is reacted with HEP-GSC in the presence of sialyltransferase is shown in FIG. 18.

The term "sialic acid" refers to any member of a family of nine-carbon carboxylated sugars. The most common member of the sialic acid family is N-acetylneuraminic acid (2-keto-5-acetamido-3,5-dideoxy-D-glycero-D-galactononulopyranos-1-onic acid (often abbreviated as Neu5Ac, NeuAc, NeuNAc, or NANA). A second member of the family is N-glycolyl-neuraminic acid (Neu5Gc or NeuGc), in which the N-acetyl group of NeuNAc is hydroxylated. A third sialic acid family member is 2-keto-3-deoxy-nonulosonic acid (KDN) (Nadano et al. (1986) J. Biol. Chem. 261: 11550-11557; Kanamori et al., J. Biol. Chem. 265: 21811-21819 (1990)). Also included are 9-substituted sialic acids such as a 9-O-C1-C6 acyl-Neu5Ac like 9-O-lactylNeu5Ac or 9-O-acetyl-Neu5Ac. The synthesis and use of sialic acid compounds in a sialylation procedure is disclosed in international application WO92/16640, published Oct. 1, 1992.

The term "sialic acid derivative" refers to sialic acids as defined above that are modified with one or more chemical moieties. The modifying group may for example be alkyl groups such as methyl groups, azido- and fluoro groups, or functional groups such as amino or thiol groups that can function as handles for attaching other chemical moieties. Examples include 9-deoxy-9-fluoro-Neu5Ac and 9-azido-9-deoxy-Neu5Ac. The term also encompasses sialic acids that lack one of more functional groups such as the carboxyl group or one or more of the hydroxyl groups. Derivatives where the carboxyl group is replaced with a carboxamide group or an ester group are also encompassed by the term. The term also refers to sialic acids where one or more hydroxyl groups have been oxidized to carbonyl groups. Furthermore the term refers to sialic acids that lack the C9 carbon atom or both the C9-C8 carbon chain for example after oxidative treatment with periodate.

Glycyl sialic acid is a sialic acid derivative according to the definition above, where the N-acetyl group of NeuNAc is replaced with a glycyl group also known as an amino acetyl group. Glycyl sialic acid may be represented with the following structure:

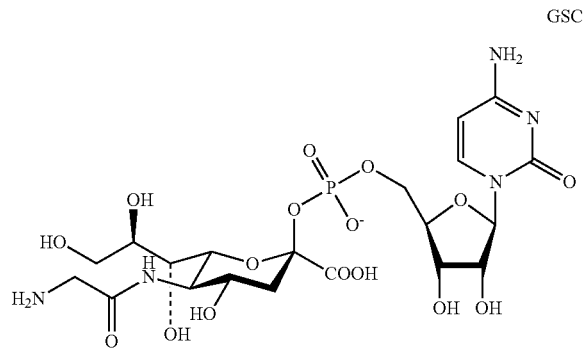

The term "CMP-activated" sialic acid or sialic acid derivatives refer to a sugar nucleotide containing a sialic acid moiety and a cytidine monophosphate (CMP).

In the present description, the term "glycyl sialic acid cytidine monophosphate" is used for describing GSC, and is a synonym for alternative naming of same CMP activated glycyl sialic acid. Alternative naming include CMP-5'-glycyl sialic acid, cytidine-5'-monophospho-N-glycylneuraminic acid, cytidine-5'-monophospho-N-glycyl sialic acid.

The term "intact glycosyl linking group" refers to a linking group that is derived from a glycosyl moiety in which the saccharide monomer interposed between and covalently attached to the polypeptide and the HEP moiety is not degraded, e.g., oxidized, e.g., by sodium metaperiodate during conjugate formation. "Intact glycosyl linking groups" may be derived from a naturally occurring oligosaccharide by addition of glycosyl unites or removal of one or more glycosyl unit from a parent saccharide structure.

The term "asialo glycoprotein" is intended to include glycoproteins wherein one or more terminal sialic acid residues have been removed, e.g., by treatment with a sialidase or by chemical treatment, exposing at least one galactose or N-acetylgalactosamine residue from the underlying "layer" of galactose or N-acetylgalactosamine ("exposed galactose residue").

Dotted lines in structure formulas denotes open valence bond (i.e. bonds that connect the structures to other chemical moieties).

PEGylated Derivatives

"PEGylated Factor VII polypeptide variants/derivatives" according to the present invention may have one or more polyethylene glycol (PEG) molecules attached to any part of the FVII polypeptide including any amino acid residue or carbohydrate moiety of the Factor VII polypeptide. Chemical and/or enzymatic methods can be employed for conjugating PEG or other half-life extending moieties to a glycan on the Factor VII polypeptide. An example of an enzymatic conjugation process is described e.g. in WO03031464. The glycan may be naturally occurring or it may be engineered as described above for HEP conjugates. "Cysteine-PEGylated Factor VII polypeptide variants" according to the present invention have one or more PEG molecules conjugated to a sulfhydryl group of a cysteine residue present or introduced in the FVII polypeptide.

Fusion Proteins

Fusion proteins are proteins created through the in-frame joining of two or more DNA sequences which originally encode separate proteins or peptides or fragments thereof. Translation of the fusion protein DNA sequence will result in a single protein sequence which may have functional properties derived from each of the original proteins or peptides. DNA sequences encoding fusion proteins may be created artificially by standard molecular biology methods such as overlapping PCR or DNA ligation and the assembly is performed excluding the stop codon in the first 5'-end DNA sequence while retaining the stop codon in the 3'-end DNA sequence. The resulting fusion protein DNA sequence may be inserted into an appropriate expression vector that supports the heterologous fusion protein expression in standard host organisms such as bacteria, yeast, fungi, insect cells or mammalian cells.

Fusion proteins may contain a linker or spacer peptide sequence that separates the protein or peptide parts which define the fusion protein.

In one interesting embodiment of the invention, the Factor VII polypeptide is a fusion protein comprising a Factor VII polypeptide and a fusion partner protein/peptide, for example an Fc domain or an albumin.

Fc Fusion Protein

The term "Fc fusion protein" is herein meant to encompass Factor VII polypeptides of this invention fused to an Fc domain that can be derived from any antibody isotype. An IgG Fc domain will often be preferred due to the relatively long circulatory half-life of IgG antibodies. The Fc domain may furthermore be modified in order to modulate certain effector functions such as e.g. complement binding and/or binding to certain Fc receptors. Fusion of FVII polypeptides with an Fc domain, which has the capacity to bind to FcRn receptors, will generally result in a prolonged circulatory half-life of the fusion protein compared to the half-life of the wt FVII polypeptides. Mutations in positions 234, 235 and 237 in an IgG Fc domain will generally result in reduced binding to the FcγRI receptor and possibly also the FcγRIIa and the FcγRIII receptors. These mutations do not alter binding to the FcRn receptor, which promotes a long circulatory half-life by an endocytic recycling pathway. Preferably, a modified IgG Fc domain of a fusion protein according to the invention comprises one or more of the following mutations that will result in decreased affinity to certain Fc receptors (L234A, L235E, and G237A) and in reduced C1q-mediated complement fixation (A330S and P331S), respectively. Alternatively, the Fc domain may be an IgG4 Fc domain, preferably comprising the S241P/S228P mutation.

Production of Factor VII Polypeptides

Factor VII polypeptides, of the current invention, may be recombinantly produced using well known methods of production and purification; some examples of these methods are described below; yet further examples of methods of production and purification are, inter alia, described in WO2007/031559.

In one aspect, the invention relates to a method for producing Factor VII polypeptides. The Factor VII polypeptides described herein may be produced by means of recombinant nucleic acid techniques. In general, a cloned human wild-type Factor VII nucleic acid sequence is modified to encode the desired protein. This modified sequence is then inserted into an expression vector, which is in turn transformed or transfected into host cells. Higher eukaryotic cells, in particular cultured mammalian cells, are preferred as host cells.

In a further aspect, the invention relates to a transgenic animal containing and expressing the polynucleotide construct.

The complete nucleotide and amino acid sequences for human wild-type Factor VII are known (see U.S. Pat. No. 4,784,950, where the cloning and expression of recombinant human Factor VII is described).

The amino acid sequence alterations may be accomplished by a variety of know techniques. Modification of the nucleic acid sequence may be by site-specific mutagenesis. Techniques for site-specific mutagenesis are well known in the art and are described in, for example, Zoller and Smith (DNA 3:479-488, 1984) or "Splicing by extension overlap", Horton et al., Gene 77, 1989, pp. 61-68. Thus, using the nucleotide and amino acid sequences of Factor VII, one may introduce the alteration(s) of choice. Likewise, procedures for preparing a DNA construct using polymerase chain reaction using specific primers are well known to persons skilled in the art (cf. PCR Protocols, 1990, Academic Press, San Diego, Calif., USA).

The nucleic acid construct encoding the Factor VII polypeptide of the invention may suitably be of genomic or cDNA origin, The nucleic acid construct encoding the Factor VII polypeptide may also be prepared synthetically by established standard methods, e.g. the phosphoramidite method described by Beaucage and Caruthers, Tetrahedron Letters 22 (1981), 1859-1869, The DNA sequences encoding the human Factor VII polypeptides may also be prepared by polymerase chain reaction using specific primers, for instance as described in U.S. Pat. No. 4,683,202, Saiki et al., Science 239 (1988), 487-491, or Sambrook et al., supra.

Furthermore, the nucleic acid construct may be of mixed synthetic and genomic, mixed synthetic and cDNA or mixed genomic and cDNA origin prepared by ligating fragments of synthetic, genomic or cDNA origin (as appropriate), the fragments corresponding to various parts of the entire nucleic acid construct, in accordance with standard techniques.

The nucleic acid construct is preferably a DNA construct. DNA sequences for use in producing Factor VII polypeptides according to the present invention will typically encode a pre-pro polypeptide at the amino-terminus of Factor VII to obtain proper posttranslational processing (e.g. gamma-carboxylation of glutamic acid residues) and secretion from the host cell. The pre-pro polypeptide may be that of Factor VII or another vitamin K-dependent plasma protein, such as Factor IX, Factor X, prothrombin, protein C or protein S. As will be appreciated by those skilled in the art, additional modifications can be made in the amino acid sequence of the Factor VII polypeptides where those modifications do not significantly impair the ability of the protein to act as a coagulant.

The DNA sequences encoding the human Factor VII polypeptides are usually inserted into a recombinant vector which may be any vector, which may conveniently be subjected to recombinant DNA procedures, and the choice of vector will often depend on the host cell into which it is to be introduced. Thus, the vector may be an autonomously replicating vector, i.e. a vector, which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector is preferably an expression vector in which the DNA sequence encoding the human Factor VII polypeptides is operably linked to additional segments required for transcription of the DNA. In general, the expression vector is derived from plasmid or viral DNA, or may contain elements of both. The term, "operably linked" indicates that the segments are arranged so that they function in concert for their intended purposes, e.g. transcription initiates in a promoter and proceeds through the DNA sequence coding for the polypeptide.

Expression vectors for use in expressing Factor VIIa polypeptide variants will comprise a promoter capable of directing the transcription of a cloned gene or cDNA. The promoter may be any DNA sequence, which shows transcriptional activity in the host cell of choice and may be derived from genes encoding proteins either homologous or heterologous to the host cell.

Examples of suitable promoters for directing the transcription of the DNA encoding the human Factor VII polypeptide in mammalian cells are the SV40 promoter (Subramani et al., Mol. Cell Biol. 1 (1981), 854-864), the MT-1 (metallothionein gene) promoter (Palmiter et al., Science 222 (1983), 809-814), the CMV promoter (Boshart et al., Cell 41:521-530, 1985) or the adenovirus 2 major late promoter (Kaufman and Sharp, Mol. Cell. Biol, 2:1304-1319, 1982).

The DNA sequences encoding the Factor VII polypeptides may also, if necessary, be operably connected to a suitable terminator, such as the human growth hormone terminator (Palmiter et al., Science 222, 1983, pp. 809-814) or the TPI1 (Alber and Kawasaki, J. Mol. Appl. Gen. 1, 1982, pp. 419-434) or ADH3 (McKnight et al., The EMBO J. 4, 1985, pp. 2093-2099) terminators. Expression vectors may also contain a set of RNA splice sites located downstream from the promoter and upstream from the insertion site for the Factor VII sequence itself. Preferred RNA splice sites may be obtained from adenovirus and/or immunoglobulin genes. Also contained in the expression vectors is a polyadenylation signal located downstream of the insertion site. Particularly preferred polyadenylation signals include the early or late polyadenylation signal from SV40 (Kaufman and Sharp, ibid.), the polyadenylation signal from the adenovirus 5 Elb region, the human growth hormone gene terminator (DeNoto et al. Nucl. Acids Res. 9:3719-3730, 1981) or the polyadenylation signal from the human Factor VII gene or the bovine Factor VII gene. The expression vectors may also include a noncoding viral leader sequence, such as the adenovirus 2 tripartite leader, located between the promoter and the RNA splice sites; and enhancer sequences, such as the SV40 enhancer.

To direct the Factor VII polypeptides of the present invention into the secretory pathway of the host cells, a secretory signal sequence (also known as a leader sequence, prepro sequence or pre sequence) may be provided in the recombinant vector. The secretory signal sequence is joined to the DNA sequences encoding the human Factor VII polypeptides in the correct reading frame. Secretory signal sequences are commonly positioned 5' to the DNA sequence encoding the peptide. The secretory signal sequence may be that, normally associated with the protein or may be from a gene encoding another secreted protein.

The procedures used to ligate the DNA sequences coding for the Factor VII polypeptides, the promoter and optionally the terminator and/or secretory signal sequence, respectively, and to insert them into suitable vectors containing the information necessary for replication, are well known to persons skilled in the art (cf., for instance, Sambrook et al., Molecular Cloning: A Laboratory Manual, Cold Spring Harbor, N. Y., 1989).

Methods of transfecting mammalian cells and expressing DNA sequences introduced in the cells are described in e.g. Kaufman and Sharp, J. Mol. Biol. 159 (1982), 601-621; Southern and Berg, J. Mol. Appl. Genet. 1 (1982), 327-341; Loyter et al., Proc. Natl. Acad. Sci. USA 79 (1982), 422-426; Wigler et al., Cell 14 (1978), 725; Corsaro and Pearson, Somatic Cell Genetics 7 (1981), 603, Graham and van der Eb, Virology 52 (1973), 456; and Neumann et al., EMBO J. 1 (1982), 841-845.

Cloned DNA sequences are introduced into cultured mammalian cells by, for example, calcium phosphate-mediated transfection (Wigler et al., Cell 14:725-732, 1978; Corsaro and Pearson, Somatic Cell Genetics 7:603-616, 1981; Graham and Van der Eb, Virology 52d:456-467, 1973) or electroporation (Neumann et al., EMBO J. 1:841-845, 1982). To identify and select cells that express the exogenous DNA, a gene that confers a selectable phenotype (a selectable marker) is generally introduced into cells along with the gene or cDNA of interest. Preferred selectable markers include genes that confer resistance to drugs such as neomycin, hygromycin, and methotrexate. The selectable marker may be an amplifiable selectable marker. A preferred amplifiable selectable marker is a dihydrofolate reductase (DHFR) sequence. Selectable markers may be introduced into the cell on a separate plasmid at the same time as the gene of interest, or they may be introduced on the same plasmid. If, on the same plasmid, the selectable marker and the gene of interest may be under the control of different promoters or the same promoter, the latter arrangement producing a dicistronic message. Constructs of this type are known in the art (for example, Levinson and Simonsen, U.S. Pat. No. 4,713,339). It may also be advantageous to add additional DNA, known as "carrier DNA," to the mixture that is introduced into the cells.

After the cells have taken up the DNA, they are grown in an appropriate growth medium, typically 1-2 days, to begin expressing the gene of interest. As used herein the term "appropriate growth medium" means a medium containing nutrients and other components required for the growth of cells and the expression of the Factor VII polypeptides of interest. Media generally include a carbon source, a nitrogen source, essential amino acids, essential sugars, vitamins, salts, phospholipids, protein and growth factors. For production of gamma-carboxylated proteins, the medium will contain vitamin K, preferably at a concentration of about 0.1 μg/ml to about 5 μg/ml. Drug selection is then applied to select for the growth of cells that are expressing the selectable marker in a stable fashion. For cells that have been transfected with an amplifiable selectable marker the drug concentration may be increased to select for an increased copy number of the cloned sequences, thereby increasing expression levels.

Clones of stably transfected cells are then screened for expression of the human Factor VII polypeptide of interest.

The host cell into which the DNA sequences encoding the Factor VII polypeptides is introduced may be any cell, which is capable of producing the posttranslational modified human Factor VII polypeptides and includes yeast, fungi and higher eucaryotic cells.

Examples of mammalian cell lines for use in the present invention are the Chinese Hamster Ovary (CHO) cells (e.g. ATCC CCL 61), CHO DUKX cells (Urlaub and Chasin, Proc. Natl. Acad. Sci. USA 77:4216-4220, 1980), baby hamster kidney (BHK) and 293 (ATCC CRL 1573; Graham et al., J. Gen. Virol. 36:59-72, 1977) cell lines.

The transformed or transfected host cell described above is then cultured in a suitable nutrient medium under conditions permitting expression of the Factor VII polypeptide after which all or part of the resulting peptide may be recovered from the culture. The medium used to culture the cells may be any conventional medium suitable for growing the host cells, such as minimal or complex media containing appropriate supplements. Suitable media are available from commercial suppliers or may be prepared according to published recipes (e.g. in catalogues of the American Type Culture Collection). The Factor VII polypeptide produced by the cells may then be recovered from the culture medium by conventional procedures including separating the host cells from the medium by centrifugation or filtration, precipitating the proteinaqueous components of the supernatant or filtrate by means of a salt, e.g. ammonium sulphate, purification by a variety of chromatographic procedures, e.g. ion exchange chromatography, gelfiltration chromatography, affinity chromatography, or the like, dependent on the type of polypeptide in question.

Transgenic animal technology may be employed to produce the Factor VII polypeptides of the invention. It is preferred to produce the proteins within the mammary glands of a host female mammal. Expression in the mammary gland and subsequent secretion of the protein of interest into the milk overcomes many difficulties encountered in isolating proteins from other sources. Milk is readily collected, available in large quantities, and biochemically well characterized. Furthermore, the major milk proteins are present in milk at high concentrations (typically from about 1 to 15 g/l).

From a commercial point of view, it is clearly preferable to use as the host a species that has a large milk yield. While smaller animals such as mice and rats can be used (and are preferred at the proof of principle stage), it is preferred to use livestock mammals including, but not limited to, pigs, goats, sheep and cattle. Sheep are particularly preferred due to such factors as the previous history of transgenesis in this species, milk yield, cost and the ready availability of equipment for collecting sheep milk (see, for example, WO 88/00239 for a comparison of factors influencing the choice of host species). It is generally desirable to select a breed of host animal that has been bred for dairy use, such as East Friesland sheep, or to introduce dairy stock by breeding of the transgenic line at a later date. In any event, animals of known, good health status should be used.

To obtain expression in the mammary gland, a transcription promoter from a milk protein gene is used. Milk protein genes include those genes encoding caseins (see U.S. Pat. No. 5,304,489), beta-lactoglobulin, a-lactalbumin, and whey acidic protein. The beta-lactoglobulin (BLG) promoter is preferred. In the case of the ovine beta-lactoglobulin gene, a region of at least the proximal 406 bp of 5' flanking sequence of the gene will generally be used, although larger portions of the 5' flanking sequence, up to about 5 kbp, are preferred, such as a ~4.25 kbp DNA segment encompassing the 5' flanking promoter and non-coding portion of the beta-lactoglobulin gene (see Whitelaw et al., Biochem. J. 286: 31-39 (1992)). Similar fragments of promoter DNA from other species are also suitable.

Other regions of the beta-lactoglobulin gene may also be incorporated in constructs, as may genomic regions of the gene to be expressed. It is generally accepted in the art that constructs lacking introns, for example, express poorly in comparison with those that contain such DNA sequences (see Brinster et al., Proc. Natl. Acad. Sci. USA 85: 836-840 (1988); Palmiter et al., Proc. Natl. Acad. Sci. USA 88: 478-482 (1991); Whitelaw et al., Transgenic Res. 1: 3-13 (1991); WO 89/01343; and WO 91/02318, each of which is incorporated herein by reference). In this regard, it is generally preferred, where possible, to use genomic sequences containing all or some of the native introns of a gene encoding the protein or polypeptide of interest, thus the further inclusion of at least some introns from, e.g, the beta-lactoglobulin gene, is preferred. One such region is a DNA segment that provides for intron splicing and RNA polyadenylation from the 3' non-coding region of the ovine beta-lactoglobulin gene. When substituted for the natural 3' non-coding sequences of a gene, this ovine beta-lactoglobulin segment can both enhance and stabilize expression levels of the protein or polypeptide of interest. Within other embodiments, the region surrounding the initiation ATG of the variant Factor VII sequence is replaced with corresponding sequences from a milk specific protein gene. Such replacement provides a putative tissue-specific initiation environment to enhance expression. It is convenient to replace the entire variant Factor VII pre-pro and 5' non-coding sequences with those of, for example, the BLG gene, although smaller regions may be replaced.

For expression of Factor VII polypeptides in transgenic animals, a DNA segment encoding variant Factor VII is operably linked to additional DNA segments required for its expression to produce expression units. Such additional segments include the above-mentioned promoter, as well as sequences that provide for termination of transcription and polyadenylation of mRNA. The expression units will further include a DNA segment encoding a secretory signal sequence operably linked to the segment encoding modified Factor VII. The secretory signal sequence may be a native Factor VII secretory signal sequence or may be that of another protein, such as a milk protein (see, for example, von Heijne, Nucl. Acids Res. 14: 4683-4690 (1986); and Meade et al., U.S. Pat. No. 4,873,316, which are incorporated herein by reference).

Construction of expression units for use in transgenic animals is conveniently carried out by inserting a variant Factor VII sequence into a plasmid or phage vector containing the additional DNA segments, although the expression unit may be constructed by essentially any sequence of ligations. It is particularly convenient to provide a vector containing a DNA segment encoding a milk protein and to replace the coding sequence for the milk protein with that of a Factor VII variant; thereby creating a gene fusion that includes the expression control sequences of the milk protein gene. In any event, cloning of the expression units in plasmids or other vectors facilitates the amplification of the variant Factor VII sequence. Amplification is conveniently carried out in bacterial (e.g. E. coli) host cells, thus the vectors will typically include an origin of replication and a selectable marker functional in bacterial host cells. The expression unit is then introduced into fertilized eggs (including early-stage embryos) of the chosen host species. Introduction of heterologous DNA can be accomplished by one of several routes, including microinjection (e.g. U.S. Pat. No. 4,873,191), retroviral infection (Jaenisch, Science 240: 1468-1474 (1988))

or site-directed integration using embryonic stem (ES) cells (reviewed by Bradley et al., Bio/Technology 10: 534-539 (1992)). The eggs are then implanted into the oviducts or uteri of pseudopregnant females and allowed to develop to term. Offspring carrying the introduced DNA in their germ line can pass the DNA on to their progeny in the normal, Mendelian fashion, allowing the development of transgenic herds. General procedures for producing transgenic animals are known in the art (see, for example, Hogan et al., Manipulating the Mouse Embryo: A Laboratory Manual, Cold Spring Harbor Laboratory, 1986; Simons et al., Bio/Technology 6: 179-183 (1988); Wall et al., Biol. Reprod. 32: 645-651 (1985); Buhler et al., Bio/Technology 8: 140-143 (1990); Ebert et al., Bio/Technology 9: 835-838 (1991); Krimpenfort et al., Bio/Technology 9: 844-847 (1991); Wall et al., J. Cell. Biochem. 49: 113-120 (1992); U.S. Pat. No. 4,873,191; U.S. Pat. No. 4,873,316; WO 88/00239, WO 90/05188, WO 92/11757; and GB 87/00458). Techniques for introducing foreign DNA sequences into mammals and their germ cells were originally developed in the mouse (see, e.g., Gordon et al., Proc. Natl. Acad. Sci. USA 77: 7380-7384 (1980); Gordon and Ruddle, Science 214: 1244-1246 (1981); Palmiter and Brinster, Cell 41: 343-345 (1985); Brinster et al., Proc. Natl. Acad. Sci. USA 82: 4438-4442 (1985); and Hogan et al. (ibid.)). These techniques were subsequently adapted for use with larger animals, including livestock species (see, e.g., WO 88/00239, WO 90/05188, and WO 92/11757; and Simons et al., Bio/Technology 6: 179-183 (1988)). To summarise, in the most efficient route used to date in the generation of transgenic mice or livestock, several hundred linear molecules of the DNA of interest are injected into one of the pro-nuclei of a fertilized egg according to established techniques. Injection of DNA into the cytoplasm of a zygote can also be employed.

Purification

The Factor VII polypeptides of the invention are recovered from cell culture medium. The Factor VII polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing (IEF), differential solubility (e.g., ammonium sulfate precipitation), or extraction (see, e.g., Protein Purification, J.-C. Janson and Lars Ryden, editors, VCH Publishers, New York, 1989). Preferably, Factor VII polypeptides may be purified by affinity chromatography on an anti-Factor VII antibody column. The use of calcium-dependent monoclonal antibodies, as described by Wakabayashi et al., J. Biol. Chem. 261:11097-11108, (1986) and Thim et al., Biochemistry 27: 7785-7793, (1988), is particularly preferred. Additional purification may be achieved by conventional chemical purification means, such as high performance liquid chromatography. Other methods of purification, including barium citrate precipitation, are known in the art, and may be applied to the purification of the novel Factor VII polypeptides described herein (see, for example, Scopes, R., Protein Purification, Springer-Verlag, N.Y., 1982).

For therapeutic purposes it is preferred that the Factor VII polypeptides of the invention are substantially pure. Thus, in a preferred embodiment of the invention the Factor VII polypeptides of the invention are purified to at least about 90 to 95% homogeneity, preferably to at least about 98% homogeneity. Purity may be assessed by several methods known in the art e.g. HPLC, gel electrophoresis and amino-terminal amino acid sequencing.

The Factor VII polypeptide is cleaved at its activation site in order to convert it to its two-chain form. Activation may be carried out according to procedures known in the art, such as those disclosed by Osterud, et al., Biochemistry 11:2853-2857 (1972); Thomas, U.S. Pat. No. 4,456,591; Hedner and Kisiel, J. Clin. Invest. 71:1836-1841 (1983); or Kisiel and Fujikawa, Behring Inst. Mitt. 73:29-42 (1983). Alternatively, as described by Bjoern et al. (Research Disclosure, 269 September 1986, pp. 564-565), Factor VII may be activated by passing it through an ion-exchange chromatography column, such as Mono Q® (Pharmacia fine Chemicals) or the like. The resulting activated Factor VII variant may then be formulated and administered as described below.

Assays

Provided herein are suitable in vitro proteolytic and anti-thrombin reactivity assays for selecting preferred Factor VII polypeptides according to the invention. Such assays are described in detail in Example 5. Briefly, the assays can be performed as simple preliminary in vitro tests, as follows:

The proteolytic activity of FVIIa polypeptides can be measured using the physiological substrate plasma-derived factor X (X) as substrate at physiological pH and in the presence of calcium and vesicles composed of phosphatidyl choline (PC) and phosphatidyl serine (PS) to support the reaction. The assay is performed by incubating FVIIa with FX at a substrate concentration below Km for the reaction and for a period sufficient long to allow for the generation of measurable amounts of FXa while keeping the conversion of FX below 20%. The generated FXa is quantified after the addition of a suitable chromogenic substrate such as S-2765 and reported relative to that of wild-type FVIIa following normalisation according to the concentration of the FVIIa variant tested.

The antithrombin reactivity of the FVIIa polypeptides can be measured at physiological pH under pseudo-first order conditions in the presence of excess plasma-derived antithrombin, low molecular weight (LMW) heparin and calcium. Residual FVIIa activity is measured discontinuously throughout the time course of the inhibition reaction using a chromogenic substrate such as S-2288. The rate of inhibition is obtained by non-linear least-squares fitting of data to a single exponential decay function and reported relative to that of wild-type FVIIa following normalisation of inhibition rates according to the antithrombin concentration used. The kinetic characterisation of heparin-catalyzed and uncatalyzed inhibition of blood coagulation proteinases by antithrombinis is described in Olson et al. (1993), *Methods Enzymol.* 222, 525-559.

Pharmaceutical Compositions

In one aspect, the present invention relates to compositions and formulations comprising a Factor VII polypeptide of the invention. For example, the invention provides a pharmaceutical composition that comprises a Factor VII polypeptide of the invention, formulated together with a pharmaceutically acceptable carrier.

Accordingly, one object of the invention is to provide a pharmaceutical formulation comprising a Factor VII polypeptide which is present in a concentration from 0.25 mg/ml to 100 mg/ml, and wherein said formulation has a pH from 2.0 to 10.0. The formulation may further comprise one or more of a buffer system, a preservative, a tonicity agent, a chelating agent, a stabilizer, an antioxidant or a surfactant, as well as various combinations thereof. The use of preservatives, isotonic agents, chelating agents, stabilizers, antioxidant and surfactants in pharmaceutical compositions is well-known to the skilled person. Reference may be made to Remington: The Science and Practice of Pharmacy, 19th edition, 1995.

In one embodiment, the pharmaceutical formulation is an aqueous formulation. Such a formulation is typically a solution or a suspension, but may also include colloids, dispersions, emulsions, and multi-phase materials. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment, the pharmaceutical formulation is a freeze-dried formulation, to which the physician or the patient adds solvents and/or diluents prior to use.

In a further aspect, the pharmaceutical formulation comprises an aqueous solution of a Factor VII polypeptide, and a buffer, wherein the polypeptide is present in a concentration from 1 mg/ml or above, and wherein said formulation has a pH from about 2.0 to about 10.0.

In a further aspect, the pharmaceutical formulation may be any one of those disclosed in WO2014/057069, which is herein incorporated by reference; or it may be the formulation described in Example 18.

A Factor VII polypeptide of the invention may be administered parenterally, such as intravenously, such as intramuscularly, such as subcutaneously. Alternatively, a FVII polypeptide of the invention may be administered via a non-parenteral route, such as perorally or topically. An polypeptide of the invention may be administered prophylactically. An polypeptide of the invention may be administered therapeutically (on demand).

Therapeutic Uses

In a broad aspect, a Factor VII polypeptide of the present invention or a pharmaceutical formulation comprising said polypeptide, may be used as a medicament.

In one aspect, a Factor VII polypeptide of the present invention or a pharmaceutical formulation comprising said polypeptide, may be used to treat a subject with a coagulopathy.

In another aspect, a Factor VII polypeptide of the present invention or a pharmaceutical formulation comprising said polypeptide may be used for the preparation of a medicament for the treatment of bleeding disorders or bleeding episodes or for the enhancement of the normal haemostatic system.

In a further aspect, a Factor VII polypeptide of the present invention or a pharmaceutical formulation comprising said polypeptide may be used for the treatment of haemophilia A, haemophilia B or haemophilia A or B with acquired inhibitors.

In another aspect, a Factor VII polypeptide of the present invention or a pharmaceutical formulation comprising said polypeptide may be used in a method for the treatment of bleeding disorders or bleeding episodes in a subject or for the enhancement of the normal haemostatic system, the method comprising administering a therapeutically or prophylactically effective amount of a Factor VII polypeptide of the present invention to a subject in need thereof.

The term "subject", as used herein, includes any human patient, or non-human vertebrates.

The term "treatment", as used herein, refers to the medical therapy of any human or other vertebrate subject in need thereof. Said subject is expected to have undergone physical examination by a medical practitioner, or a veterinary medical practitioner, who has given a tentative or definitive diagnosis which would indicate that the use of said specific treatment is beneficial to the health of said human or other vertebrate. The timing and purpose of said treatment may vary from one individual to another, according to the status quo of the subject's health. Thus, said treatment may be prophylactic, palliative, symptomatic and/or curative. In terms of the present invention, prophylactic, palliative, symptomatic and/or curative treatments may represent separate aspects of the invention.

The term "coagulopathy", as used herein, refers to an increased haemorrhagic tendency which may be caused by any qualitative or quantitative deficiency of any pro-coagulative component of the normal coagulation cascade, or any upregulation of fibrinolysis. Such coagulopathies may be congenital and/or acquired and/or iatrogenic and are identified by a person skilled in the art. Non-limiting examples of congenital hypocoagulopathies are haemophilia A, haemophilia B, Factor VII deficiency, Factor X deficiency, Factor XI deficiency, von Willebrand's disease and thrombocytopenias such as Glanzmann's thombasthenia and Bernard-Soulier syndrome. The clinical severity of haemophilia A or B is determined by the concentration of functional units of FIX/Factor VIII in the blood and is classified as mild, moderate, or severe. Severe haemophilia is defined by a clotting factor level of <0.01 U/ml corresponding to <1% of the normal level, while people with moderate and mild haemophilia have levels from 1-5% and >5%, respectively. Haemophilia A with "inhibitors" (that is, allo-antibodies against factor VIII) and haemophilia B with "inhibitors" (that is, allo-antibodies against factor IX) are non-limiting examples of coagulopathies that are partly congenital and partly acquired.

A non-limiting example of an acquired coagulopathy is serine protease deficiency caused by vitamin K deficiency; such vitamin K-deficiency may be caused by administration of a vitamin K antagonist, such as warfarin. Acquired coagulopathy may also occur following extensive trauma. In this case otherwise known as the "bloody vicious cycle", it is characterised by haemodilution (dilutional thrombocytopaenia and dilution of clotting factors), hypothermia, consumption of clotting factors and metabolic derangements (acidosis). Fluid therapy and increased fibrinolysis may exacerbate this situation. Said haemorrhage may be from any part of the body.

A non-limiting example of an iatrogenic coagulopathy is an overdosage of anticoagulant medication—such as heparin, aspirin, warfarin and other platelet aggregation inhibitors—that may be prescribed to treat thromboembolic disease. A second, non-limiting example of iatrogenic coagulopathy is that which is induced by excessive and/or inappropriate fluid therapy, such as that which may be induced by a blood transfusion.

In one embodiment of the current invention, haemorrhage is associated with haemophilia A or B. In another embodiment, haemorrhage is associated with haemophilia A or B with acquired inhibitors. In another embodiment, haemorrhage is associated with thrombocytopenia. In another embodiment, haemorrhage is associated with von Willebrand's disease. In another embodiment, haemorrhage is associated with severe tissue damage. In another embodiment, haemorrhage is associated with severe trauma. In another embodiment, haemorrhage is associated with surgery. In another embodiment, haemorrhage is associated with haemorrhagic gastritis and/or enteritis. In another embodiment, the haemorrhage is profuse uterine bleeding, such as in placental abruption. In another embodiment, haemorrhage occurs in organs with a limited possibility for mechanical haemostasis, such as intracranially, intraaurally or intraocularly. In another embodiment, haemorrhage is associated with anticoagulant therapy.

The invention is further described by the following non-limiting list of embodiments:

Embodiment 1

Factor VII polypeptide comprising two or more substitutions relative to the amino acid sequence of human Factor VII (SEQ ID NO: 1), wherein T293 is replaced by Lys (K), Arg (R), Tyr (Y) or Phe (F) and L288 is replaced by Phe (F), Tyr (Y), Asn (N), Ala (A) or Trp (W) and/or W201 is replaced by Arg (R), Met (M), or Lys (K) and/or K337 is replaced by Ala (A) or Gly (G); optionally, where Q176 is replaced by Lys (K), Arg (R) or Asn (N); or Q286 is replaced by Asn (N).

Embodiment 1(i)

Factor VII polypeptide according to embodiment 1, wherein T293 is replaced by Lys (K), Arg (R), Tyr (Y) or Phe (F); and L288 is replaced by Phe (F), Tyr (Y), Asn (N), Ala (A) or Trp (W) and/or W201 is replaced by Arg (R), Met (M) or Lys (K) and/or K337 is replaced by Ala (A) or Gly (G).

Embodiment 1(ii)

Factor VII polypeptide according to embodiment 1, wherein L288 is replaced by Phe (F), Tyr (Y), Asn (N) or Ala (A).

Embodiment 1(iii)

Factor VII polypeptide according to embodiment 1, wherein W201 is replaced by Arg (R), Met (M) or Lys (K).

Embodiment 1(iv)

Factor VII polypeptide according to embodiment 1, wherein K337 is replaced by Ala (A) or Gly (G).

Embodiment 2

Factor VII polypeptide according to embodiment 1, wherein T293 is replaced by Lys (K), Arg (R), Tyr (Y) or Phe (F).

Embodiment 2(i)

Factor VII polypeptide according to any one of embodiments 1-2, wherein T293 is replaced by Lys (K), Arg (R), Tyr (Y) or Phe (F) and L288 is replaced by Phe (F), Tyr (Y), Asn (N), Ala (A) or Trp (W).

Embodiment 2(ii)

Factor VII polypeptide according to any one of embodiments 1-2, wherein T293 is replaced by Lys (K) and L288 is replaced by Phe (F).

Embodiment 2(iii)

Factor VII polypeptide according to any one of embodiments 1-2, wherein T293 is replaced by Lys (K) and L288 is replaced by Tyr (Y).

Embodiment 2(iv)

Factor VII polypeptide according to any one of embodiments 1-2, wherein T293 is replaced by Lys (K) and L288 is replaced by Asn (N).

Embodiment 2(v)

Factor VII polypeptide according to any one of embodiments 1-2, wherein T293 is replaced by Lys (K) and L288 is replaced by Ala (A).

Embodiment 2(vi)

Factor VII polypeptide according to any one of embodiments 1-2, wherein T293 is replaced by Lys (K) and L288 is replaced by Trp (W).

Embodiment 2(vii)

Factor VII polypeptide according to any one of embodiments 1-2, wherein T293 is replaced by Arg (R) and L288 is replaced by Phe (F).

Embodiment 2(viii)

Factor VII polypeptide according to any one of embodiments 1-2, wherein T293 is replaced by Arg (R) and L288 is replaced by Tyr (Y).

Embodiment 2(ix)

Factor VII polypeptide according to any one of embodiments 1-2, wherein T293 is replaced by Arg (R) and L288 is replaced by Asn (N).

Embodiment 2(x)

Factor VII polypeptide according to any one of embodiments 1-2, wherein T293 is replaced by Arg (R) and L288 is replaced by Ala (A).

Embodiment 2(xi)

Factor VII polypeptide according to any one of embodiments 1-2, wherein T293 is replaced by Arg (R) and L288 is replaced by Trp (W).

Embodiment 2(xii)

Factor VII polypeptide according to any one of embodiments 1-2, wherein T293 is replaced by Tyr (Y); and L288 is replaced by Phe (F).

Embodiment 2(xiii)

Factor VII polypeptide according to any one of embodiments 1-2, wherein T293 is replaced by Tyr (Y); and L288 is replaced by Tyr (Y).

Embodiment 2(xiv)

Factor VII polypeptide according to any one of embodiments 1-2, wherein T293 is replaced by Tyr (Y) and L288 is replaced by Asn (N).

Embodiment 2(xv)

Factor VII polypeptide according to any one of embodiments 1-2, wherein T293 is replaced by Tyr (Y) and L288 is replaced by Ala (A).

Embodiment 2(xvi)

Factor VII polypeptide according to any one of embodiments 1-2, wherein T293 is replaced by Tyr (Y) and L288 is replaced by Trp (W).

Embodiment 2(xvii)

Factor VII polypeptide according to any one of embodiments 1-2, wherein T293 is replaced by Phe (F) and L288 is replaced by Phe (F).

Embodiment 2(xviii)

Factor VII polypeptide according to any one of embodiments 1-2, wherein T293 is replaced by Phe (F) and L288 is replaced by Tyr (Y).

Embodiment 2(xix)

Factor VII polypeptide according to any one of embodiments 1-2, wherein T293 is replaced by Phe (F) and L288 is replaced by Asn (N).

Embodiment 2(xx)

Factor VII polypeptide according to any one of embodiments 1-2, wherein T293 is replaced by Phe (F) and L288 is replaced by Ala (A).

Embodiment 2(xxi)

Factor VII polypeptide according to any one of embodiments 1-2, wherein T293 is replaced by Phe (F) and L288 is replaced by Trp (W).

Embodiment 2(xxii)

Factor VII polypeptide according to any one of embodiments 1-2, wherein T293 is replaced by Lys (K) and K337 is replaced by Ala (A).

Embodiment 2(xxiii)

Factor VII polypeptide according to any one of embodiments 1-2, wherein T293 is replaced by Arg (R) and K337 is replaced by Ala (A).

Embodiment 2(xxiv)

Factor VII polypeptide according to any one of embodiments 1-2, wherein T293 is replaced by Tyr (Y) and K337 is replaced by Ala (A).

Embodiment 2(xxv)

Factor VII polypeptide according to any one of embodiments 1-2, wherein T293 is replaced by Phe (F) and K337 is replaced by Ala (A).

Embodiment 2(xxvi)

Factor VII polypeptide according to any one of embodiments 1-2, wherein T293 is replaced by Lys (K) and K337 is replaced by Gly (G).

Embodiment 2(xxvii)

Factor VII polypeptide according to any one of embodiments 1-2, wherein T293 is replaced by Arg (R) and K337 is replaced by Gly (G).

Embodiment 2(xxviii)

Factor VII polypeptide according to any one of embodiments 1-2, wherein T293 is replaced by Tyr (Y) and K337 is replaced by Gly (G).

Embodiment 2(xxix)

Factor VII polypeptide according to any one of embodiments 1-2, wherein T293 is replaced by Phe (F) and K337 is replaced by Gly (G).

Embodiment 2(xxx)

Factor VII polypeptide according to any one of embodiments 2(ii)-2(xxii) wherein K337 is replaced by Ala (A).

Embodiment 3

Factor VII polypeptide according to embodiment 2, wherein the polypeptide comprises one of the following groups of substitutions: L288F/T293K, L288F/T293K/K337A, L288F/T293K/L305V, L288F/T293K/L305I, L288F/T293R, L288F/T293R/K337A, L288F/T293R/L305V, L288F/T293R/L305I, L288F/T293Y, L288F/T293Y/K337A, L288F/T293Y/L305V, L288F/T293Y/L305I, L288F/T293F, L288F/T293F/K337A, L288F/T293F/L305V, L288F/T293F/L305I, L288Y/T293K, L288Y/T293K/K337A, L288Y/T293K/L305V, L288Y/T293K/L305I, L288Y/T293R, L288Y/T293R/K337A, L288Y/T293R/L305V, L288Y/T293R/L305I, L288Y/T293Y, L288Y/T293Y/K337A, L288Y/T293Y/L305V, L288Y/T293Y/L305I, L288Y/T293F, L288Y/T293F/K337A, L288Y/T293F/L305V, L288Y/T293F/L305I, L288N/T293K, L288N/T293K/K337A, L288N/T293K/L305V, L288N/T293K/L305I, L288N/T293R, L288N/T293R/K337A, L288N/T293R/L305V, L288N/T293R/L305I, L288N/T293Y, L288N/T293Y/K337A, L288N/T293Y/L305V, L288N/T293Y/L305I, L288N/T293F, L288N/T293F/K337A, L288N/T293F/L305V, L288N/T293F/L305I, L288A/T293K, L288A/T293K/K337A, L288A/T293K/L305V, L288A/T293K/L305I, L288A/T293R, L288A/T293R/K337A, L288A/T293R/L305V, L288A/T293R/L305I, L288A/T293Y, L288A/T293Y/K337A, L288A/T293Y/L305V, L288A/T293Y/L305I, L288A/T293F, L288A/T293F/K337A, L288A/T293F/L305V or L288A/T293F/L305I.

Embodiment 4

Factor VII polypeptide according to embodiment 2, wherein the polypeptide has the following substitutions: L288F/T293K, L288F/T293K/K337A, L288F/T293R, L288F/T293R/K337A, L288Y/T293K, L288Y/T293K/K337A, L288Y/T293R, L288Y/T293R/K337A, L288N/T293K, L288N/T293K/K337A, L288N/T293R or L288N/T293R/K337A.

Embodiment 5

Factor VII polypeptide according to embodiment 1, wherein Q176 is replaced by Lys (K), Arg (R), or Asn (N).

Embodiment 6

Factor VII polypeptide according to embodiment 5, wherein the polypeptide comprises one of the following groups of substitutions: L288F/Q176K/K337A, L288Y/Q176K/K337A, L288N/Q176K/K337A or L288A/Q176K/K337A.

Embodiment 7

Factor VII polypeptide according to embodiment 1, wherein Q286 is replaced by Asn (N).

Embodiment 8

Factor VII polypeptide comprising one or more substitutions relative to the amino acid sequence of human Factor VII (SEQ ID NO:1), characterized in that one substitution is where L288 is replaced by Phe (F), Tyr (Y), Asn (N) or Ala (A), with the proviso that the polypeptide does not have the following pair of substitutions L288N/R290S or L288N/R290T.

Embodiment 9

Factor VII polypeptide according to any one of embodiments 1-2(xxx), 5 and 7-8, wherein the Factor VII polypeptide further comprises one or more of the following substitutions L305I, L305V or K337A.

Embodiment 10

Factor VII polypeptide comprising two or more substitutions relative to the amino acid sequence of human Factor VII (SEQ ID NO:1), wherein W201 is replaced by Arg (R), Met (M), or Lys (K) and wherein T293 is replaced by Lys (K), Arg (R), Tyr (Y) or Phe (F); wherein Q176 is replaced by Lys (K), Arg (R) or Asn (N); or Q286 is replaced by Asn (N).

Embodiment 10(i)

Factor VII polypeptide according to any one of embodiments 1-1(ii) or 10, wherein T293 is replaced by Lys (K), Arg (R), Tyr (Y) or Phe (F) and wherein W201 is replaced by Arg (R), Met (M) or Lys (K).

Embodiment 11

Factor VII polypeptide according to embodiment 10, wherein T293 is replaced by Lys (K), Arg (R), Tyr (Y) or Phe (F).

Embodiment 11(i)

Factor VII polypeptide according to any one of embodiments 1-2, 10 or 11, wherein T293 is replaced by Lys (K), Arg (R), Tyr (Y) or Phe (F) and W201 is replaced by Arg (R), Met (M) or Lys (K).

Embodiment 11(ii)

Factor VII polypeptide according to any one of embodiments 1-2, 10 or 11, wherein T293 is replaced by Lys (K) and W201 is replaced by Arg (R).

Embodiment 11(iii)

Factor VII polypeptide according to any one of embodiments 1-2, 10 or 11, wherein T293 is replaced by Lys (K) and W201 is replaced by Met (M).

Embodiment 11(iv)

Factor VII polypeptide according to any one of embodiments 1-2, 10 or 11, wherein T293 is replaced by Lys (K) and W201 is replaced by Lys (K).

Embodiment 11(v)

Factor VII polypeptide according to any one of embodiments 1-2, 10 or 11, wherein T293 is replaced by Arg (R) and W201 is replaced by Arg (R).

Embodiment 11(vi)

Factor VII polypeptide according to any one of embodiments 1-2, 10 or 11, wherein T293 is replaced by Arg (R) and W201 is replaced by Met (M).

Embodiment 11(vii)

Factor VII polypeptide according to any one of embodiments 1-2, 10 or 11, wherein T293 is replaced by Arg (R) and W201 is replaced by Lys (K).

Embodiment 11(viii)

Factor VII polypeptide according to any one of embodiments 1-2, 10 or 11, wherein T293 is replaced by Tyr (Y) and W201 is replaced by Arg (R).

Embodiment 11(ix)

Factor VII polypeptide according to any one of embodiments 1-2, 10 or 11, wherein T293 is replaced by Tyr (Y) and W201 is replaced by Met (M).

Embodiment 11(x)

Factor VII polypeptide according to any one of embodiments 1-2, 10 or 11, wherein T293 is replaced by Tyr (Y) and W201 is replaced by Lys (K).

Embodiment 11(xi)

Factor VII polypeptide according to any one of embodiments 1-2, 10 or 11, wherein T293 is replaced by Phe (F) and W201 is replaced by Arg (R).

Embodiment 11(xii)

Factor VII polypeptide according to any one of embodiments 1-2, 10 or 11, wherein T293 is replaced by Phe (F) and W201 is replaced by Met (M).

Embodiment 11(xiii)

Factor VII polypeptide according to any one of embodiments 1-2, 10 or 11, wherein T293 is replaced by Phe (F) and W201 is replaced by Lys (K).

Embodiment 12

Factor VII polypeptide according to embodiment 11, wherein the polypeptide comprises one of the following groups of substitutions: W201R/T293K, W201R/T293K/K337A, W201R/T293K/L305V, W201R/T293K/L305I, W201R/T293R, W201R/T293R/K337A, W201R/T293R/L305V, W201R/T293R/L305I, W201R/T293Y, W201R/

T293Y/K337A, W201R/T293Y/L305V, W201R/T293Y/L305I, W201R/T293F, W201R/T293F/K337A, W201R/T293F/L305V, W201R/T293F/L305I, W201K/T293K, W201K/T293K/K337A, W201K/T293K/L305V, W201K/T293K/L305I, W201K/T293R, W201K/T293R/K337A, W201K/T293R/L305V, W201K/T293R/L305I, W201K/T293Y, W201K/T293Y/K337A, W201K/T293Y/L305V, W201K/T293Y/L305I, W201K/T293F, W201K/T293F/K337A, W201K/T293F/L305V, W201K/T293F/L305I, W201M/T293K, W201M/T293K/K337A, W201M/T293K/L305V, W201M/T293K/L305I, W201M/T293R, W201M/T293R/K337A, W201M/T293R/L305V, W201M/T293R/L305I, W201M/T293Y, W201M/T293Y/K337A, W201M/T293Y/L305V, W201M/T293Y/L305I, W201M/T293F, W201M/T293F/K337A, W201M/T293F/L305V or W201M/T293F/L305I.

Embodiment 13

Factor VII polypeptide according to embodiment 11, wherein the polypeptide has the following substitutions: W201R/T293K, W201R/T293K/K337A, W201R/T293R, W201R/T293R/K337A, W201R/T293Y, W201R/T293F, W201K/T293K or W201M/T293K.

Embodiment 14

Factor VII polypeptide according to embodiment 10, wherein Q176 is replaced by Lys (K), Arg (R), or Asn (N).

Embodiment 15

Factor VII polypeptide according to embodiment 14, wherein the polypeptide comprises one of the following groups of substitutions W201R/Q176K, W201R/Q176R, W201K/Q176K, W201K/Q176R, W201M/Q176K, or W201M/Q176R.

Embodiment 16

Factor VII polypeptide according to embodiment 10, wherein Q286 is replaced by Asn (N).

Embodiment 17

Factor VII polypeptide according to any one of embodiments 10-11, 14, and 16, wherein the Factor VII polypeptide further comprises one or more of the following substitutions L305I, L305V or K337A.

Embodiment 18

Factor VII polypeptide comprising one or more substitutions relative to the amino acid sequence of human Factor VII (SEQ ID NO:1), characterized in that one substitution is where W201 is replaced by Arg (R), Met (M), or Lys (K).

Embodiment 19

Factor VII polypeptide comprising two or more substitutions relative to the amino acid sequence of human Factor VII (SEQ ID NO:1), wherein L288 is replaced by Phe (F), Tyr (Y), Asn (N), or Ala (A); wherein W201 is replaced by Arg (R), Met (M), or Lys (K) and, optionally, wherein T293 is replaced by Lys (K), Arg (R), Tyr (Y) or Phe (F); Q176 is replaced by Lys (K), Arg (R) or Asn (N); or Q286 is replaced by Asn (N).

Embodiment 20

Factor VII polypeptide according to embodiment 19, wherein the polypeptide comprises one of the following groups of substitutions L288F/W201K, L288F/W201R, L288F/W201M, L288N/W201K, L288N/W201R, L288N/W201M, L288Y/W201K, L288Y/W201R, L288Y/W201M, L288A/W201K, L288A/W201R, L288A/W201M, L288F/W201K/T293K, L288F/W201K/T293Y, L288F/W201R/T293K, L288F/W201R/T293Y, L288F/W201M/T293K, L288F/W201M/T293Y, L288N/W201K/T293K, L288N/W201K/T293Y, L288N/W201R/T293K, L288N/W201R/T293Y, L288N/W201M/T293K, L288N/W201M/T293Y, L288A/W201K/T293K, L288A/W201K/T293Y, L288A/W201R/T293K, L288A/W201R/T293Y, L288A/W201M/T293K, L288A/W201M/T293Y, L288Y/W201K/T293K, L288Y/W201K/T293Y, L288Y/W201R/T293K, L288Y/W201R/T293Y, L288Y/W201M/T293K or L288Y/W201M/T293Y.

Embodiment 21

Factor VII polypeptide according to any one of the preceding embodiments, wherein the Factor VII polypeptide further comprises one or more of the following substitutions R396C, Q250C, or 407C.

Embodiment 22

Factor VII polypeptide according to any one of the previous embodiments, wherein said Factor VII polypeptide is a cleaved, two-chain Factor VIIa polypeptide.

Embodiment 22(i)

Factor VII polypeptide according to any one of the preceding embodiments comprising two amino acid substitutions relative to the amino acid sequence of human Factor VII (SEQ ID NO:1).

Embodiment 22(ii)

Factor VII polypeptide according to any one of the preceding embodiments comprising three amino acid substitutions relative to the amino acid sequence of human Factor VII (SEQ ID NO:1).

Embodiment 22(iii)

Factor VII polypeptide according to any one of the preceding embodiments comprising four amino acid substitutions relative to the amino acid sequence of human Factor VII (SEQ ID NO:1).

Embodiment 22(iv)

Factor VII polypeptide according to any one of the preceding embodiments comprising five amino acid substitutions relative to the amino acid sequence of human Factor VII (SEQ ID NO:1).

Embodiment 22(v)

Factor VII polypeptide according to any one embodiments 22(i)-(iv) comprising at the most ten amino acid substitutions relative to the amino acid sequence of human Factor VII (SEQ ID NO:1).

Embodiment 22(vi)

Factor VII polypeptide according to any one of the preceding embodiments, which has a proteolytic activity that is at least 110%, such as at least 120%, such as at least 130%, such as at least 140%, such as at least 150%, such as at least 160%, such as at least 170%, such as at least 180%, such as at least 190%, such as at least 200%, such as at least 300%, such as at least 400%, such as at least 500%, such as at least 1000%, such as at least 3000%, such as at least 5000%, such as at least 10 000%, such as at least 30 000% that of wild type human Factor VIIa, as measured in an in vitro proteolytic assay, in the absence of soluble tissue factor.

Embodiment 22(vii)

Factor VII polypeptide according to any one of the preceding embodiments, which has less than 20%, such as less than 19%, such as less than 18%, such as less than 17%, such as less than 16%, such as less than 15%, such as less than 14%, such as less than 13%, such as less than 12%, such as less than 11%, such as less than 10%, such as less than 9%, such as less than 8%, such as less than 7%, such as less than 6%, such as less than 5% antithrombin reactivity compared to that of wild type human Factor VIIa (SEQ ID NO: 1), as measured in an antithrombin inhibition assay, in the presence of low molecular weight heparin and the absence of soluble tissue factor.

Embodiment 23

Factor VII polypeptide according to any of the preceding embodiments, wherein the Factor VII polypeptide is coupled with at least one half-life extending moiety.

Embodiment 24

Factor VII polypeptide according to embodiment 23, wherein the half-life extending moiety is selected from biocompatible fatty acids and derivatives thereof, Hydroxy Alkyl Starch (HAS) e.g. Hydroxy Ethyl Starch (HES), Poly Ethylen Glycol (PEG), Poly (Glyx-Sery)n (HAP), Hyaluronic acid (HA), Heparosan polymers (HEP), Phosphorylcholine-based polymers (PC polymer), Fleximers, Dextran, Poly-sialic acids (PSA), Fc domains, Transferrin, Albumin, Elastin like (ELP) peptides, XTEN polymers, PAS polymers, PA polymers, Albumin binding peptides, CTP peptides, FcRn binding peptides and any combination thereof.

Embodiment 25

Factor VII polypeptide according to embodiment 24, wherein the half-life extending moiety is a heparosan polymer.

Embodiment 26

Factor VII polypeptide according to embodiment 25, wherein the heparosan polymer has a molecular weight in a range selected from 13-65 kDa, 13-55 kDa, 25-55 kDa, 25-50 kDa, 25-45 kDa, 30-45 kDa and 38-42 kDa, or a molecular weight of 40 kDa.

Embodiment 26(i)

FVII polypeptide according to any one of embodiments 25-26, comprising the structural fragment shown in Formula I,

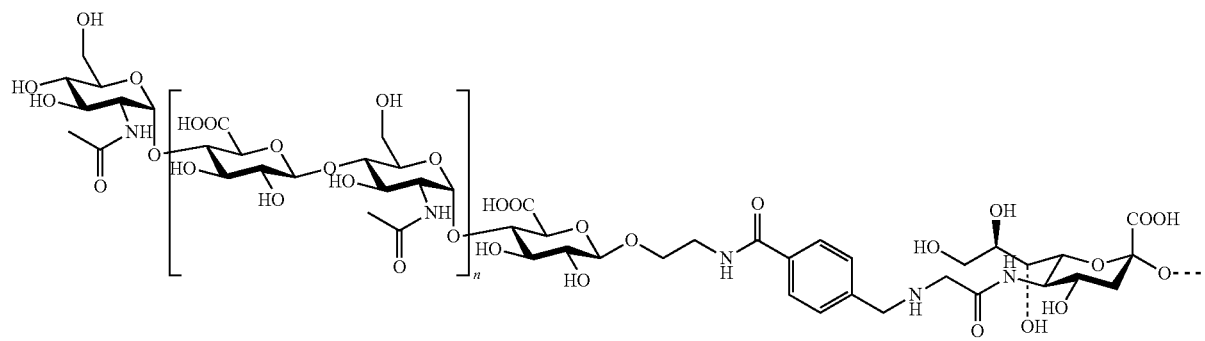

Formula I wherein n is an integer from 95-115.

Embodiment 26(ii)

Factor VII polypeptide according to any one of the preceding embodiments, which has a half-life that is increased by at least 100% compared to wild type human Factor VIIa (SEQ ID NO: 1).

Embodiment 27

Factor VII polypeptide according to any of the preceding embodiments, wherein said Factor VII polypeptide is disulfide linked to tissue factor.

Embodiment 28

Factor VII polypeptide according to any of the preceding embodiments, wherein said polypeptide has additional amino acid modifications that increase platelet affinity of the polypeptide.

Embodiment 29

Factor VII polypeptide according to any one of embodiments 1-22, wherein said polypeptide is a fusion protein comprising a Factor VII polypeptide according to any one of embodiments 1-22 and a fusion partner protein/peptide, for example an Fc domain or an albumin.

Embodiment 30

Polynucleotide that encodes a Factor VII polypeptide defined in any one of embodiments 1-22 and 28-29.

Embodiment 31

Recombinant host cell comprising the polynucleotide according to embodiment 30.

Embodiment 32

Method for producing the Factor VII polypeptide defined in any of embodiments 1-22 and 28-29, the method comprising cultivating a cell in an appropriate medium under conditions allowing expression of the polynucleotide construct and recovering the resulting polypeptide from the medium.

Embodiment 33

Pharmaceutical composition comprising a Factor VII polypeptide as defined in any of embodiments 1-29 and a pharmaceutically acceptable carrier.

Embodiment 34

Method for the treatment of bleeding disorders or bleeding episodes in a subject or for the enhancement of the normal haemostatic system, the method comprising administering a therapeutically or prophylactically effective amount of a Factor VII polypeptide as defined in any of embodiments 1-29 to a subject in need thereof.

Embodiment 35

Factor VII polypeptide as defined in any of embodiments 1-26 for use as a medicament.

Embodiment 35(i)

Factor VII polypeptide as defined in any one of embodiments 1-26 for use in the treatment of a coagulopathy.

Embodiment 36

Factor VII polypeptide according to embodiment 35(i) for use as a medicament in the treatment of haemophilia A or B.

The present invention is further illustrated by the following examples which, however, are not to be construed as limiting the scope of protection. The features disclosed in the foregoing description and in the following examples may, both separately and in any combination thereof, be material for realising the invention in diverse forms thereof.

EXAMPLES

Proteins

Human plasma-derived Factor X (FX) and Factor Xa (FXa) were obtained from Enzyme Research Laboratories Inc. (South Bend, Ind.). Soluble tissue factor 1-219 (sTF) or 1-209 were prepared according to published procedures (Freskgard et al., 1996). Expression and purification of recombinant wild-type FVIIa was performed as described previously (Thim et al., 1988; Persson and Nielsen, 1996). Human plasma-derived antithrombin (Baxter) was repurified by heparin sepharose chromatography (GE Healthcare) according to published procedures (Olson et al., 1993). Bovine serum albumin (BSA) was obtained from Sigma Aldrich (St. Louis, Mo.).

Example 1

FVIIa Variant Design

To design FVIIa variants with higher proteolytic activity towards FX as a substrate, a two-pronged strategy was employed. FVIIa loops and single amino acids, around the active-site area, were selected for swapping and for point mutagenesis, respectively, with corresponding FVII amino acids from different species (FIG. 1). FVIIa proteolytic activity was measured as outlined in example 5. Proteolytic activities for three loop-swapped FVIIa variants are shown in Table 1 where residues at positions 287 and 289 are mutated to threonine and glutamic acid respectively while changing the amino acid at position 288. It was observed that changes at position 288, while maintaining the same amino acids at positions 287 and 289, dramatically affected the proteolytic activity. It was also observed that substituting the amino acid at position 201 for either a leucine, carried by rat and rabbit FVII, or an arginine, carried by bovine FVII, affected the proteolytic activity. Furthermore, it was observed that substituting the amino acid at position 337 for either a glutamine carried by horse or a less bulky amino acid such as alanine affected the proteolytic activity (Table 1). These observations suggested that the amino acids at position 288 and 201 could be involved in FX recognition and activation. Therefore, positions 288 and 201 were further investigated by saturation mutagenesis and the representative results are outlined in Table 2.

TABLE 1

Proteolytic activity of selected FVIIa variants. Results are shown in percent (%) of wild-type FVIIa.

| FVIIa variant | Proteolytic activity + PS:PC (%) | Proteolytic activity + sTF + PS:PC (%) |
|---|---|---|
| FVIIa | 100 | 100 |
| FVIIa L287T L288F D289E | 100 | 22.1 |
| FVIIa L287T L288H D289E | 27.3 | 4.5 |
| FVIIa L287T L288R D289E | 3.2 | 0.7 |
| FVIIa W201L | 66.5 | 72.8 |
| FVIIa W201R | 404.5 | 177.7 |
| FVIIa K337Q | 29.8 | 63.5 |
| FVIIa K337A | 347.3 | 97.7 |
| FVIIa K337G | 317.2 | 126.1 |

Example 2

Cloning of FVIIa Variants

Mutations were introduced into a mammalian expression vector encoding FVII cDNA using a site directed mutagenesis PCR-based method using KOD Xtreme™ Hot Start DNA Polymerase from Novagen or QuickChange® Site-Directed Mutagenesis kit from Stratagene. The pQMCF expression vector and CHOEBNALT85 from Icosagen Cell Factory (Estonia) was used as expression system. Introduction of the desired mutations was verified by DNA sequencing (MWG Biotech. Germany).

Example 3

FVIIa Expression

The FVII variants were expressed in CHOEBNALT85 cells from Icosagen Cell Factory (Estonia). Briefly, CHOEBNALT85 suspension cells were transiently transfected by electroporation (Gene Pulse Xcell, Biorad, Copenhagen, DK). Transfected cells were selected with 700 µg/l Geneticin® (Gibco by Life Technologies), and expanded to give a total of 300 ml to 10 liter supernatant. Cells were cultured in medium according to manufacturer's instructions supplemented with 5 mg/l Vitamin K1 (Sigma-Aldrich). Depending on scale, cells were cultured in shake flasks (37° C. 5-8% CO2 and 85-125 rpm) or rocking cultivation bags (37° C. 5% CO2 and 30 rpm). Small scale supernatants were harvested by centrifugation followed by filtration through a 0.22 µm PES filter (Corning; Fischer Scientific Biotech, Slangerup, DK) and larger volumes were harvested by depth filtration followed by 0.22 µm absolute filtration (3 µm Clarigard, Opticap XL10; 0.22 µm Durapore, Opticap XL10, Merck Millipore, Hellerup, DK).

Example 4

FVIIa Purification and Concentration Determination

FVII variants were purified by Gla-domain directed antibody affinity chromatography essentially as described elsewhere (Thim et al. 1988). Briefly, the protocol comprised of 3 steps. In step 1, 5 mM $CaCl_2$ was added to the conditioned medium and the sample was loaded onto the affinity column. After extensive wash with 10 mM His, 2 M NaCl, 5 mM $CaCl_2$, 0.005% Tween 80, pH 6.0, bound protein was eluted with 50 mM His, 15 mM EDTA, 0.005% Tween80, pH 6.0 onto (step 2) an anion exchange column (Source 15Q, GE Healthcare). After wash with 20 mM HEPES, 20 mM NaCl, 0.005% Tween80, pH 8.0, bound protein was eluted with 20 mM HEPES, 135 mM NaCl, 10 mM $CaCl_2$, 0.005% Tween80, pH 8.0 onto (step 3) a CNBr-Sepharose Fast Flow column (GE Healthcare) to which human plasma-derived FXa had been coupled at a density of 1 mg/ml according to manufacturer's instructions. The flow rate was optimized to ensure essentially complete activation of the purified zymogen variants to the activated form. For FVIIa variants with enhanced activity, capable of auto-activation in the conditioned medium or on the anion exchange column, step 2 and/or step 3 were omitted to prevent proteolytic degradation. Purified proteins were stored at −80° C. Protein quality was assessed by SDS-PAGE analysis and the concentration of functional molecules measured by active site titration or quantification of the light chain content by rpHPLC as described below.

Measurement of FVIIa Variant Concentration by Active Site Titration

The concentration of functional molecules in the purified preparations was determined by active site titration from the irreversible loss of amidolytic activity upon titration with sub-stoichiometric levels of d-Phe-Phe-Arg-chloromethyl ketone (FFR-cmk; Bachem) essentially as described elsewhere (Bock P. E., 1992. J. Biol. Chem. 267. 14963-14973). Briefly, all proteins were diluted in assay buffer (50 mM HEPES, pH 7.4, 100 mM NaCl, 10 mM $CaCl_2$. 1 mg/mL BSA, and 0.1% w/v PEG8000). A final concentration of 150 nM FVIIa variant was preincubated with 500 nM of soluble tissue factor (sTF) for 10 min followed by the addition of FFR-cmk at final concentrations of 0-300 nM (n=2) in a total reaction volume of 100 µL in a 96-well plate. The reactions were incubated over night at room temperature. In an another 96-well plate, 20 µL of each reaction was diluted 10 times in assay buffer containing 1 mM S-2288 (Chromogenix, Milano, Italy). The absorbance increase was measured continuously for 10 min at 405 nM in a Spectramax 190 microplate spectrophotometer equipped with SOFTmax PRO software. Amidolytic activity was reported as the slope of the linear progress curves after blank subtraction. Active site concentrations were determined by extrapolation, as the minimal concentration of FFR-cmk needed to completely abolish the amidolytic activity.

Measurement of FVIIa Variant Concentration from the Light-Chain Content Using Reversed-Phase HPLC—

In an alternative approach, the concentration of functional FVIIa molecules in purified preparations were determined by quantification of the FVIIa light chain (LC) content by reversed-phase HPLC (rpHPLC). A calibration curve with wild-type FVIIa was prepared using FVIIa concentrations in the range from 0 to 3 µM, while samples of unknown concentration were prepared in estimated concentrations of 1.5 µM (n=2). All samples were reduced using a 1:1 mixture of 0.5 M tris(2-carboxyethyl)phosphine (TCEP; Calbiochem/Merck KGaA, Darmstadt, Germany) and formic acid added to the samples to a concentration of 20% (v/v) followed by heating of samples at 70° C. for 10 min. The reduced FVIIa variants were loaded onto a C4 column (Vydac. 300 Å, particle size 5 µM, 4.6 mm, 250 mm) maintained at 30° C. Mobile phases consisted of 0.09% TFA in water (solvent A) and 0.085% TFA in acetonitrile (solvent B). Following injection of 80 µL sample, the system was run isocratically at 25% solvent B for 4 min followed by a linear gradient from 25-46% B over 10 min. Peaks were detected by fluorescence using excitation and emission wavelengths of 280 and 348 nm, respectively. Light chain quantification was performed by peak integration and relative amounts of FVIIa variants were calculated on basis of the wild-type FVIIa standard curve.

Example 5

Screen for Mutations Conferring Increased Activity

As outlined in example 1, Table 1, and to evaluate the role of FVIIa amino acids at positions 201 and 288; these positions were subjected to rigorous site-directed saturation mutagenesis. In order to further identify FVIIa variants having enhanced proteolytic activity other amino acid positions, 305 and 337, were also selected for saturation mutagenesis. Briefly, activity was measured as the ability of each variant to proteolytically activate the macromolecular substrate Factor X in the presence of phospholipid vesicles (In vitro proteolysis assay). Each reaction was performed in the presence or absence of the co-factor tissue factor (sTF) to mimic the possible TF dependent and independent mechanisms of action of recombinant FVIIa. Furthermore, to understand the role of these substitutions towards FVIIa inhibition by antithrombin; antithrombin inhibition was quantified under pseudo-first order conditions in the presence of low molecular weight heparin to mimic the ability of endogenous heparin-like glycosaminoglycans (GAGs) to accelerate the reaction in vivo. These results are summarized in Table 2. As shown in FIG. 2, the measured in vitro antithrombin reactivities were found to correlate with the in vivo accumulation of FVIIa-antithrombin complexes thus validating the predictiveness of the in vitro screening procedure.

TABLE 2

Saturation mutagenesis of selected amino acid positions.
Results are shown in percent (%) of wild-type FVIIa

| FVIIa variant | Proteolytic activity + PS:PC (%) | Proteolytic activity + sTF + PS:PC (%) | AT reactivity + LMWH (%) | AT reactivity + sTF (%) |
|---|---|---|---|---|
| FVIIa W201A | 99.1 | 110.9 | 98.7 | 73 |
| FVIIa W201D | 78 | 84.2 | 72.5 | 72.7 |
| FVIIa W201E | 68.4 | 55.9 | 70.6 | 52.1 |
| FVIIa W201F | 55 | 55.5 | 113.1 | 152.5 |
| FVIIa W201H | 88.8 | 85.8 | 111.4 | 118.9 |
| FVIIa W201I | 83.5 | 85.1 | 79.3 | 104.5 |
| FVIIa W201K | 149 | 120.2 | 160.4 | 95.6 |
| FVIIa W201L | 66.5 | 72.8 | 96 | 32.7 |
| FVIIa W201M | 135.3 | 151.4 | 114.3 | 155.8 |
| FVIIa W201N | 79.1 | 56.5 | 82.9 | 64 |
| FVIIa W201P | 65.5 | 84.4 | 104.8 | 121.6 |
| FVIIa W201Q | 115.7 | 93.3 | 79.4 | 62.9 |
| FVIIa W201R | 404.5 | 177.7 | 160 | 59.6 |
| FVIIa W201S | 120.5 | 91.5 | 82.3 | 74.7 |
| FVIIa W201T | 89.5 | 74.8 | 71 | 72 |
| FVIIa W201V | 86.1 | 74.3 | 81 | 86.1 |
| FVIIa W201Y | 125.7 | 107.8 | 115 | 122.3 |
| FVIIa L288A | 206.3 | 75.1 | 112.7 | 87.9 |
| FVIIa L288D | 25.9 | 10.3 | | |
| FVIIa L288E | 91.4 | 37.7 | 77.8 | 91.5 |
| FVIIa L288F | 574.6 | 90.7 | 156.8 | 78.6 |
| FVIIa L288G | 98.4 | 44.8 | 11.6 | 37.7 |
| FVIIa L288K | 10.3 | 6.2 | 151.4 | 69 |
| FVIIa L288M | 59.9 | 47.1 | 151 | 91.8 |
| FVIIa L288N | 279.6 | 44.4 | 85.9 | 21.7 |
| FVIIa L288Q | 62.1 | 28.9 | 177.6 | 67.6 |
| FVIIa L288S | 151.2 | 57.4 | 214.7 | 91.7 |
| FVIIa L288T | 51.9 | 29.4 | 145.7 | 74.2 |
| FVIIa L288V | 35.2 | 30.8 | 98.9 | 71.5 |
| FVIIa L288W | 251.8 | 41.5 | 221.1 | 74.5 |
| FVIIa L288Y | 530.4 | 73.4 | 152.6 | 89.9 |
| FVIIa L305A | 26 | 18.8 | 31 | 28.8 |
| FVIIa L305I | 327.5 | 92.3 | 201.5 | 76.6 |
| FVIIa L305T | 34.8 | 85.9 | 42.5 | 46.1 |
| FVIIa L305V | 164.4 | 133.2 | 215.1 | 56.1 |
| FVIIa K337A | 347.3 | 97.7 | 157.4 | 128.7 |
| FVIIa K337D | 0 | 4.2 | | |
| FVIIa K337E | 20.3 | 39.2 | 3.8 | 29.9 |
| FVIIa K337G | 317.2 | 126.1 | 183.7 | 208.2 |
| FVIIa K337I | 12.3 | 34 | 1.8 | 9.5 |
| FVIIa K337L | 8.1 | 15.8 | 1.6 | 13.3 |
| FVIIa K337N | 1.5 | 12.9 | | |
| FVIIa K337Q | 29.8 | 63.5 | 30.3 | 78.2 |
| FVIIa K337S | 49.8 | 112.3 | 40.4 | 144.3 |
| FVIIa K337T | 3.9 | 16 | | |
| FVIIa K337V | 12.4 | 29.9 | 7.9 | 15.5 |
| FVIIa K337Y | 8.3 | 40.7 | | |

Amino acids including glutamine, tyrosine, methionine, lysine, and arginine at position 201 are required for gaining proteolytic activity towards FX as substrate in presence of phospholipids. W201R provides the most gain in the proteolytic activity in presence of phopholipids and in either absence or presence of sTF. On the other hand, amino acids including phenylalanine, leucine, and asparagine decrease the proteolytic activity compared to FVIIa WT. In case of position 288, alanine, asparagine, serine, tryptophan, phenylalanine, and tyrosine provide gain in the proteolytic activity towards FX as substrate in presence of phospholipids. L288F and L288Y provide the most gain in the proteolytic activity in presence of phopholipids. Data presented in Table 2 demonstrates the challenges in predicting the proteolytic activity and antithrombin reactivity a priori. Our approach of using saturation mutagenesis is, therefore, justified in order to explore the full repertoire of influence in activity that different amino acids bring about in FVIIa variants.

Measurement of Proteolytic Activity Using Factor X as Substrate (In Vitro Proteolysis Assay)—

The proteolytic activity of the FVIIa variants was estimated using plasma-derived factor X (FX) as substrate. All proteins were diluted in 50 mM HEPES pH 7.4, 100 mM NaCl, 10 mM $CaCl_2$, 1 mg/mL BSA, and 0.1% w/v PEG8000. Relative proteolytic activities were determined by incubating 1 to 10 nM of each FVIIa conjugate with 40 nM FX in the presence of 25 µM 75:25 phosphatidyl choline: phosphatidyl serine (PC:PS) phospholipids (Haematologic technologies, Vermont, USA) for 30 min at room temperature in a total reaction volume of 100 µL in a 96-well plate (n=2). FX activation in the presence of sTF was determined by incubating 5 µM of each FVIIa conjugate with 30 nM FX in the presence of 25 µM PC:PS phospholipids for 20 min at room temperature in a total reaction volume of 100 µL (n=2). After incubation, reactions were quenched by adding 100 µL of 1 mM S-2765 (Chromogenix, Milano, Italy) in stop buffer (50 mM HEPES pH 7.4, 100 mM NaCl, 80 mM EDTA). Immediately after quenching, the absorbance increase was measured continuously at 405 nM in an Envision microplate reader (PerkinElmer, Waltham, Mass.). All additions, incubations and plate movements were performed by a Hamilton Microlab Star robot (Hamilton, Bonaduz, Switzerland) on line coupled to an Envision microplate reader. Apparent catalytic rate values ($k_{cat}/K_m$) were estimated by fitting the data to a simplified form of the Michaelis Menten equation=$k_{cat}$*[S]*[E]/$K_m$) using linear regression since the FX substrate concentration ([S]) was below $K_m$ for the activation reaction. The amount of FXa generated was estimated from a standard curve prepared with human plasma-derived FXa under identical conditions. Estimated $k_{cat}/K_m$ values were reported relative to that of wild-type FVIIa following normalisation of the measured rate of FXa generation according to the concentration of the FVIIa variant used. Results are given in
Table 1,
Table 2,
Table 3 and
Table 7.

Measurement of FVIIa Inhibition by Antithrombin—

A discontinuous method was used to measure the in vitro rate of inhibition by human plasma-derived antithrombin (AT) under pseudo-first order conditions in the presence of low molecular weight (LMW) heparin (Calbiochem/Merck KGaA, Darmstadt, Germany). The assay was performed in a 96-well plate using a buffer containing 50 mM HEPES pH 7.4, 100 mM NaCl, 10 mM $CaCl_2$, 1 mg/mL BSA, and 0.1% w/v PEG8000 in a total reaction volume of 200 µL. To a mixture of 200 nM FVIIa and 12 µM LMW heparin was added 5 µM antithrombin in a final reaction volume of 100 µL. At different times, the reaction was quenched by transferring 20 µL of the reaction mixture to another microtiter plate containing 180 µL of sTF (200 nM), polybrene (0.5 mg/mL; Hexadimethrine bromide, Sigma-Aldrich) and S-2288 (1 mM). Immediately after transfer at the different times, substrate cleavage was monitored at 405 nm for 10 min in an Envision microplate reader. Pseudo-first order rate constants ($k_{obs}$) were obtained by non-linear least-squares fitting of data to an exponential decay function, and the second-order rate constant (k) was obtained from the following relationship k=$k_{obs}$/[AT]. All additions, incubations and plate movements were performed by a Hamilton Microlab Star robot (Hamilton, Bonaduz, Switzerland) on line coupled to an Envision microplate reader (PerkinElmer, Waltham, Mass.). Rates of inhibition were reported relative to that of wild-type FVIIa. Results are given in
Table 2,
Table 3 and
Table 7.

Example 6

Combining FVIIa Mutations Conferring Increased Activity and Antithrombin Resistance In order to design FVIIa variants with high proteolytic activity and antithrombin resistance, a selection of the identified FVIIa proteolytic activity enhancing variants were combined with the FVIIa variants that confer antithrombin resistance. Specifically, FVIIa combination variants were made with substitutions at positions 293 and 201, 288, 305, 337, 176 and/or 286. Characterization of the combination FVIIa purified protein preparations using the in vitro proteolysis and antithrombin inhibition assays described in Example 5 are summarized in Table 3.

Table 3 demonstrates that some combinations resulted in FVIIa variants exhibiting a desirable high activity while at the same time having a desirable low antithrombin reactivity. For example, FVIIa variant L288F T293K displayed 600% proteolytic activity in presence of phospholipids and just 6% antithrombin reactivity in presence of low-molecular weight heparin compared to wild-type FVIIa. Similarly, FVIIa variant L288Y T293K displays 447.8% proteolytic activity in presence of phospholipids and just 5.8% antithrombin reactivity in presence of low-molecular weight heparin compared to wild-type FVIIa. Furthermore, the W201R T293K displayed 609% proteolytic activity in presence of phospholipids and just 9% antithrombin reactivity in presence of low-molecular weight heparin compared to wild-type FVIIa.

Interestingly, combining the two FVIIa mutations L288F and K337A provides greatly enhanced activity with a measured 2646% increase in proteolytic activity compared to wild-type FVIIa. Upon further co-introduction of the mutation T293K, enhanced activity is retained while a low antithrombin reactivity is achieved. This variant displays 1310% proteolytic activity in presence of phospholipids and just 17% antithrombin reactivity in presence of low-molecular weight heparin compared to wild-type FVIIa.

Altogether, it can be concluded that the T293K, T293R, and T293Y mutations when combined with W201R or L288F effectively reduce the antithrombin reactivity compared to wild-type FVIIa while providing higher proteolytic activity compared to wild-type FVIIa.

TABLE 3

Proteolytic activities and antithrombin reactivities of FVIIa combination variants. Results are shown in percent (%) of wild-type FVIIa.

| FVIIa variant | Proteolytic activity + PS:PC (%) | Proteolytic activity + sTF + PS:PC (%) | AT reactivity + LMWH (%) | AT reactivity + sTF (%) |
|---|---|---|---|---|
| FVIIa W201R T293Y | 1026.9 | 202.6 | 11.1 | 2.3 |
| FVIIa W201R T293R L305I | 1573.6 | 411.3 | 46.6 | 8.9 |
| FVIIa W201R T293R | 217.2 | 375.5 | 7.1 | 9.1 |
| FVIIa W201R T293K L305I | 1734.6 | 446.4 | 82.5 | 3.4 |
| FVIIa W201R T293K | 590.6 | 272.2 | 7.9 | 7.7 |
| FVIIa W201R L288F T293R | 2542.8 | 427.2 | 40.4 | 33.2 |
| FVIIa W201R L288F T293K | 1476 | 307.2 | 16.7 | 18.2 |
| FVIIa W201M T293Y | 599.7 | 145.4 | 11.6 | 1.7 |
| FVIIa W201M T293R | 179.2 | 201.7 | 3 | 6.7 |
| FVIIa W201M T293K | 146.1 | 173.5 | 3.8 | 5.2 |
| FVIIa W201K T293Y | 617.7 | 176.7 | 15.4 | 2.6 |
| FVIIa W201K T293R | 553.5 |  | 8.8 | 11.6 |
| FVIIa W201K T293K | 217.2 | 214.6 | 6.3 | 7.3 |
| FVIIa T293Y L305V K337A | 1194.6 | 121 | 62.4 | 3.3 |
| FVIIa T293Y K337A | 213 | 162.9 | 26.5 | 2 |
| FVIIa T293R L305V K337A | 2552.5 | 427 | 37.4 | 6.9 |
| FVIIa T293R L305V | 1325.8 | 356.1 | 19.1 | 4.2 |
| FVIIa T293R L305I | 711 | 229.7 | 22.1 | 2.6 |
| FVIIa T293R K337A | 690.2 | 279 | 10.4 | 13.4 |
| FVIIa T293K L305V K337A | 956.8 | 170.1 | 34.2 | 5.7 |
| FVIIa T293K L305I | 524 | 152.2 | 17.9 | 1.7 |
| FVIIa T293K K337A | 773.1 | 264.9 | 7.2 | 6.9 |
| FVIIa L305V T293Y | 669.5 | 110.4 | 30.4 | 1.3 |
| FVIIa L305V T293K | 792.4 | 166.6 | 13.8 | 1.9 |
| FVIIa L288Y T293R K337A | 2530.2 | 323.8 | 19.1 | 10.1 |
| FVIIa L288Y T293R | 1059.7 | 298.4 | 7.5 | 4.8 |
| FVIIa L288Y T293K | 676.5 | 233.7 | 5.4 | 4.5 |
| FVIIa L288N T293Y | 783.2 | 116.2 | 10.6 | 0.8 |
| FVIIa L288N T293R | 209.5 | 78.7 | 20.7 | 3.5 |
| FVIIa L288N T293K | 168 | 69 | 4.4 | 0.9 |
| FVIIa L288F T293Y | 523.9 | 48.1 | 12.2 | 2 |
| FVIIa L288F T293R L305V | 1784.5 | 101.3 | 48.6 | 9.1 |
| FVIIa L288F T293R L305I | 1456.4 | 158.2 | 41.4 | 3.5 |
| FVIIa L288F T293R K337A | 2001.9 | 305 | 21.5 | 20.7 |
| FVIIa L288F T293R | 259.7 | 110 | 8.3 | 6.7 |
| FVIIa L288F T293K L305V | 466.3 | 181.4 | 8.2 | 10.2 |
| FVIIa L288F T293K L305I | 2147.7 | 147.6 | 33 | 2.8 |
| FVIIa L288F T293K K337A | 1310.7 | 133.6 | 17.1 | 9 |
| FVIIa L288F T293K | 600.6 | 210.2 | 6.1 | 4.3 |

Example 7

Estimation of FVIIa Potency and Plasma Level

Potencies were estimated using a commercial FVIIa specific clotting assay; STACLOT®VIIa-rTF from Diagnostica Stago. The assay is based on the method published by J. H. Morrissey et al. Blood. 81:734-744 (1993). It measures sTF initiated FVIIa activity-dependent time to fibrin clot formation in FVII deficient plasma in the presence of phospholipids. Clotting times were measured on an ACL9000 (ILS) coagulation instrument and results calculated using linear regression on a bilogarithmic scale based on a FVIIa calibration curve. The same assay was used for measurements of FVIIa clotting activity in plasma samples from animal PK studies. The lower limit of quantification (LLOQ) in plasma was estimated to 0.25 U/ml. Plasma activity levels were converted to nM using the specific activity.

Example 8

Crystallographic Analysis of FVIIa Variants

To explore the mechanism by which the identified substitutions affect proteolytic activity and antithrombin recognition, crystal structures of the representative FVIIa variants L288Y T293K, L288F T293K, W201R T293K, W201R T293Y and L288F T293K K337A were determined.

When comparing structures on the 3-dimensional level the 1 DAN structure of wild-type (WT) FVIIa, in complex with soluble Tissue Factor, [Banner, D. W. et al, Nature, (1996), Vol. 380, 41-46] have had its heavy chain residues of FVIIa renumbered according to the numbering scheme of SEQ ID NO: 1.

Purified H-$_D$-Phe-Phe-Arg chloromethyl ketone (FFR-cmk; Bachem, Switzerland) active-site inhibited FVIIa variants in complex with soluble Tissue Factor (fragment 1-219) were crystallized using the hanging drop method in accordance with [Kirchhofer, D. et al, Proteins Structure Function and Genetics, (1995), Vol. 22, pages 419-425]. The protein buffer solution was a mix of 10 mM Tris pH 7.5 at 25 C.°, 100 mM NaCl, 15 mM CaCl$_2$. Protein concentrations together with precipitant solutions and mixing conditions for the FVIIa variants are shown in Table 4. The hanging drop method using 24-well VDX-plates and well solution of 1.0 ml was utilized. The drops were set up with a mix of 1.5 µl of the protein solution and 0.5 µl of the well solution. Streak seeding was used to initialize nucleation.

The cryo conditions are shown in

Table 4. The crystal was let to soak in the cryo solution for about 30 seconds after which the crystal was transferred to, and flash frozen in, liquid nitrogen. Crystallographic data were processed by the XDS data reduction software [Kabsch, W., Acta Crystallographica Section D Biological Crystallography, (2010), Vol. 66, pages 125-132] using resolution cut-off as described by Karplus et al. [Karplus, P. A. et al, Science (New York, N.Y.), (2012), Vol. 336, pages 1030-1033].

TABLE 4

Crystallization and freezing conditions for the FVIIa variants.

| FVIIa variant | Protein conc. | Precipitant solution | Mixing ratio protein: precipitant solution | Cryo condition |
|---|---|---|---|---|
| L288Y T293K | 2.5 mg/ml | 0.1M Cacodylate pH 5.1, 13% Peg 8000 | 3:1 | 100% TMAO (trimethylamine N-oxide) |
| L288F T293K | 2.14 mg/ml | 0.1M Na-citrate pH 5.6, 17% Peg 3350 and 12% 1-propanol | 3:1 | 100% TMAO |
| W201R T293K | 1.0 mg/ml | 0.1M Cacodylate pH 5.1, 13% Peg 8000 | 3:1 | As precipitant solution but with 35% PEG 8000 |
| W201R T293Y | 2.93 mg/ml | 0.1M Cacodylate pH 5.1, 12% Peg 8000 | 3:1 | As precipitant solution but with 35% PEG 8000 |
| L288F T293K K337A | 1.0 mg/ml | 0.1M Na-citrate pH 5.6, 16% Peg 3350 and 12% 1-propanol | 3:1 | As precipitant solution but with 35% PEG3350. |

In-house generated coordinates (unpublished) based on the crystallographic coordinates of the 1DAN entry [Banner, D. W. et al, Nature, (1996), Vol. 380, pages 41-46] from the Protein Data Bank (PDB) [Berman, H. M. et al, Nucleic Acids Res., (2000), Vol. 28, pages 235-242], were used as starting model for either molecular replacement calculations in phenix.phaser [Mccoy, A. J. et al, J. Appl. Crystallogr., (2007), Vol. 40, pages 658-674] or straight into refinements with the phenix.refine software [Afonine, P. V. et al, Acta Crystallogr. Sect. D-Biol. Crystallogr., (2012), Vol. 68, pages 352-367] of the PHENIX software package [Adams, P. D. et al, Acta Cryst. D, (2010), Vol. 66, pages 213-221]. Refinements were followed by interactive model corrections in the computer graphics software COOT [Emsley, P. et al, Acta Crystallogr. Sect. D-Biol. Crystallogr., (2010), Vol. 66, pages 486-501]. Crystallographic data, refinement and model statistics for the 5 FVIIa variants are shown in Table 5.

TABLE 5

Data collection, refinement and model statistics.
Statistics for the highest-resolution shell are shown in parentheses.

| FVIIa variant | L288Y T293K | L288F T293K | W201R T293K | W201R T293Y | L288F T293K K337A |
|---|---|---|---|---|---|
| Data collection beamline | BLI911-3, MAX-lab | BLI911-3, MAX-lab | BLI911-3, MAX-lab | BLI911-3, MAX-lab | X10SA, SLS |
| Wavelength [Å] | 1.0000 | 1.0000 | 1.0000 | 1.0000 | 0.9999 |
| Resolution range [Å] | 35.7-2.01 (2.082-2.01) | 29.25-2.37 (2.455-2.37) | 29.5-1.71 (1.772-1.71) | 29.16-2.5 (2.589-2.5) | 49.75-2.216 (2.295-2.216) |
| Space group | P 2$_1$ 2$_1$ 2$_1$ | P 2$_1$ 2$_1$ 2$_1$ | P 2$_1$ 2$_1$ 2$_1$ | P 2$_1$ 2$_1$ 2$_1$ | P 2$_1$ 2$_1$ 2$_1$ |
| Unit cell [Å] | 71.34 82.46 123.3 | 69.34 81.57 125.88 | 68.77 78.2 172.21 | 68.86 81.42 125.39 | 68.919 81.545 125.57 |
| Total reflections | 321033 (9043) | 103617 (6525) | 501348 (14728) | 91616 (9007) | 234709 (20365) |
| Unique reflections | 48292 (4010) | 28995 (2424) | 96329 (6505) | 24966 (2433) | 35724 (3412) |
| Multiplicity | 6.6 (2.3) | 3.6 (2.7) | 5.2 (2.3) | 3.7 (3.7) | 6.6 (6.0) |
| Completeness [%] | 98.31 (83.26) | 97.71 (83.50) | 95.43 (63.97) | 99.70 (99.43) | 99.60 (96.82) |
| Mean I/sigma(I) | 9.33 (0.68) | 9.45 (0.79) | 11.73 (0.42) | 5.09 (0.54) | 7.39 (0.53) |
| Wilson B-factor [Å] | 22.18 | 40.30 | 24.56 | 25.91 | 45.71 |
| R-merge | 0.2439 (1.316) | 0.145 (1.431) | 0.1141 (1.968) | 0.3456 (2.778) | 0.2599 (3.739) |
| R-meas | 0.2647 | 0.1698 | 0.1266 | 0.4047 | 0.2822 |
| CC1/2 | 0.987 (0.277) | 0.992 (0.322) | 0.997 (0.219) | 0.951 (0.11) | 0.992 (0.174) |
| CC* | 0.997 (0.659) | 0.998 (0.698) | 0.999 (0.599) | 0.987 (0.446) | 0.998 (0.545) |
| Reflections used in refinement | 48286 | 28991 | 96323 | 24966 | 35721 |
| Reflections used for R-free | 2497 | 1465 | 4773 | 1260 | 1853 |
| R-work | 0.2122 (0.3487) | 0.2199 (0.3698) | 0.2170 (0.5007) | 0.2568 (0.3940) | 0.2077 (0.4038) |
| R-free | 0.2561 (0.3880) | 0.2755 (0.3826) | 0.2556 (0.5132) | 0.3102 (0.4015) | 0.2556 (0.4045) |
| Number of non-hydrogen atoms: Total | 5446 | 4969 | 5382 | 4981 | 4566 |
| In Macro-molecules | 4769 | 4700 | 4836 | 4679 | 4355 |
| In Ligands | 81 | 51 | 87 | 36 | 39 |
| In Waters | 596 | 218 | 459 | 266 | 172 |
| Protein residues | 607 | 618 | 622 | 607 | 561 |
| RMS(bonds) [Å] | 0.007 | 0.004 | 0.008 | 0.002 | 0.005 |
| RMS(angles) [°] | 0.88 | 0.64 | 1.05 | 2.73 | 0.75 |
| Ramachandran favoured [%] | 97 | 94 | 94 | 94 | 95 |
| Ramachandran outliers [%] | 0 | 0 | 0.99 | 0.51 | 0 |

TABLE 5-continued

Data collection, refinement and model statistics.
Statistics for the highest-resolution shell are shown in parentheses.

| FVIIa variant | L288Y T293K | L288F T293K | W201R T293K | W201R T293Y | L288F T293K K337A |
|---|---|---|---|---|---|
| Clashscore | 1.69 | 1.41 | 3.60 | 2.19 | 1.74 |
| Average B-factor [Å$^2$]: Total | 30.70 | 51.70 | 60.40 | 43.70 | 61.80 |
| For macromolecules | 29.70 | 51.90 | 61.50 | 44.80 | 61.80 |
| For Ligands | 56.10 | 65.60 | 68.50 | 43.60 | 109.30 |
| For Solvent | 35.30 | 44.70 | 46.70 | 23.60 | 50.10 |

3-Dimensional Structure Analyses

Generally there are no major differences between the wild type (WT) FVIIa molecule 1DAN structure [Banner, D. W. et al, Nature, (1996), Vol. 380, pages 41-46] and those of the FVIIa variants. The overall root-mean-square deviation (RMSD), calculated by gesamt [Krissinel, E., Journal of Molecular Biochemistry, (2012), Vol. 1, pages 76-85] between the 1DAN FVIIa heavy chain and the L288Y T293K, L288F T293K, W201R T293K, W201R T293Y and L288F T293K K337A FVIIa variants are 0.424, 0.365, 0.451, 0.342 and 0.289 Å, respectively. The number of $C_\alpha$-atom pairs used in the calculations were 254, 254, 251, 254 and 254, respectively.

The W201R T293Y FVIIa Variant
Mutation FVIIa W201R:

On the detailed level the heavy chain FVIIa Arg 201 residue of the double mutant is situated in the "60-loop" (chymotrypsin numbering). In the likelihood-weighted 2mFo-DFc electron density map, at 1.0 σ cut-off, there are indications of the main chain loop stretch while that cannot be seen for the side chains of the Arg 201 residue (a Trp residue in the wild type FVIIa), together with the side chain of the residues before and after (Asn and Arg residues, respectively). This indicates high flexibility of those side chains. To aid in the structure interpretation a difference electron density map was calculated between observed structure factors from the in-house wild type protein crystals and the observed structure factors from the FVIIa double mutant [$F_{obs}$(WT FVIIa/sTF)-$F_{obs}$(FVIIa W201R T293Y/sTF)], using software from the CCP4 software program package [Collaborative Computational Project, N. Acta crystallographica, Section D, Biological crystallography, 1994, 50, 760-763]. Using phases from the wild type data or the double mutant data resulted in similar difference maps. On the positive side of the difference map the side chain of the Trp residue from the wild type FVIIa can be clearly seen (maximum peak at 5.6 σ levels using phases from wild type data) while there is no clear indication of the Arg side chain on the negative side of the difference map. This also argues for that the Arg residue is more flexible than the Trp residue of the wild type protein. It should be noted, however, that neither the side chains before nor after the Trp residue can be clearly observed in the 1 DAN structure, using a likelihood-weighted 2mFo-DFc electron density map, which is similar to the results from the FVIIa W201R T293Y/sTF crystal structure, while the position of the Trp 201 is unmistakably seen in the FVIIa WT structure.

Regarding the main chain orientation of the loop studied, the likelihood-weighted 2mFo-DFc electron density map and phenix.refine refinements places the 200, 201 and 202 residues closer towards the position of the replaced Trp side chain residue, relatively to the published 1DAN structure [Banner. D. W., et al., Nature, 1996, 380, 41-46]. In particular residue Asn 200 has moved and its $C_\alpha$ position is 3.1 Å away from its position in the wild type structure FIG. 3. Also, in the described [$F_{obs}$(WT FVIIa/sTF)-$F_{obs}$(FVIIa W201R T293Y/sTF)] difference map there are peaks indicating such a movement of residue Asn 200. One 5.7 σ positive peak close to the position of the wild type loop conformation and another 4.3 σ negative peak slightly on the inside of the refined double mutant conformation. This supports that the main chain has moved closer towards the position of the WT Trp side chain and relatively more towards the center of the FVIIa heavy chain.

The structural difference seen between the wild type structure and the double mutated protein for the residues 200, 201 and 202 of the heavy chain FVIIa probably depends on stabilization by the inward pointing Trp 201 residue side chain in the WT structure that fills out a primarily hydrophobic volume in the FVIIa protein and thereby anchors the loop in the wild type structure. The side chain of the corresponding residue Arg in FVIIa W201R T293Y does not form the same rigid structure, with a tightly bound side chain, but is more flexible, and therefore not anchoring the loop in the same way as in the WT FVIIa structure.

Figure 3:
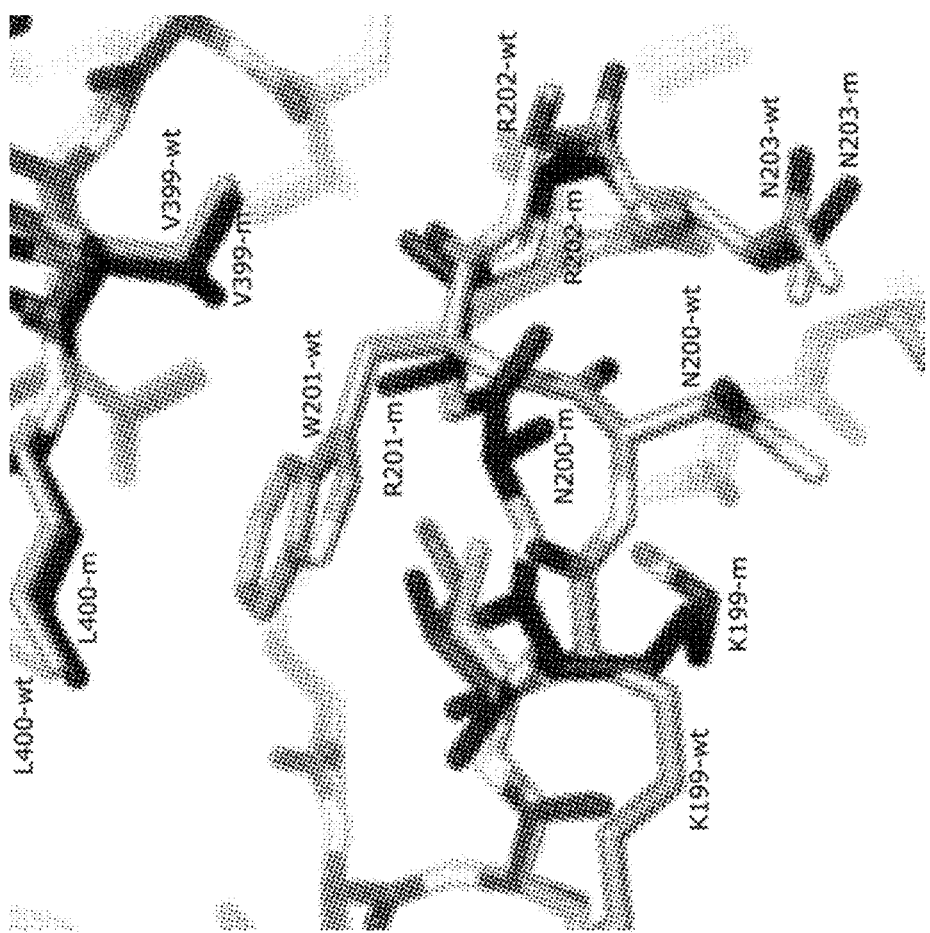
FIG. 3 shows the conformation of arginine at position 201 in the FVIIa variant W201R T293Y double mutant compared to the conformation of tryptophan at position 201 in FVIIa WT.

FIG. 3 shows a stick representation of a comparison of the two crystal structures: 1) with light-colored carbon atoms. FVIIa wild type protein in complex with Tissue Factor, using an in-house data set from crystals of the same type as the PDB structure 1 DAN [Banner. D. W., et al., Nature, 1996, 380, 41-46], and 2) with dark-colored carbon atoms, the FVIIa double mutant W201R T293Y in complex with Tissue Factor. Some of the residues are labeled with amino acid one-letter code and ending with "-wt" or "-m" for 1) and 2), respectively. Several side chains have been truncated (atoms outside of $C_\beta$ have been removed) as likelihood-weighted 2mFo-DFc electron density maps did not show any electron density for those side chains. For example the residues N200, R201 and R202 of the FVIIa double mutant W201R T293Y are all truncated for that reason. The figure was prepared by the molecular graphics software PyMOL [The PyMOL Molecular Graphics System. Version 1.6.0.0 Schrödinger, LLC].

Mutation FVIIa T293Y:

The heavy chain FVIIa Tyr 293 residue is situated in the activation loop 1. The likelihood-weighted 2mFo-DFc electron density map, at 1.0 σ cut-off, clearly show the main chain and side chain of the Tyr residue in the refined structure. The Tyr side chain atom $C_\beta$ $C_\gamma$ follows the same direction as for the $C_\beta$-$C_{\gamma 2}$ atoms in the wild type Thr residue. The C-$C_\alpha$-$C_\beta$-$C_\gamma$ and C-$C_\alpha$-$C_\beta$-$C_{\gamma 2}$ dihedral angles are 165 and 173° for FVIIa residue 293 of the double mutant and WT form, respectively. Thereby, the Tyr 293 residue of the double mutant directs its side chain in the direction of the catalytic domain and towards the binding site of the FFR-cmk bound inhibitor. The calculated [$F_{obs}$(WT FVIIa/sTF)-$F_{obs}$(FVIIa W201R T293Y/sTF)] difference map confirms the orientation of the Tyr side chain with a negative peak (4.7 σ height) at the Tyr ring system and a positive peak (4.2 σ height) at the missing Thr O$\gamma_1$ atom.

To study the possible interactions between antithrombin and a FVIIa mutated T293Y molecule a superimposition of the Factor Xa molecular complex with antithrombin, PDB-code 2GD4 [Johnson. D. J. D., et al., Embo J., 2006, 25, 2029-2037], was made on the FVIIa double mutant. The molecular graphics software PyMOL [The PyMOL Molecular Graphics System, Version 1.6.0.0 Schrödinger, LLC] was used for the superimposition of the FXa and FVIIa molecules and resulted in an RMSD of 0.769 Å for 1194 atoms. From the riding antithrombin molecule model it is then clear that the Tyr 293 residue of the FVIIa W201R T293Y mutant in the theoretically molecular complex produced (FVIIa W201R T293Y/antithrombin III) forms spatial overlap with, in particular, residue Leu 395 but also Arg 399 of the antithrombin molecule FIG. 4. This is confirmed by distance calculations, performed in the contacts software of the CCP4 program suite, between Tyr 293 of the FVIIa double mutant and the riding antithrombin molecule. A cut-off distance of 3.5 Å was used between the Tyr 293 residue in the mutant FVIIa molecule and the antithrombin molecule and the results are shown in Table 6. All distances, 3.5 Å or shorter, between the residue Tyr 293 of the FVIIa W201R T293Y double mutant and antithrombin from the Antithrombin-S195A FXa-pentasaccharide complex, PDB:2GD4, [Johnson. D. J. D., et al., Embo J., 2006, 25, 2029-2037] after the FXa complex has been superimposed on the FVIIa mutant (W201R T293Y)/sTF structure, using the FVIIa (W201R T293Y) and the FXa as common molecules are summarized in Table 6. The spatial overlap will most probably negatively influence on the possibility for antithrombin to place its reactive center loop (RCL) into the active site of FVIIa. Thereby a T293Y mutated FVIIa molecule will be less susceptible to inhibition by antithrombin. This is in agreement with, and gives an explanation to, what is observed experimentally showing increased resistance to inactivation by antithrombin and prolonged half-life.

Figure 4:
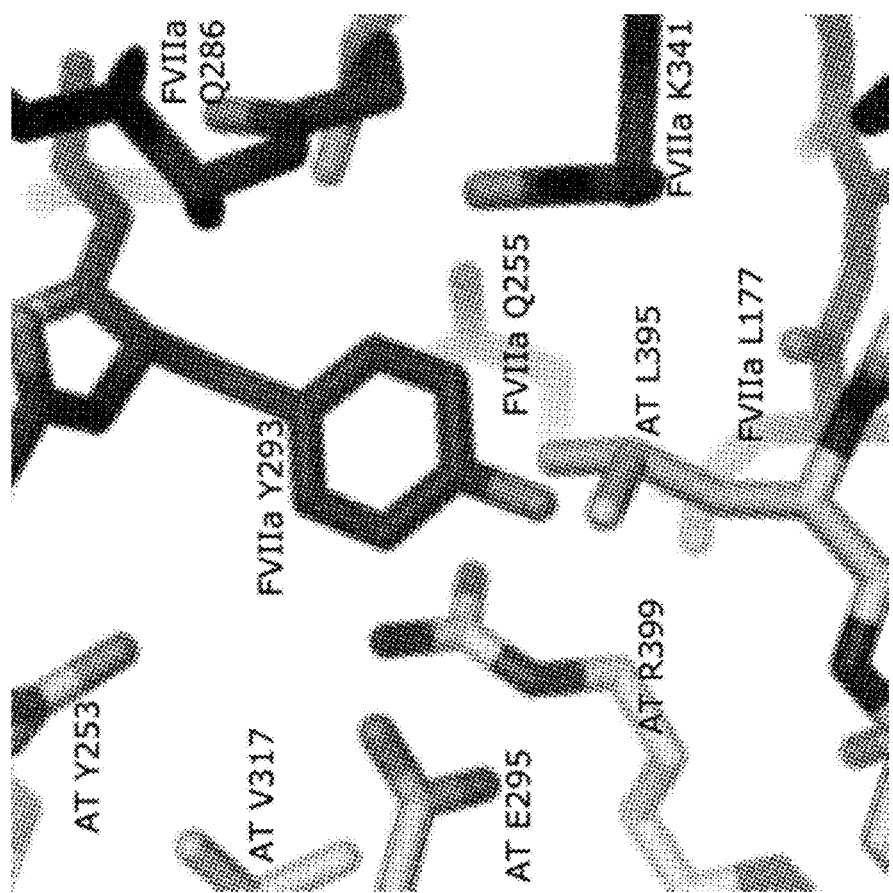
FIG. 4 shows a hypothetical model of interaction between tyrosine at position 293 from the FVIIa variant W201R T293Y double mutant with the antithrombin. This is based on a theoretical model of a complex between antithrombin and the FVIIa variant W201R T293Y double mutant shown in stick representation. Antithrombin amino acids are depicted with a prefix "AT"; while, the FVIIa amino acids are depicted with a prefix "FVIIa".

FIG. 4 is a stick representation of a theoretical model of a complex between antithrombin (indicated with light carbon atoms) and the FVIIa W201R T293Y double mutant (indicated with dark carbon atoms). The relative positions of the residues Tyr 293, Gln 255, Lys 341, Gln 286 of the FVIIa mutant W201R T293Y, and for the antithrombin molecule residues Leu 395, Arg 399, Glu 295, Tyr 253 and V317 are shown and labeled. The model was constructed based on the structures of the antithrombin/FXa complex [Johnson. D. J. D., et al., Embo J., 2006, 25, 2029-2037], PDB code 2GD4, where the FXa molecule, with the antithrombin let riding, has been superimposed on the heavy chain of FVIIa W201R T293Y variant molecule. Residues of FVIIa W201R T293Y and antithrombin have a prefix of "FVIIa" and "AT" respectively, followed by one-letter amino acid code and residue number. The figure was prepared by the molecular graphics software PyMOL [The PyMOL Molecular Graphics System, Version 1.6.0.0 Schrödinger, LLC].

TABLE 6

All distances. 3.5 Å or shorter between the residue Tyr 293 of the FVIIa (W201R T293Y) double mutant and antithrombin amino acids in the described theoretical model between the two molecules.

| FVIIa W201R T293Y | | | Antithrombin | | | |
|---|---|---|---|---|---|---|
| Res. Type | Res. # and Chain | Atom name | Res. Type | Res. # and Chain | Atom name | Distance [Å] |
| Tyr | 293H | N | Tyr | 253A | OH | 3.41 |
| Tyr | 293H | CD1 | Leu | 395A | CD1 | 3.07 |
| Tyr | 293H | CD2 | Tyr | 253A | OH | 3.50 |
| | | | Arg | 399A | NH2 | 2.54 |
| | | | Arg | 399A | CZ | 3.40 |
| Tyr | 293H | CE1 | Leu | 395A | CG | 2.88 |
| | | | Leu | 395A | CD1 | 1.89 |
| | | | Leu | 395A | CD2 | 3.40 |
| Tyr | 293H | CE2 | Glu | 255A | OE2 | 3.11 |
| | | | Arg | 399A | NH2 | 2.24 |
| | | | Leu | 395A | CD1 | 2.72 |
| | | | Arg | 399A | CZ | 2.90 |
| Tyr | 293H | CZ | Arg | 399A | NH2 | 3.26 |
| | | | Leu | 395A | CG | 2.51 |
| | | | Leu | 395A | CD1 | 1.60 |
| | | | Arg | 399A | CZ | 3.43 |
| | | | Leu | 395A | CD2 | 2.59 |
| Tyr | 293H | OH | Leu | 395A | CB | 2.78 |
| | | | Leu | 395A | CG | 1.53 |
| | | | Leu | 395A | CD1 | 1.54 |
| | | | Leu | 395A | CD2 | 1.26 |

The W201R T293K FVIIa Variant

The region around residue 201 of FVIIa: On a detailed level the heavy chain FVIIa Arg 201 residue of the double mutant is situated in the "60-loop" (chymotrypsin numbering). In the likelihood-weighted 2mFo-DFc electron density map, at 1.0 σ cut-off, the main chain loop stretch is clearly seen. The side chain of the Arg 201 residue (a Trp residue in the wild type FVIIa) is also clearly observed. The outer part, the guanidinium group, of the Arg 202 residue has, however, missing electron density in the likelihood-weighted 2mFo-DFc electron density map and at the chosen cut-off, indicating a higher mobility or disorder. Regarding the main chain orientation of the loop studied (the "60-loop") it show transformations between the W201R T293K and the 1DAN structure [Banner, D. W. et al, Nature, (1996), Vol. 380, pages 41-46]. After superimposing the two structures it is seen that when moving along the polypeptide from residue 197 towards 203 there are differences in equivalent $C_\alpha$ positions by 0.64, 2.48, 3.63, 6.41, 4.15 and 0.81 Å, respectively. The main chain of the loop has moved closer towards the position of the in 1 DAN WT Trp side chain position [Banner, D. W. et al, Nature, (1996), Vol. 380, pages 41-46] and has also moved towards the center of the FVIIa heavy chain, the catalytic domain. The Arg 201 residue of W201R T293K FVIIa is in the superimposed structure placed towards the position of the replaced WT Trp side chain residue of the published 1DAN structure.

The structural difference seen between the wild type structure and the W201R T293K FVIIa variant of the heavy chain "60-loop" probably depends on stabilization by the inward pointing Trp 201 residue side chain in the WT structure that fills out a primarily hydrophobic volume in the FVIIa protein and thereby anchors the loop in the wild type structure. The side chain of the corresponding, smaller, residue Arg in FVIIa W201R T293K does not anchor the loop in the same way as the Trp in the WT FVIIa structure.

The Region Around Residue 293 of FVIIa:

The heavy chain FVIIa Lys 293 residue is situated in the activation loop 1. The likelihood-weighted 2mFo-DFc electron density map, at 1.0 σ cut-off, clearly show the main chain and side chain of the Lys residue in the refined structure. The Lys side chain atom $C_\beta$-$C_\gamma$ follows the same direction as for the $C_\beta$-$C_{\gamma2}$ atoms in the wild type Thr residue. The C-$C_\alpha$-$C_\beta$-$C_\gamma$ and C-$C_\alpha$-$C_\beta$-$C_{\gamma2}$ dihedral angles are 169 and 173° for FVIIa residue 293 of the double mutant and WT form, respectively. The Lys 293 show a "mttt" rotamer orientation, the most common rotamer orientation for Lys [Lovell, S. C. et al, Proteins, (2000), Vol. 40, pages 389-408] as seen by the computer graphics software COOT [Emsley, P. et al, Acta Crystallogr. Sect. D-Biol. Crystallogr., (2010), Vol. 66, pages 486-501]. Moreover, the Lys 293 residue $N_\zeta$ atom of the W201R T293K FVIIa variant makes a strong, with a distance of 2.68 Å, hydrogen bond with the residue Gln 176 $O_{\epsilon1}$ atom thereby stabilizing the two side chains. Compared to the WT FVIIa 1DAN structure the Gln 176 residue has therefore altered its side chain conformation to optimize the hydrogen bond it makes with the Lys 293 residue in the W201R T293K FVIIa variant. The rotamer goes from the "tt0°" conformation of the WT structure to a rotamer conformation which is not among the standard conformations described in [Lovell, S. C. et al, Proteins, (2000), Vol. 40, pages 389-408]. Thereby, the Lys 293 residue of the double mutant directs its side chain in the direction of the catalytic domain and towards the binding site of the FFR-cmk bound inhibitor and is filling out a prime site of the FVIIa active site cleft.

The L288Y T293K FVIIa Variant
The Region Around Residue 288 of FVIIa:

The region is clearly seen in the crystal structure likelihood-weighted 2mFo-DFc electron density map, at a 1.0 σ cut-off. The residues in the loop following the Tyr 288 residue, residues 289 to 292 in the heavy chain of the FVIIa L288Y T293K FVIIa variant shows a change in main chain conformation with a maximum difference at residue Arg 290 where the $C_\alpha$ atoms differs 2.87 Å between the a superimposed molecules of the FVIIa L288Y T293K FVIIa variant and the WT structure of FVIIa, 1DAN [Banner, D. W. et al, Nature, (1996), Vol. 380, pages 41-46]. The $C_\alpha$ atom of the Tyr 288 residue shows a 0.80 Å difference to the equivalent atom of the Leu 288 residue in the superimposed WT FVIIa. The side chain rotamer of Tyr 288 in the FVIIa L288Y T293K FVIIa variant is "p90°" while that of the Ley side chain rotamer of the WT FVIIa 1DAN structure show a "mt" rotamer [Lovell, S. C. et al, Proteins, (2000), Vol. 40, pages 389-408]. That results in that the two equivalent side chains points in different directions, seen in the difference in the C-$C_\alpha$-$C_\beta$-$C_\gamma$ dihedral angle, −69° and 157° for the L288Y T293K FVIIa variant and WT FVIIa, respectively. The hydroxyl group of the Tyr 288 side chain in the L288Y T293K FVIIa variant interacts favorably with surrounding water molecules, which are ordered in the crystal structure and the side chain folds over the loop following the Tyr 288 of the FVIIa L288Y T293K variant. The structural main chain alteration of the loop following residue 288, and the mutation of residue 288 itself, might at least partly explain the activity improvements seen of this FVIIa variant.

The Region Around Residue 293 of FVIIa:

The 3D structure of this residue and other residues in contact with it highly similar to what is described for the W201R T293K FVIIa variant. Therefore all conclusions drawn for the T293K mutation of that variant also applies to the of T293K mutation of the L288Y T293K FVIIa variant.

The L288F T293K FVIIa Variant
The Region Around Residue 288 of FVIIa:

The region is clearly seen in the crystal structure likelihood-weighted 2mFo-DFc electron density map, at a 1.0 σ cut-off. The 3D structure of this region is highly similar to the L288F T293K FVIIa variant. The two variants share same main chain orientation for example. One thing that differs between the two FVIIa variants is that the Phe 288 side chain has another preferred rotamer ("m-85°") for its side chain, actually pointing in the same orientation as the Leu 288 side chain of the WT FVIIa. An unusual property of the Phe 288 side chain of the L288F T293K FVIIa variant is that for Phe residues it is unusually exposed (145 Å$^2$ according to calculations by AREAIMOL of the CCP4 crystallographic program suite [Bailey, S., Acta Crystallogr. Sect. D-Biol. Crystallogr., (1994), Vol. 50, pages 760-763]) to the surrounding solvent.

The Region Around Residue 293 of FVIIa:

The 3D structure of this residue and other residues in contact with it is highly similar to what is described for the W201R T293K FVIIa variant. Therefore all conclusions drawn for the T293K mutation of that variant also applies to the of T293K mutation of the L288F T293K FVIIa variant.

The L288F T293K K337A FVIIa Variant
The Region Around Residue 288 of FVIIa:

The region is clearly seen in the crystal structure likelihood-weighted 2mFo-DFc electron density map, at a 1.0 σ cut-off. The 3D structure of this region is highly similar to the L288F T293K FVIIa variant. The two variants share same main chain orientation for example. One thing that differs between the two FVIIa variants is that the Phe 288 side chain has another preferred rotamer ("m-85°") for its side chain, actually pointing in the same orientation as the Leu 288 side chain of the WT FVIIa and the L288F T293K FVIIa variant. Therefore all conclusions drawn for the L288F mutation of that variant also applies to the of L288F mutation of the L288F T293K K337A FVIIa variant.

The Region Around Residue 293 of FVIIa:

The 3D structure of this residue and other residues in contact with it highly similar to what is described for the W201R T293K FVIIa variant. Therefore all conclusions drawn for the T293K mutation of that variant also applies to the of T293K mutation of the L288F T293K K337A FVIIa variant.

The Region Around Residue 337 of FVIIa:

The region is clearly observed in the crystal structure likelihood-weighted 2mFo-DFc electron density map, at a 1.0 σ cut-off. The 3D structure of this region is similar to the WT structure of FVIIa, 1DAN [Banner, D. W. et al, Nature, (1996), Vol. 380, pages 41-46], and to the other FVIIa variants of this Example. The overall main- and side-chain orientations are close to the WT FVIIa 1 DAN structure and the other FVIIa variant structures there are, however, small differences, slightly larger than the by phenix.refine maximum-likelihood based calculation of the coordinate error of 0.40 Å of the crystal structure. The equivalent $C_\beta$ atoms of residue 337 are 0.8 Å apart in WT structure of FVIIa, 1DAN, and the L288F T293K K337A FVIIa variant. The $C_\alpha$ atoms of the same residues are 0.4 Å apart. The equivalent $C_\alpha$ atoms of residue 336 are 0.6 Å apart in the superimposed WT structure of FVIIa, 1DAN, and the L288F T293K K337A FVIIa variant. For the Phe 332 residue the side chain is shifted approximately 0.5 Å towards the Ala 337 residue of the L288F T293K K337A FVIIa variant compared to the WT structure of FVIIa, 1DAN [Banner, D. W. et al, Nature, (1996), Vol. 380, pages 41-46]. It can also be concluded that the other FVIIa variants of this Example show approximately the same deviation to the L288F T293K K337A FVIIa variant as the WT structure of FVIIa 1 DAN does. Moreover the other FVIIa variants cluster much closer to the WT FVIIa 1 DAN structure than the L288F T293K K337A FVIIa variant does. This might explain at least in part the altered properties of this variant.

Examples 9-14

Chemical Modification of FVIIa Variants

Abbreviations Used in Examples 9-14:
AUS: Arthrobacter ureafaciens Sialydase
CMP-NAN: Cylidine-5'-monophosphate-N-acetyl neuraminic acid
CV: Column volume
GlcUA: Glucuronic acid
GlcNAc: N-Acetylglucosamine
GSC: 5'-Glycylsialic acid cytidine monophosphate
GSC-SH: 5'-[(4-Mercaptobutanoyl)glycyl]sialic acid cytidine monophosphate
HEP: HEParosan polymer
HEP-GSC: GSC-functionalized heparosan polymer
HEP-[N]-FVIIa: HEParosan conjugated via N-glycan to FVIIa.
HEPES: 2-[4-(2-hydroxyethyl)piperazin-1-yl]ethanesulfonic acid
His: Histidine
PABA: p-Aminobenzamidine
ST3GalIII N-glycan specific a2,3-sialyltransferase
TCEP: tris(2-carboxyethyl)phosphine
UDP: Uridine diphosphate
Quantification Method Used in Examples 9-14:
The conjugates of the invention were analysed for purity by HPLC. HPLC was also used to quantify amount of isolated conjugate based on a FVIIa reference molecule. Samples were analysed either in non-reduced or reduced form. A Zorbax 300SB-C3 column (4.6×50 mm; 3.5 μm Agilent, Cat. No.: 865973-909) was used. Column was operated at 30° C. 5 μg sample was injected, and column eluted with a water (A)—acetonitrile (B) solvent system containing 0.1% trifluoroacetic acid. The gradient program was as follows: 0 min (25% B); 4 min (25% B); 14 min (46% B); 35 min (52% B); 40 min (90% B); 40.1 min (25% B). Reduced samples were prepared by adding 10 μl TCEP/formic acid solution (70 mM tris(2-carboxyethyl)phosphine and 10% formic acid in water) to 25 μl/30 μg FVIIa (or conjugate). Reactions were left for 10 minutes at 70° C., before they were analysed on HPLC (5 μl injection).
Starting Materials Used in Examples 9-14:
HEP-Maleimide and HEP-Benzaldehyde Polymers
Maleimide and aldehyde functionalized HEP polymers of defined size is prepared by an enzymatic polymerization reaction as described in US 2010/0036001. Two sugar nucleotides (UDP-GlcNAc and UDP-GlcUA) and a priming trisaccharide (GlcUA-GlcNAc-GlcUA)NH₂ for initiating the reaction is used, and polymerization is run until depletion of sugar nucleotide building blocks. The process produced HEP polymers with a single terminal amino group. The size of HEP polymer is determined by the sugar nucleotide to primer ratio. The terminal amine (originating from the primer) is then functionalized with either a maleimide functionality for conjugation to GSC-SH, or a benzaldehyde functionality for reductive amination chemistry to the glycyl terminal of GSC.

HEP-benzaldehydes can be prepared by reacting amine functionalized HEP polymers with a surplus of N-succinimidyl-4-formylbenzoic acid (Nano Letters (2007), 7(8), 2207-2210) in aqueous neutral solution. The benzaldehyde functionalized polymers may be isolated by ion-exchange chromatography, size exclusion chromatography, or HPLC. HEP-maleimides can be prepared by reacting amine functionalized HEP polymers with a surplus of N-maleimidobutyryl-oxysuccinimide ester (GMBS; Fujiwara, K., et al. (1988), *J. Immunol. Meth.* 112, 77-83).

The benzaldehyde or maleimide functionalized polymers may be isolated by ion-exchange chromatography, size exclusion chromatography, or HPLC. Any HEP polymer functionalized with a terminal primary amine functionality (HEP-NH₂) may be used in the present examples. Two options are shown below:

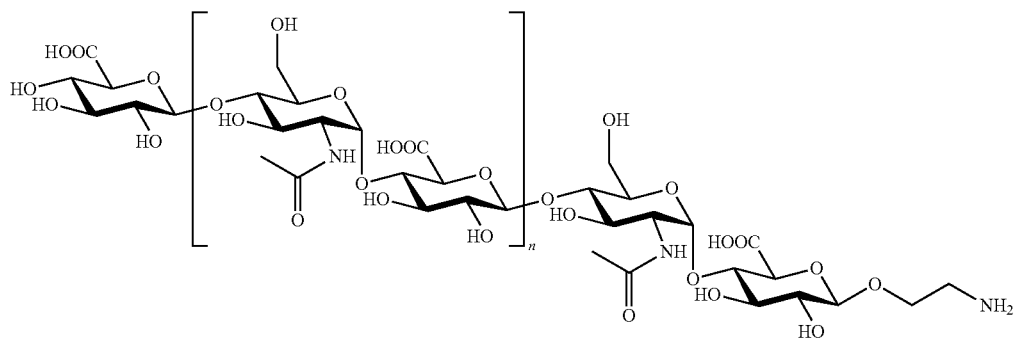

-continued

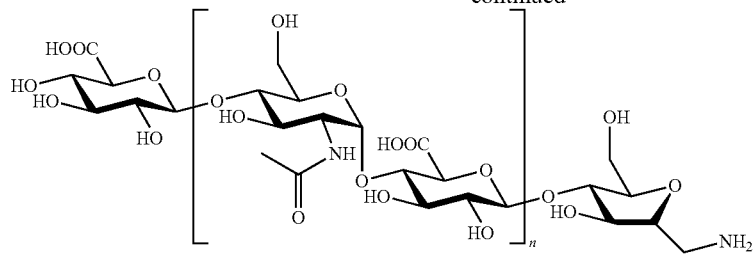

The terminal sugar residue in the non-reducing end of the polysaccharide can be either N-acetylglucosamine or glucuronic acid (glucuronic acid is drawn above). Typically a mixture of both sugar residues are to be expected in the non-reducing end, if equimolar amount of UDP-GlcNAc and UDP-GlcUA has been used in the polymerization reaction.

5'-Glycylsialic Acid Cytidine Monophosphate (GSC)

The GSC starting material used in the current invention can be synthesised chemically (Dufner, G. Eur. J. Org. Chem. 2000, 1467-1482) or it can be obtained by chemoenzymatic routes as described in WO07056191. The GSC structure is shown below:

GSC

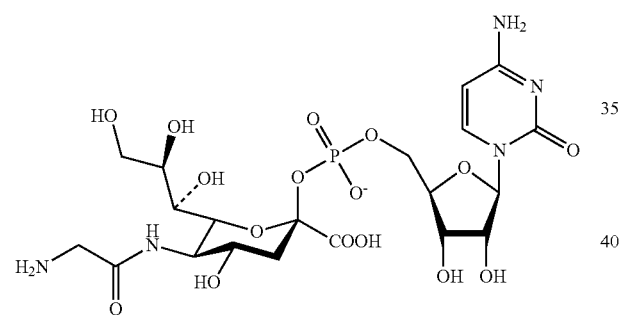

Example 9

Preparation of 38.8k-HEP-[N]-FVIIa L288F T293K

Step 1: Synthesis of [(4-mercaptobutanoyl)glycyl]sialic acid cytidine monophosphate (GSC-SH)

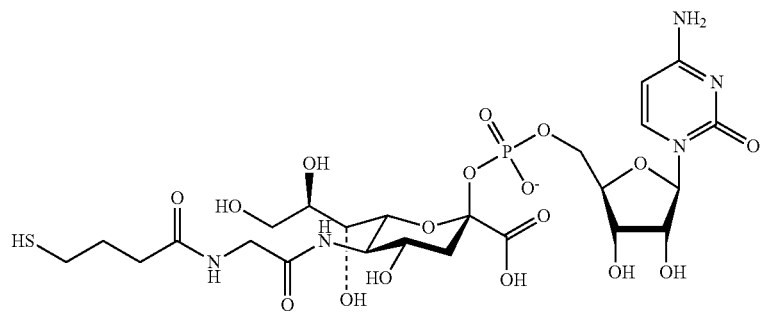

Glycyl sialic acid cytidine monophosphate (200 mg; 0.318 mmol) was dissolved in water (2 ml), and thiobutyrolactone (325 mg; 3.18 mmol) was added. The two phase solution was gently mixed for 21 h at room temperature. The reaction mixture was then diluted with water (10 ml) and applied to a reverse phase HPLC column (C18, 50 mm×200 mm). Column was eluted at a flow rate of 50 ml/min with a gradient system of water (A), acetonitrile (B) and 250 mM ammonium hydrogen carbonate (C) as follows: 0 min (A: 90%, B: 0%, C:10%); 12 min (A: 90%, B: 0%, C:10%); 48 min (A: 70%, B: 20%, C:10%). Fractions (20 ml size) were collected and analysed by LC-MS. Pure fractions were pooled, and passed slowly through a short pad of Dowex 50 W×2 (100-200 mesh) resin in sodium form, before lyophilized into dry powder. Content of title material in freeze dried powder was then determined by HPLC using absorbance at 260 nm, and glycyl sialic acid cytidine monophosphate as reference material. For the HPLC analysis, a Waters X-Bridge phenyl column (5 μm 4.6 mm×250 mm) and a water acetonitrile system (linear gradient from 0-85% acetonitrile over 30 min containing 0.1% phosphoric acid) was used. Yield: 61.6 mg (26%). LCMS: 732.18 (MH$^+$); 427.14 (MH$^+$-CMP). Compound was stable for extended periods (>12 months) when stored at −80° C.

Step 2: Synthesis of 38.8 kDa HEP-GSC Reagent with Succinimide Linkage

The HEP-GSC reagent was prepared by coupling GSC-SH ([(4-mercaptobutanoyl)glycyl]sialic acid cytidine monophosphate) from step 1 with HEP-maleimide in a 1:1 molar ratio as follows: GSC-SH (0.68 mg) dissolved in 50 mM Hepes, 100 mM NaCl, pH 7.0 (50 μl) was added 35 mg of the 38.8k-HEP-maleimide dissolved in 50 mM Hepes, 100 mM NaCl, pH 7.0 (1.35 ml). The clear solution was left for 2 hours at 25° C. Unreacted GSC-SH was removed by dialysis using a Slide-A-Lyzer cassette (Thermo Scientific) with a cut-off of 10 kD. The dialysis buffer was 50 mM Hepes, 100 mM NaCl, 10 mM CaCl$_2$, pH 7.0. The reaction mixture was dialyzed twice for 2.5 hours. The recovered material was used as such in step 4 below, assuming a quantitative reaction between GSC-SH and HEP-maleimide. The HEP-GSC reagent made by this procedure will contain a HEP polymer attached to sialic acid cytidine monophosphate via a succinimide linkage.

Step 3: Desialylation of FVIIa L288F T293K

FVIIa L288F T293K (30 mg) was added sialidase (AUS, 100 ul, 20 U) in 10 mM His, 100 mM NaCl, 60 mM CaCl$_2$, 10 mM PABA pH 5.9 (10 ml), and left for 1 hour at room temperature. The reaction mixture was then diluted with 50 mM HEPES, 100 mM NaCl, 1 mM EDTA, pH 7.0 (30 ml), and cooled on ice. 250 mM EDTA solution (2.6 ml) was added in small portions, keeping pH at neutral by sodium hydroxide addition. The EDTA treated sample was then applied to a 2×5 ml HiTrap Q FF ion-exchange columns (Amersham Biosciences, GE Healthcare) equilibrated with 50 mM HEPES, 100 mM NaCl, 1 mM EDTA, pH 7.0. Unbound protein was eluted with 50 mM HEPES, 100 mM NaCl, 1 mM EDTA, pH 7.0 (4 CV), followed by 50 mM HEPES, 150 mM NaCl, pH 7.0 (8 CV), before eluting asialo FVIIa L288F T293K with 50 mM HEPES, 100 mM NaCl, 10 mM CaCl$_2$, pH 7.0 (20 CV). Asialo FVIIa L288F T293K was isolated in 50 mM Hepes, 150 mM NaCl, 10 mM CaCl$_2$, pH 7.0. Yield (19.15 mg) was determined by quantifying the FVIIa L288F T293K light chain content against a FVIIa standard after tris(2-carboxyethyl)phosphine reduction using reverse phase HPLC.

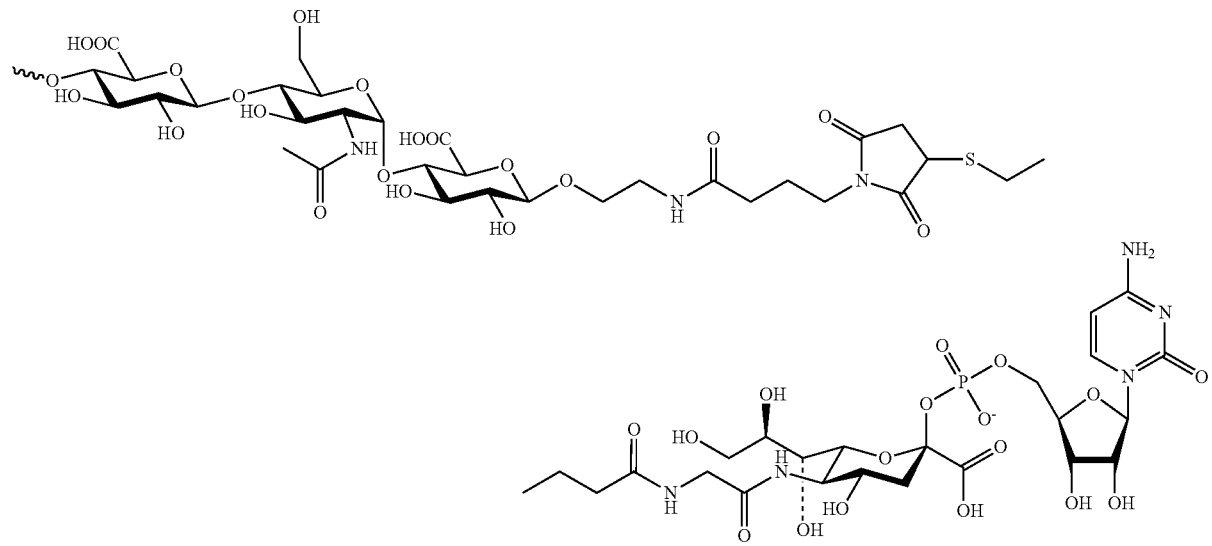

Step 4: Synthesis of 38.8 kDa HEP-[N]-FVIIa L288F T293K with Succinimide Linkage To asialo FVIIa L288F T293K (19.2 mg) in 50 mM Hepes, 100 mM NaCl, 10 mM CaCl$_2$, 10 mM PABA, pH 7.0 (18.0 ml) was added 38.8 kDa-HEP-GSC (35 mg from step 2) in 50 mM Hepes, 100 mM NaCl, 10 mM CaCl$_2$, pH 7.0 (2.3 ml), and rat ST3GalIII enzyme (5 mg; 1.1 unit/mg) in 20 mM Hepes, 120 mM NaCl, 50% glycerol, pH 7.0 (7.2 ml). The reaction mixture was incubated over night at 32° C. under slow rotation. The reaction mixture was then applied to a FVIIa specific affinity column (CV=24 ml) modified with a Gla-domain specific antibody and step eluted first with 2 column volumes of buffer A (50 mM Hepes, 100 mM NaCl, 10 mM CaCl$_2$, pH 7.4) then 2 column volumes of buffer B (50 mM Hepes, 100 mM NaCl, 10 mM EDTA, pH 7.4). The method essentially follows the principle described by Thim, L et al. Biochemistry (1988) 27, 7785-779. The product with unfolded Gla-domain was collected and directly applied to a 2×5 ml HiTrap Q FF ion-exchange columns (Amersham Biosciences, GE Healthcare). Column was washed with 10 mM His, 100 mM NaCl, 0.01% Tween80, pH 7.5 (3 column volumes), and 10 mM His, 100 mM NaCl, 10 mM CaCl$_2$, 0.01% Tween80, pH 7.5 (for 3.5 column volume). The pH was then lowered to 6.0 with 10 mM His, 100 mM NaCl, 10 mM CaCl$_2$, 0.01% Tween80, pH 6.0 (3 column volumes), and the HEPylated material eluted with 5 column volumes of a buffer mixture composed of 60% buffer A (10 mM His, 100 mM NaCl, 10 mM CaCl$_2$, 0.01% Tween80, pH 6.0) and 40% buffer B (10 mM His, 1 M NaCl, 10 mM CaCl$_2$, 0.01% Tween80, pH 6.0). The recovered asialo FVIIa L288F T293K (Thermo Scientific) with a cut-off of 10 kD. The dialysis buffer was 10 mM His, 100 mM NaCl, 10 mM CaCl$_2$, 0.01% Tween80, pH 6.0. The protein concentration was determined by light-chain HPLC analysis after TCEP reduction. The overall yield of 38.8k-HEP-[N]-FVIIa L288F T293K was 2.46 mg (13%).

Example 10

Preparation of 41.5 kDa-HEP-[N]-FVIIa L288F T293K K337A

Step 1: Synthesis of 41.5 kDa HEP-GSC reagent with 4-methylbenzoyl linkage

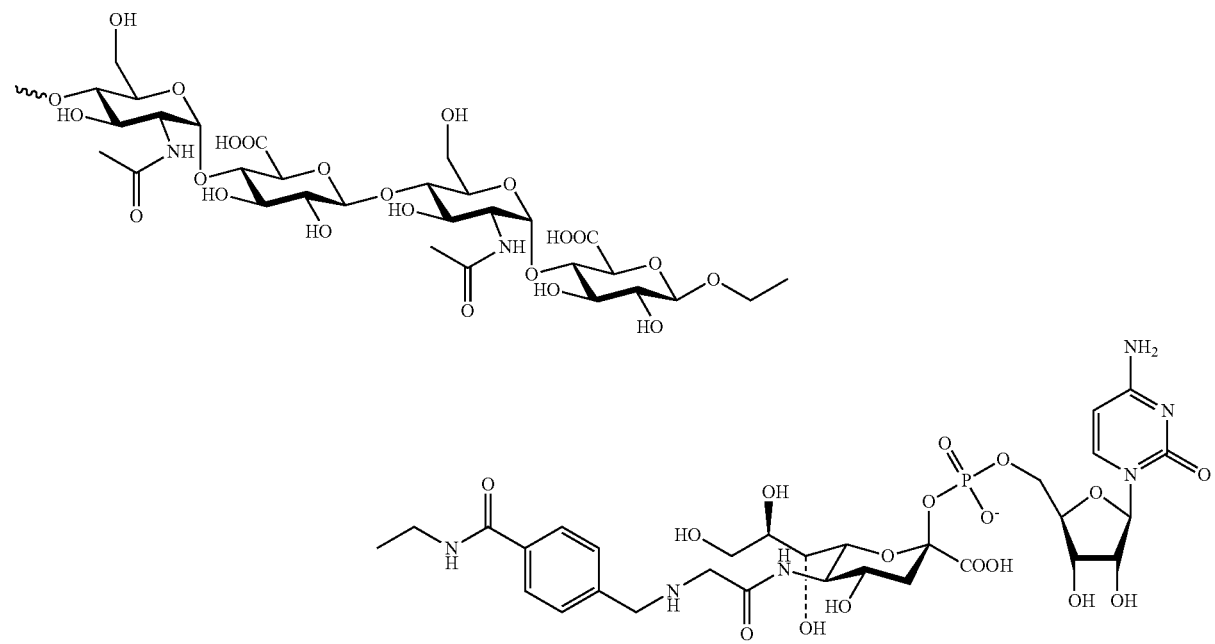

(unmodified) was recycled, ie. was HEPylated once more as described in step 4 and purified in the same way as just described. The combined fractions from two hepylation runs were pooled and concentrated by ultrafiltration (Millipore Amicon Ultra, cut off 10 kD).

Step 5: Capping of Mono Glycoconjugated Heparosan 38.8k-HEP-[N]-FVIIa L288F T293K Non-sialylated N-glycanes of 38.8k-HEP-[N]-FVIIa L288F T293K were finally capped (i.e. sialylated) with ST3GalIII enzyme and CMP-NAN as follows: 38.8k-HEP-[N]-FVIIa L288F T293K (5.85 mg) was incubated with ST3GalIII (0.18 mg/ml); CMP-NAN (4.98 mM) in 8.4 ml of 10 mM His, 100 mM NaCl, 10 mM CaCl$_2$, 0.01% Tween80, pH 6.0 for 1 h at 32° C. The reaction mixture was then applied to a FVIIa specific affinity column modified with a Gla-domain specific antibody and step eluted first with 2 column volumes of buffer A (50 mM Hepes, 100 mM NaCl, 10 mM CaCl$_2$, pH 7.4) then 2 column volumes of buffer B (50 mM Hepes, 100 mM NaCl, 10 mM EDTA, pH 7.4). The pooled fractions containing 38.8k-HEP-[N]-FVIIa L288F T293K were combined and dialyzed using a Slide-A-Lyzer cassette Glycyl sialic acid cytidine monophosphate (GSC) (20 mg; 32 μmol) in 5.0 ml 50 mM Hepes, 100 mM NaCl, 10 mM CaCl$_2$ buffer, pH 7.0 was added 41.5 kDa HEP-benzaldehyde (99.7 mg; 2.5 μmol). The mixture was gently rotated until all HEP-benzaldehyde had dissolved. During the following 2 hours, a 1M solution of sodium cyanoborohydride in MilliQ water was added in portions (5×50 μl), to reach a final concentration of 48 mM. Reaction mixture was left at room temperature overnight. Excess of GSC was then removed by dialysis as follows: the total reaction volume (5250 μl) was transferred to a dialysis cassette (Slide-A-Lyzer Dialysis Cassette, Thermo Scientific Prod No. 66810 with cut-off 10 kDa capacity: 3-12 ml). Solution was dialysed for 2 hours against 2000 ml of 25 mM Hepes buffer (pH 7.2) and once more for 17 h against 2000 ml of 25 mM Hepes buffer (pH 7.2). Complete removal of excess GSC from inner chamber was verified by HPLC on Waters X-Bridge phenyl column (4.6 mm×250 mm, 5 μm) and a water acetonitrile system (linear gradient from 0-85% acetonitrile over 30 min containing 0.1% phosphoric acid) using GSC as reference. Inner chamber material was collected and freeze dried to give 41.5 kDa HEP-GSC as white powder. The HEP-GSC reagent was analysed by NMR and on SEC chromatography. The HEP- GSC reagent made by this procedure contains a HEP polymer attached to sialic acid cytidine monophosphate via a 4-methylbenzoyl linkage.

Step 2: Desialylation of FVIIa L288F T293K K337A

To a solution of FVIIa L288F T293K K337A (43.5 mg) in 21 ml of 10 mM His, 100 mM NaCl, 60 mM CaCl$_2$, 10 mM PABA, pH 6.7 buffer was added sialidase (*Arthrobacter ureafaciens*, 9 units/ml). The reaction mixture was incubated for 1 hour at room temperature. The reaction mixture was then cooled on ice and added 14 ml of 10 mM His, 100 mM NaCl pH 7.7. 50 ml of a 100 mM EDTA solution was then added while maintaining neutral pH. The reaction mixture was then diluted with 50 ml of MilliQ water, and applied to 4×5 ml interconnected HiTrap Q FF ion-exchange columns (Amersham Biosciences, GE Healthcare) equilibrated in 50 mM HEPES, 50 mM NaCl, pH 7.0. Unbound protein including sialidase was eluted with 5 CV of 50 mM HEPES, 150 mM NaCl, pH 7.0. Desialylated protein was eluted with 12 CV of 50 mM HEPES, 150 mM NaCl, 30 mM CaCl2, pH 7.0. Fractions containing protein were combined and added 0.5M PABA to reach a final concentration of 10 mM. Protein yield was determined by quantifying the FVIIa L288F T293K K337A light chain against a FVIIa standard after tris(2-carboxyethyl)phosphine reduction using reverse phase HPLC as described above. 32.5 mg asialo FVIIa L288F T293K K337A (2.83 mg/ml) was in this way isolated in 11.5 ml of 50 mM Hepes, 150 mM NaCl, 30 mM CaCl$_2$, 10 mM PABA, pH 7.0.

To asialo FVIIa L288F T293K K337A (16.3 mg) in 5.75 ml of 50 mM Hepes, 150 mM NaCl, 30 mM CaCl$_2$, 10 mM PABA, pH 7.0 was added 41.5 kDa HEP-GSC (3 equivalents, 41.5 mg) and rat ST3GalIII enzyme (2.93 mg; 1.1 unit/mg) in 4.2 ml of 20 mM Hepes, 120 mM NaCl, 50% glycerol, pH 7.0. PABA concentration was then adjusted to 10 mM with a 0.5M aqueous PABA solution, and pH was adjusted to 6.7 with 1N NaOH. The reaction mixture was incubated overnight at 32° C. under slow stirring. A solution 157 mM CMP-NAN in 50 mM Hepes, 150 mM NaCl, 10 mM CaCl2, pH 7.0 (356 μl) was then added, and the reaction was incubated at 32° C. for an additional hour. HPLC analysis showed a product distribution containing un-reacted FVIIa L288F T293K K337A (68%), mono HEPylated FVIIa (25%) and various poly-HEPylated forms (7%).

The entire reaction mixture was then applied to a FVIIa specific affinity column (CV=24 ml) modified with a Gla-domain specific antibody and step eluted first with 2 column volumes of buffer A (50 mM Hepes, 100 mM NaCl, 10 mM CaCl$_2$, pH 7.4) then 2 column volumes of buffer B (50 mM Hepes, 100 mM NaCl, 10 mM EDTA, pH 7.4). The method essentially follows the principle described by Thim, L et al. Biochemistry (1988) 27, 7785-779.

The products with unfolded Gla-domain was collected and directly applied to 3×5 ml interconnected HiTrap Q FF ion-exchange columns (Amersham Biosciences, GE Healthcare) equilibrated with a buffer containing 10 mM His, 100 mM NaCl, pH 6.0. The column was washed with 4 column volumes of 10 mM His, 100 mM NaCl, pH 6.0. Unmodified FVIIa L288F T293K K337A was eluted with 12 CV of 10 mM His, 100 mM NaCl, 10 mM CaCl$_2$, pH 6.0 (elution buffer A). 41.5 kDa-HEP-[N]-FVIIa L288F T293K K337A was then eluted with 15 CV of 10 mM His, 325 mM NaCl, 10 mM CaCl$_2$, pH 6.0. Pure fractions were combined, and protein concentration was determined by HPLC quantification method previously described. 3.42 mg (21%) pure 41.5 kDa-HEP-[N]-FVIIa L288F T293K K337A was isolated.

The combined fractions containing 41.5 kDa-HEP-[N]-FVIIa L288F T293K K337A was finally dialyzed against 10 mM His, 100 mM NaCl, 10 mM CaCl$_2$, pH 6.0 using a Slide-A-Lyzer cassette (Thermo Scientific) with a cut-off of 10 kD, and concentration adjusted to (0.40 mg/ml) by adding dialysis buffer.

Example 11

Preparation of 41.5 kDa HEP-[N]-FVIIa W201 T293K

This material was prepared essentially as described in example 10. FVIIa W201R T293K (40 mg) was initially desialylated and asialo FVIIa W201R T293K (27.2 mg) was isolated by the Gla-specific ion-exchange method. The desialylated analogue was then incubated with 41.5 kDa HEP-GSC (produced as described in example 10) and ST3GalIII. The conjugation product was then isolated by ion-exchange chromatography. Final buffer exchange afforded 2.9 mg (7.5%) of 41.5 kDa HEP-[N]-FVIIa W201 T293K in 10 mM His, 100 mM NaCl, 10 mM CaCl$_2$, pH 6.0.

Example 12

Preparation of 41.5 kDa HEP-[N]-FVIIa L288Y T293K

This material was prepared essentially as described in example 10. FVIIa L288Y T293K (19.9 mg) was initially desialylated and asialo FVIIa L288Y T293K (16.9 mg) was isolated by the Gla-specific ion-exchange method. The desialylated analogue was then incubated with 41.5 kDa HEP-GSC (produced as described in example 10) and ST3GalIII. The conjugation product was then isolated by ion-exchange chromatography. Final buffer exchange afforded 1.95 mg (11.5%) of 41.5 kDa HEP-[N]-FVIIa L288Y T293K in 10 mM His, 100 mM NaCl, 10 mM CaCl$_2$, pH 6.0.

Example 13

Preparation of 41.5 kDa HEP-[N]-FVIIa L288Y T293R

This material was prepared essentially as described in example 10. After desialylation asialo FVIIa L288Y T293R (30 mg) was reacted with 41.5 kDa HEP-GSC (produced as described in example 10) and ST3GalIII. The conjugation product was then isolated by ion-exchange chromatography. Final buffer exchange afforded 4.33 mg (14.4%) of 41.5 kDa HEP-[N]-FVIIa L288Y T293R was obtained in 10 mM His, 100 mM NaCl, 10 mM CaCl$_2$, pH 6.0.

Example 14

Preparation of 41.5 kDa HEP-[N]-FVIIa T293K K337A

This material was prepared essentially as described in example 10. After desialylation asialo FVIIa L288Y T293R (8 mg) was reacted with 41.5 kDa HEP-GSC (produced as described in example 10) and ST3GalIII. The conjugation product was isolated by ion-exchange chromatography. Final buffer exchange afforded 1.72 mg (15%) of 41.5 kDa HEP-[N]-FVIIa T293K K337A in 10 mM His, 100 mM NaCl, 10 mM CaCl$_2$, pH 6.0.

Example 15

Functional Properties of Modified Combination FVIIa Variants

FVIIa combination variants glycoconjugated to either PEG or heparosan (HEP), as described in examples 9-14, were characterized for proteolytic activity and antithrombin reactivity as described in example 5. Results are summarized in Table 7. These data show that chemical modifications of FVIIa, in the cases with PEG or HEP, decreases FVIIa variant proteolytic activity but for some variants allows to retain higher than wild-type FVIIa proteolytic activity and further allows to retain antithrombin resistance.

TABLE 7

Functional properties of modified FVIIa variants.
Results are shown in percent (%) of wild-type FVIIa.

| IUPAC name | Proteolytic activity + PS:PC (% WT) | Proteolytic activity + sTF + PS:PC (% WT) | ATIII Inhibition + LMWH (% WT) | ATIII Inhibition + sTF (% WT) |
|---|---|---|---|---|
| 40k-PEG-[N]-FVIIa W201R T293Y | 266.9 | 88.8 | 5.9 | 1.9 |
| 40k-HEP-[N]-FVIIa W201R T293K | 155.3 | 236.7 | 0.2 | 1.2 |
| 40k-HEP-[N]-FVIIa L288Y T293R | 407 | 200.3 | 5.2 | 4.4 |
| 40k-HEP-[N]-FVIIa L288Y T293K | 264.9 | 147.4 | 3.7 | 2.9 |
| 40k-HEP-[N]-FVIIa L288F T293K K337A | 555.5 | 115 | | |
| 40K-HEP-[N]-FVIIa L288F T293K | 279.3 | 116.4 | 4.4 | 3.6 |

Example 16

Evaluation in Haemophilia A-Like Whole Blood Thrombelastography

Thrombelastography (TEG) assay was chosen to evaluate activity of FVIIa variants in a heamophilia A-like whole blood by comparison to FVIIa. TEG assay provides a profile of the entire coagulation process—initiation, propagation and final clot strength measurements. Apart from the possible influence of shear forces in flowing blood and the vasculature, TEG assay mimics the in vivo conditions of coagulation as the method measures the visco elastic properties of clotting whole blood (Viuff, E. et al, Thrombosis Research, (2010), Vol. 126, pages 144-149). Each TEG assay was initiated by using kaolin and TEG parameters clotting time (R) and maximum thrombus generation rate (MTG) were recorded and reported in Table 8. The clotting time (R) denotes the latency time from placing blood in the sample cup until the clot starts to form (2 mm amplitude); whereas, the maximum thrombus generation (MTG) denotes the velocity of clot formation. The clotting time (R) in seconds is determined using standard TEG software; whereas, MTG is calculated as the first derivative of the TEG track multiplied with 100 (100× mm/second).

Blood samples were obtained from normal, healthy donors who were members of the Danish National Corps of Voluntary Blood Donors and met the criteria for blood donation. Blood was sampled in 3.2% citrate vacutainers (Vacuette ref. 455322, Greiner bio-one, Lot A020601 2007-02) and assayed within 60 minutes. Haemophilia A-like blood was prepared from normal human whole blood by addition of anti-human FVIII (Sheep anti-human FVIII, Lot AA11-01, Haematologic Technologies, VT, USA) antibody to a final concentration of 10 Bethesda Units (BU) per ml (final 0.1 mg/ml) and rotated gently at 2 rpm/min for 30 min at room temperature. The test compounds were added at 0.1, 1, 10 and 25 nM final concentrations besides FVIIa L288Y T293K that was tested in 0.069, 0.69, 6.9, 17.3 nM and FVIIa W201R T293K that was tested in 0.076, 0.76, 7.6, 19.1 nM.

Data from the kaolin-induced TEG showed that all compounds dose-dependently decreased clotting time (R-time) and increases maximum thrombus generation (MTG) in haemophilia A-like blood (Table 8). All 40k-HEP-[N]-FVIIa-variants showed shorter or similar clot time compared with FVIIa when evaluated in the highest test concentration. Also maximum thrombus generation of the variants was as similar or increased relative to FVIIa. Moreover, the data showed that 40k-HEPylation of FVIIa variants reduced the activity of the 40k-HEPylated compounds when compared to their corresponding FVIIa variants (with no 40k-EPylation).

Table 8 shows the R-time (clot time) and MTG (maximum thrombus generation) of test compounds in kaolin-induced TEG in Haemophila A-like whole blood. The highest concentration of test compound was 25 nM besides FVIIa L288Y T293K that was tested in 17.3 nM and FVIIa W201R T293K that was tested in 19.1 nM. FVIIa, 40k-PEG-[N]-FVIIa and 40k-HEP-[N]-FVIIa was tested in four individual donors (n=4) whereas the remaining compounds were tested in two individual donors (n=2). Data in square brackets indicate the range for the parameter from the four individual donors.

TABLE 8

Thromboelastography parameters for selected FVIIa variants in Haemophilia A-like whole blood.

| Test compound (at highest concentration) | R-time mean (sec) | MTG (×100 mm/sec) |
|---|---|---|
| FVIIa | 526 | 21.6 |
| | [480; 580] | [19.4; 26.1] |
| 40k-PEG-[N]-FVIIa | 753 | 17.9 |
| | [680; 835] | [16.1; 19.9] |
| 40k-HEP-[N]-FVIIa | 668 | 19.0 |
| | [580; 835] | [15.8; 22.4] |
| FVIIa L288Y T293K | 345 | 24.5 |
| | [320; 370] | [24.1; 24.8] |
| 40k-HEP-[N]-FVIIa L288Y T293K | 485 | 21.5 |
| | [465; 505] | [20.3; 22.7] |
| FVIIa L288Y T293R | 313 | 25.5 |
| | [305; 320] | [24.3; 26.8] |
| 40k-HEP-[N]-FVIIa L288Y T293R | 398 | 23.4 |
| | [370; 425] | [23.1; 23.7] |
| FVIIa L288F T293K | 400 | 25.9 |
| | [375; 425] | [23.3; 28.5] |
| 40k-HEP-[N]-FVIIa L288F T293K | 498 | 21.6 |
| | [425; 570] | [19.0; 24.1] |
| FVIIa L288F T293K K337A | 280 | 27.2 |
| | [255; 305] | [26.9; 27.6] |
| 40k-HEP-[N]-FVIIa L288F T293K K337A | 348 | 25.7 |
| | [335; 360] | [23.4; 28.0] |
| FVIIa W201R T293K | 390 | 25.2 |
| | [335; 445] | [22.4; 28.1] |
| 40k-HEP-[N]-FVIIa W201R T293K | 345 | 25.7 |
| | [295; 395] | [23.7; 27; 7] |
| FVIIa T293K K337A | 355 | 25.5 |
| | [350-360] | [24.3; 26.6] |
| 40k-HEP-[N]-FVIIa T293K K337A | 423 | 22.2 |
| | [420; 425] | [21.7; 22.8] |

Example 17

Assessment of PK in Rat

A pharmacokinetic analysis of identified FVIIa variants in an unmodified form or glycoconjugated with either PEG or heparosan (HEP) was performed in rats to assess their effect on the in vivo survival of FVIIa. Sprague Dawley rats (three per group) were dosed intravenously. Stabylite™ (TriniLize Stabylite Tubes; Tcoag Ireland Ltd, Ireland) stabilized plasma samples were collected as full profiles at appropriate time points and frozen until further analysis. Plasma samples were analysed for clot activity (as described in Example 7) and by an ELISA quantifying FVIIa-antithrombin complexes. Pharmacokinetic analysis was carried out by non-compartmental methods using Phoenix WinNonlin 6.0 (Pharsight Corporation). The following parameters were estimated: Cmax (maximum concentration) of FVIIa-antithrombin complex, T1/2 (the functional terminal half-life) and MRT (the functional mean residence time) for clot activity.

Briefly, FVIIa—antithrombin complexes were measured by use of an enzyme immunoassay (EIA). A monoclonal anti-FVIIa antibody that binds to the N-terminal of the EGF-domain and does not block antithrombin binding is used for capture of the complex (Dako Denmark A/S, Glostrup; product code O9572). A polyclonal anti-human AT antibody peroxidase conjugate was used for detection (Siemens Healthcare Diagnostics ApS, Ballerup/Denmark; product code OWMG15). A preformed purified complex of human wild-type or variant FVIIa and plasma-derived human antithrombin was used as standard to construct EIA calibration curves. Plasma samples were diluted and analysed and mean concentration of duplicate measurements calculated. The intra—assay precision of the EIA was between 1-8%.

Pharmacokinetic estimated parameters are listed in Table 9. Relative to wild-type FVIIa, the tested variants exhibited reduced accumulation of FVIIa-antithrombin complexes (Rat AT complex) with plasma levels approaching the detection level. Furthermore, a significantly prolonged functional half-life of 40k-HEP-[N]-FVIIa L288F T293K (18.4 hrs in rat) was observed compared to 40k-PEG-[N]-FVIIa (7.4 hrs in rat).

In conclusion, the presence of Lys at position 293 increases the T1/2 in rat and reduces the FVIIa-antithrombin complex formation. Furthermore, introduction of glycoconjugated heparason substantially improves the T1/2 in rat.

TABLE 9

Pharmacokinetic estimated parameters for selected FVIIa variants in rat.

| FVIIa variant | T½ in rat (hrs) | MRT in rat (hrs) | Rat AT complex Cmax/dose (kg/l) |
|---|---|---|---|
| FVIIa | 0.8 ± 0.01 | 1.1 ± 0.03 | 0.6 ± 0.08 |
| 40k-PEG-[N]-FVIIa | 7.4 ± 0.20 | 8.3 ± 0.30 | 0.7 ± 0.05 |
| 40k-HEP-[N]-FVIIa L288Y T293K | 15.9 ± 0.5 | 20.6 ± 1.0 | 0.04 ± 0.004 |
| 40k-HEP-[N]-FVIIa L288Y T293R | 11.5 ± 0.5 | 13.9 ± 0.6 | 0.05 ± 0.004 |
| FVIIa L288F T293K | 1.2 ± 0.02 | 1.6 ± 0.30 | 0.07 ± 0.01 |
| 40k-HEP-[N]-FVIIa L288F T293K | 18.4 ± 3.4 | 20.5 ± .6 | 0.04 ± 0.000 |
| 40k-HEP-[N]-FVIIa W201 R T293K | 21.1 ± 0.5 | 24.8 ± 0.8 | Not measured |
| 40k-HEP-[N]-FVIIa L288F T293K K337A | 11.0 ± 1.6 | 11.5 ± 0.8 | 0.14 ± 0.01 |
| 40k-HEP-[N]-FVIIa T293K K337A | 12.4 ± 0.1 | 15.4 ± 0.3 | 0.05 ± 0.004 |

T½: Terminal half-life of the active molecule following IV administration
MRT: Mean residence time of the active molecule following IV administration.
AT complex Cmax/dose: Maximum measured level of compound-antithrombin complex divided by the dose.

Example 18

Liquid Formulation of FVIIa L288Y T293K Through Active Site Stabilization

The stability of FVIIa in solution is limited by a number of modifications to the polypeptide chain occurring as a result of autoproteolysis, oxidation, deamidation, isomerization, etc. Previous studies have identified three sites on the heavy chain that are susceptible to autoproteolytic attack; these are Arg290-Gly291, Arg315-Lys316, and Lys316-Val317 (Nicolaisen et al., FEBS, 1993, 317:245-249). Calcium-free conditions further promote proteolytic release of the first 38 residues of the light chain encompassing the γ-carboxyglutamic acid (Gla) domain.

Here we have used the small molecule, PCI-27483-S(2-{2-[5-(6-Carbamimidoyl-1H-benzoimidazol-2-yl)-6,2'-dihydroxy-5-sulfamoyl-biphenyl-3-yl]-acetylamino}-succinic acid), which stabilize the active site of FVIIa through non-covalent interactions and to prevent autoproteolysis of the heavy chain in a liquid formulation (See WO2014/057069 for further details on PCI-27483-S).

Quantification of heavy chain cleavage has been assessed by analysis of reduced FVIIa L288Y T293K with reversed phase HPLC (RP-HPLC). The assay solution was reduced in 127 mM dithiothreitol (DTT) and 3M guanidinium hydrochloride, which were incubated for 60° C. in 15 min, followed by the addition of 1 μL concentrated acetic acid (per 50 μL of original assay solution) and cooling to 25° C. 25 μg reduced FVIIa L288Y T293K were then injected on a ACE 3 μM C4 column (300 Å, 4.6×100 mm; Advanced Chromatography Technologies LTD, Scotland) which were temperature equilibrated at 40° C. The protein fragments were separated with a linear gradient having a mobile phase A consisting of 0.05% trifluoroacetic acid (TFA) in water and going from 35-80% of mobile phase B consisting of 0.045% TFA in 80% acetonitrile. The gradient time was 30 min with a flow rate of 0.7 mL/min and peak elution were detected with absorbance at 215 nm.

The formulation of FVIIa L288Y T293K were made up by 1.47 mg/mL CaCl$_2$, 7.5 mg/mL NaCl, 1.55 mg/mL L-Histidine, 1.32 mg/mL Glycylglycine, 0.5 mg/mL L-Methionine, 0.07 mg/mL Polysorbate 80, 0.021 mg/ml PCI-27483-S, a protein concentration of 1 mg/ml (i.e. a protein inhibitor mole ratio of 1:1.75) and a final pH of 6.8. The solution was incubated for 1 month at 30° C. under quiescent conditions and away from light. As seen in Table 10 the presence of PCI-27483-S, led to near-complete inhibition of heavy chain cleavage of FVIIa L288Y T293K; whereas, no addition of PCI-27483-S led to a prominent increase in the cleavage at the positions 315-316 and 290-291.

TABLE 10

Percentage increase of the peak areas relative to day zero of heavy chain fragments corresponding to two different cleavage sites as determined in the RP-HPLC chromatograms upon 28 days of incubation with and without PCI-27483-S inhibitor.

| Cleavage site | With PCI-27483-S | Without PCI-27483-S |
|---|---|---|
| 315-316 | 20% | 287% |
| 290-291 | 17% | 675% |

Example 19

In Silico Assessment of Immunogenicity Risk

The in-silico study investigated whether the novel peptides sequences that results from protein engineering to generate FVIIa analogues could result in peptide sequences capable of binding to major histocompatibility complex class II (MHC-II), also known as HLA-II in humans. Such binding is prerequisite for the presence of T-cell epitopes. The peptide/HLA-II binding prediction software used in this study was based on two algorithms, NetMHCIIpan 2.1 (Nielsen et al. 2010), performing HLA-DR predictions, and NetMHCII 2.2 (Nielsen et al. 2009) performing HLA-DP/DQ predictions.

An Immunogenicity Risk Score (IRS) was calculated in order to be able to compare the different FVIIa analogues with regard to immunogenicity risk potential. The calculation was performed as follows: FVIIa wild-type was used as reference and only predicted 15mers not in the reference (FVIIa wild-type) which had a predicted Rank of 10 or less were included in the analysis. The HLA-II alleles were classified into three classes: Class 1 (Rank<=1) with weight of 2. Class 2 (1>Rank<=3) with weight of 0.5 and Class 3 (3>Rank<=10) with weight of 0.2. The class weight (2. 0.5 or 0.2) was multiplied by the allele frequency (for each population) to give the IRS. The sum of IRS was calculated for each population and each HLA-II (DRB1, DP and DQ).

The calculated risk scores for select single and combination variants are given in Table 11. Particularly favourable combinations include L288F/T293K, L288F/T293K/K337A, L288Y/T293K and L288Y/T293K/K337A which at the same time exhibit a high proteolytic activity as well as reduced susceptibility to inhibition by antithrombin.

TABLE 11

Calculated risk scores for select single and combination FVIIa variants.

| FVIIa variant | Risk score |
|---|---|
| FVIIa L288F T293K | 0.10 |
| FVIIa L288F T293K K337A | 0.10 |
| FVIIa L288F T293K L305I | 0.40 |
| FVIIa L288F T293K L305V | 0.35 |
| FVIIa L288F T293R | 0.12 |
| FVIIa L288F T293R K337A | 0.12 |
| FVIIa L288F T293R L305I | 0.42 |
| FVIIa L288F T293R L305V | 0.37 |
| FVIIa L288F T293Y | 0.32 |
| FVIIa L288F T293Y K337A | 0.32 |
| FVIIa L288N T293K | 0.06 |
| FVIIa L288N T293R | 0.08 |
| FVIIa L288N T293Y | 0.26 |
| FVIIa L288Y T293K | 0.06 |
| FVIIa L288Y T293K K337A | 0.06 |
| FVIIa L288Y T293R | 0.09 |
| FVIIa L288Y T293R K337A | 0.09 |
| FVIIa L305V T293K | 0.28 |
| FVIIa L305V T293Y | 0.49 |
| FVIIa T293K K337A | 0.02 |
| FVIIa T293K L305I | 0.32 |
| FVIIa T293K L305V K337A | 0.28 |
| FVIIa T293R K337A | 0.06 |
| FVIIa T293R L305I | 0.36 |
| FVIIa T293R L305V | 0.32 |
| FVIIa T293R L305V K337A | 0.32 |
| FVIIa T293Y K337A | 0.23 |
| FVIIa T293Y L305V K337A | 0.49 |
| FVIIa W201K T293K | 0.19 |
| FVIIa W201K T293R | 0.23 |
| FVIIa W201K T293Y | 0.39 |
| FVIIa W201M T293K | 1.03 |
| FVIIa W201M T293R | 1.06 |
| FVIIa W201M T293Y | 1.23 |
| FVIIa W201R L288F T293K | 0.32 |
| FVIIa W201R L288F T293R | 0.34 |
| FVIIa W201R T293K | 0.25 |
| FVIIa W201R T293K L305I | 0.55 |
| FVIIa W201R T293R | 0.29 |
| FVIIa W201R T293R L305I | 0.58 |
| FVIIa W201R T293Y | 0.45 |

The invention claimed is:

1. A conjugate comprising a structure conjugated to an N-glycan on a Factor VII (FVII variant, wherein said FVII variant comprises L288Y and T293K substitutions relative to the amino acid sequence of SEQ ID NO: 1, wherein the structure comprises and wherein n is an integer from 95-115.

2. The conjugate of claim 1, wherein said FVII variant is a FVIIa variant.

3. A pharmaceutical composition comprising the conjugate of claim 1 and a pharmaceutically acceptable carrier.

4. A method of treating a coagulopathy in a subject in need thereof, comprising administering to said subject a therapeutically effective amount of the pharmaceutical composition of claim 3.

5. The method of claim 4, wherein said coagulopathy is haemophilia A, haemophilia B, haemophilia A with acquired inhibitors, or haemophilia B with acquired inhibitors.

6. The conjugate of claim 1, wherein the amino acid sequence of said FVII variant consists of SEQ ID NO: 1 modified by L288Y and T293K substitutions.

7. The conjugate of claim 6, wherein said FVII variant is a FVIIa variant.

8. A pharmaceutical composition comprising the conjugate of claim 6 and a pharmaceutically acceptable carrier.

9. A method of treating a coagulopathy in a subject in need thereof,
    comprising administering to said subject a therapeutically effective amount of the pharmaceutical composition of claim 8.

10. The method of claim 9, wherein said coagulopathy is haemophilia A, haemophilia B, haemophilia A with acquired inhibitors, or haemophilia B with acquired inhibitors.

\* \* \* \* \*

SEQUENCE LISTING

```
<160> NUMBER OF SEQ ID NOS: 9

<210> SEQ ID NO 1
<211> LENGTH: 406
<212> TYPE: PRT
<213> ORGANISM: Homo sapiens

<400> SEQUENCE: 1

Ala Asn Ala Phe Leu Glu Glu Leu Arg Pro Gly Ser Leu Glu Arg Glu
1               5                   10                  15

Cys Lys Glu Glu Gln Cys Ser Phe Glu Glu Ala Arg Glu Ile Phe Lys
            20                  25                  30

Asp Ala Glu Arg Thr Lys Leu Phe Trp Ile Ser Tyr Ser Asp Gly Asp
        35                  40                  45

Gln Cys Ala Ser Ser Pro Cys Gln Asn Gly Gly Ser Cys Lys Asp Gln
    50                  55                  60
```

Leu Gln Ser Tyr Ile Cys Phe Cys Leu Pro Ala Phe Glu Gly Arg Asn
65                  70                  75                  80

Cys Glu Thr His Lys Asp Asp Gln Leu Ile Cys Val Asn Glu Asn Gly
            85                  90                  95

Gly Cys Glu Gln Tyr Cys Ser Asp His Thr Gly Thr Lys Arg Ser Cys
        100                 105                 110

Arg Cys His Glu Gly Tyr Ser Leu Leu Ala Asp Gly Val Ser Cys Thr
    115                 120                 125

Pro Thr Val Glu Tyr Pro Cys Gly Lys Ile Pro Ile Leu Glu Lys Arg
130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405

<210> SEQ ID NO 2
<211> LENGTH: 254
<212> TYPE: PRT
<213> ORGANISM: Homo sapiens

<400> SEQUENCE: 2

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn

```
                    20                  25                  30
Thr Ile Trp Val Val Ser Ala Ala His Cys Phe Asp Lys Ile Lys Asn
            35                  40                  45

Trp Arg Asn Leu Ile Ala Val Leu Gly Glu His Asp Leu Ser Glu His
        50                  55                  60

Asp Gly Asp Glu Gln Ser Arg Arg Val Ala Gln Val Ile Ile Pro Ser
65                  70                  75                  80

Thr Tyr Val Pro Gly Thr Thr Asn His Asp Ile Ala Leu Leu Arg Leu
                85                  90                  95

His Gln Pro Val Val Leu Thr Asp His Val Val Pro Leu Cys Leu Pro
            100                 105                 110

Glu Arg Thr Phe Ser Glu Arg Thr Leu Ala Phe Val Arg Phe Ser Leu
        115                 120                 125

Val Ser Gly Trp Gly Gln Leu Leu Asp Arg Gly Ala Thr Ala Leu Glu
    130                 135                 140

Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
            180                 185                 190

Gly Gly Pro His Ala Thr His Tyr Arg Gly Thr Trp Tyr Leu Thr Gly
        195                 200                 205

Ile Val Ser Trp Gly Gln Gly Cys Ala Thr Val Gly His Phe Gly Val
    210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250

<210> SEQ ID NO 3
<211> LENGTH: 254
<212> TYPE: PRT
<213> ORGANISM: Unknown
<220> FEATURE:
<223> OTHER INFORMATION: Chimpanzee

<400> SEQUENCE: 3

Ile Val Gly Gly Lys Val Cys Pro Lys Gly Glu Cys Pro Trp Gln Val
1               5                   10                  15

Leu Leu Leu Val Asn Gly Ala Gln Leu Cys Gly Gly Thr Leu Ile Asn
            20                  25                  30

Thr Ile Trp Val Val Ser Ala Ala His Cys Phe Asp Lys Ile Lys Asn
        35                  40                  45

Trp Arg Asn Leu Ile Ala Val Leu Gly Glu His Asp Leu Ser Glu His
    50                  55                  60

Asp Gly Asp Glu Gln Ser Arg Arg Val Ala Gln Val Ile Ile Pro Ser
65                  70                  75                  80

Thr Tyr Ile Pro Gly Thr Thr Asn His Asp Ile Ala Leu Leu Arg Leu
                85                  90                  95

His Gln Pro Val Val Leu Thr Asp His Val Val Pro Leu Cys Leu Pro
            100                 105                 110

Glu Arg Ala Phe Ser Glu Arg Thr Leu Ala Phe Val Arg Phe Ser Leu
        115                 120                 125

Val Ser Gly Trp Gly Gln Leu Leu Asp Arg Gly Ala Thr Ala Leu Glu
```

```
                130                 135                 140
Leu Met Val Leu Asn Val Pro Arg Leu Met Thr Gln Asp Cys Leu Gln
145                 150                 155                 160

Gln Ser Arg Lys Val Gly Asp Ser Pro Asn Ile Thr Glu Tyr Met Phe
                165                 170                 175

Cys Ala Gly Tyr Ser Asp Gly Ser Lys Asp Ser Cys Lys Gly Asp Ser
                180                 185                 190

Gly Gly Pro His Ala Thr His Tyr Arg Gly Thr Trp Tyr Leu Thr Gly
                195                 200                 205

Ile Val Ser Trp Gly Gln Gly Cys Ala Ser Val Gly His Phe Gly Val
                210                 215                 220

Tyr Thr Arg Val Ser Gln Tyr Ile Glu Trp Leu Gln Lys Leu Met Arg
225                 230                 235                 240

Ser Glu Pro Arg Pro Gly Val Leu Leu Arg Ala Pro Phe Pro
                245                 250

<210> SEQ ID NO 4
<211> LENGTH: 254
<212> TYPE: PRT
<213> ORGANISM: Unknown
<220> FEATURE:
<223> OTHER INFORMATION: Dog

<400> SEQUENCE: 4

Ile Val Gly Gly Lys Val Cys Pro Lys Gly Glu Cys Pro Trp Gln Ala
1               5                   10                  15

Ala Val Lys Val Asp Gly Lys Leu Leu Cys Gly Gly Thr Leu Ile Asp
                20                  25                  30

Ala Ala Trp Val Val Ser Ala Ala His Cys Phe Glu Arg Ile Lys Asn
                35                  40                  45

Trp Lys Asn Leu Thr Val Val Leu Gly Glu His Asp Leu Ser Glu Asp
            50                  55                  60

Asp Gly Asp Glu Gln Glu Arg His Val Ala Arg Val Ile Val Pro Asp
65                  70                  75                  80

Lys Tyr Ile Pro Leu Lys Thr Asn His Asp Ile Ala Leu Leu His Leu
                85                  90                  95

Arg Thr Pro Val Ala Tyr Thr Asp His Val Val Pro Leu Cys Leu Pro
                100                 105                 110

Glu Lys Thr Phe Ser Glu Arg Thr Leu Ala Phe Ile Arg Phe Ser Ala
                115                 120                 125

Val Ser Gly Trp Gly Arg Leu Leu Asp Arg Gly Ala Lys Ala Arg Val
                130                 135                 140

Leu Met Ala Ile Gln Val Pro Arg Leu Met Thr Gln Asp Cys Leu Glu
145                 150                 155                 160

Gln Ala Arg Arg Arg Pro Gly Ser Pro Ser Ile Thr Asp Asn Met Phe
                165                 170                 175

Cys Ala Gly Tyr Leu Asp Gly Ser Lys Asp Ala Cys Gln Gly Asp Ser
                180                 185                 190

Gly Gly Pro His Ala Thr Lys Phe Gln Gly Thr Trp Tyr Leu Thr Gly
                195                 200                 205

Val Val Ser Trp Gly Glu Gly Cys Ala Ala Glu Gly His Phe Gly Val
                210                 215                 220

Tyr Thr Arg Val Ser Gln Tyr Ile Glu Trp Leu Arg Gln Leu Met Val
225                 230                 235                 240

Ser Ser His Thr Leu Arg Gly Leu Leu Arg Ala Pro Leu Pro
```

```
                        245                 250

<210> SEQ ID NO 5
<211> LENGTH: 255
<212> TYPE: PRT
<213> ORGANISM: Unknown
<220> FEATURE:
<223> OTHER INFORMATION: Porcine

<400> SEQUENCE: 5

Ile Val Gly Gly Lys Val Cys Pro Lys Gly Glu Cys Pro Trp Gln Ala
1               5                   10                  15

Met Leu Lys Leu Lys Gly Ala Leu Leu Cys Gly Gly Thr Leu Leu Asn
            20                  25                  30

Thr Ser Trp Val Val Ser Ala Ala His Cys Phe Asp Arg Ile Arg Ser
        35                  40                  45

Trp Lys Asp Leu Thr Val Val Leu Gly Glu His Asp Leu Ser Lys Asp
    50                  55                  60

Glu Gly Asp Glu Gln Arg Pro Val Ala Gln Val Phe Val Pro Asp
65                  70                  75                  80

Lys Tyr Val Pro Gly Lys Thr Asp His Asp Leu Ala Leu Val Arg Leu
                85                  90                  95

Ala Arg Pro Val Ala Leu Thr Asp His Val Val Pro Leu Cys Leu Pro
            100                 105                 110

Glu Arg Ser Phe Ser Glu Arg Thr Leu Ala Phe Ile Arg Phe Ser Ala
        115                 120                 125

Val Ser Gly Trp Gly Arg Leu Leu Asp Arg Gly Ala Lys Ala Arg Val
    130                 135                 140

Leu Met Ala Ile Gln Val Pro Arg Leu Met Thr Gln Asp Cys Leu Glu
145                 150                 155                 160

Gln Ala Arg Arg Arg Pro Gly Ser Pro Ser Ile Thr Asp Asn Met Phe
                165                 170                 175

Cys Ala Gly Tyr Leu Asp Gly Ser Lys Asp Ala Cys Lys Gly Asp Ser
            180                 185                 190

Gly Gly Pro His Ala Thr Arg Phe Arg Gly Thr Trp Phe Leu Thr Gly
        195                 200                 205

Val Val Ser Trp Gly Glu Gly Cys Ala Ala Thr Gly Arg Phe Gly Val
    210                 215                 220

Tyr Thr Arg Val Ser Arg Tyr Thr Ala Trp Leu Leu Gly Leu Met Ser
225                 230                 235                 240

Ala Pro Pro Pro Pro Ser Glu Gly Leu Leu Arg Ala Pro Leu Pro
                245                 250                 255

<210> SEQ ID NO 6
<211> LENGTH: 255
<212> TYPE: PRT
<213> ORGANISM: Unknown
<220> FEATURE:
<223> OTHER INFORMATION: Bovine

<400> SEQUENCE: 6

Ile Val Gly Gly His Val Cys Pro Lys Gly Glu Cys Pro Trp Gln Ala
1               5                   10                  15

Met Leu Lys Leu Asn Gly Ala Leu Leu Cys Gly Gly Thr Leu Val Gly
            20                  25                  30

Pro Ala Trp Val Val Ser Ala Ala His Cys Phe Glu Arg Leu Arg Ser
        35                  40                  45
```

```
Arg Gly Asn Leu Thr Ala Val Leu Gly Glu His Asp Leu Ser Arg Val
 50                  55                  60

Glu Gly Pro Glu Gln Glu Arg Val Ala Gln Ile Ile Val Pro Lys
 65                  70                  75                  80

Gln Tyr Val Pro Gly Gln Thr Asp His Asp Val Ala Leu Leu Gln Leu
                 85                  90                  95

Ala Gln Pro Val Ala Leu Gly Asp His Val Ala Pro Leu Cys Leu Pro
             100                 105                 110

Asp Pro Asp Phe Ala Asp Gln Thr Leu Ala Phe Val Arg Phe Ser Ala
             115                 120                 125

Val Ser Gly Trp Gly Gln Leu Leu Glu Arg Gly Val Thr Ala Arg Lys
130                 135                 140

Leu Met Val Val Leu Val Pro Arg Leu Leu Thr Gln Asp Cys Leu Gln
145                 150                 155                 160

Gln Ser Arg Gln Arg Pro Gly Gly Pro Val Val Thr Asp Asn Met Phe
                165                 170                 175

Cys Ala Gly Tyr Ser Asp Gly Ser Lys Asp Ala Cys Lys Gly Asp Ser
            180                 185                 190

Gly Gly Pro His Ala Thr Arg Phe Arg Gly Thr Trp Phe Leu Thr Gly
            195                 200                 205

Val Val Ser Trp Gly Glu Gly Cys Ala Ala Gly His Phe Gly Ile
210                 215                 220

Tyr Thr Arg Val Ser Arg Tyr Thr Ala Trp Leu Arg Gln Leu Met Gly
225                 230                 235                 240

His Pro Pro Ser Arg Gln Gly Phe Phe Gln Val Pro Leu Leu Pro
                245                 250                 255

<210> SEQ ID NO 7
<211> LENGTH: 253
<212> TYPE: PRT
<213> ORGANISM: Mus musculus

<400> SEQUENCE: 7

Ile Val Gly Gly Asn Val Cys Pro Lys Gly Glu Cys Pro Trp Gln Ala
 1               5                  10                  15

Val Leu Lys Ile Asn Gly Leu Leu Leu Cys Gly Ala Val Leu Leu Asp
                 20                  25                  30

Ala Arg Trp Ile Val Thr Ala Ala His Cys Phe Asp Asn Ile Arg Tyr
             35                  40                  45

Trp Gly Asn Ile Thr Val Val Met Gly Glu His Asp Phe Ser Glu Lys
 50                  55                  60

Asp Gly Asp Glu Gln Val Arg Arg Val Thr Gln Val Ile Met Pro Asp
 65                  70                  75                  80

Lys Tyr Ile Arg Gly Lys Ile Asn His Asp Ile Ala Leu Leu Arg Leu
                 85                  90                  95

His Arg Pro Val Thr Phe Thr Asp Tyr Val Val Pro Leu Cys Leu Pro
             100                 105                 110

Glu Lys Ser Phe Ser Glu Asn Thr Leu Ala Arg Ile Arg Phe Ser Arg
             115                 120                 125

Val Ser Gly Trp Gly Gln Leu Leu Asp Arg Gly Ala Thr Ala Leu Glu
130                 135                 140

Leu Met Ser Ile Glu Val Pro Arg Leu Met Thr Gln Asp Cys Leu Glu
145                 150                 155                 160

His Ala Lys His Ser Ser Asn Thr Pro Lys Ile Thr Glu Asn Met Phe
                165                 170                 175
```

```
Cys Ala Gly Tyr Met Asp Gly Thr Lys Asp Ala Cys Lys Gly Asp Ser
            180                 185                 190

Gly Gly Pro His Ala Thr His Tyr His Gly Thr Trp Tyr Leu Thr Gly
            195                 200                 205

Val Val Ser Trp Gly Glu Gly Cys Ala Ala Ile Gly His Ile Gly Val
            210                 215                 220

Tyr Thr Arg Val Ser Gln Tyr Ile Asp Trp Leu Val Arg His Met Asp
225                 230                 235                 240

Ser Lys Leu Gln Val Gly Val Phe Arg Leu Pro Leu Leu
                245                 250

<210> SEQ ID NO 8
<211> LENGTH: 253
<212> TYPE: PRT
<213> ORGANISM: Unknown
<220> FEATURE:
<223> OTHER INFORMATION: Rat

<400> SEQUENCE: 8

Ile Val Gly Gly Tyr Val Cys Pro Lys Gly Glu Cys Pro Trp Gln Ala
1               5                   10                  15

Val Leu Lys Phe Asn Glu Ala Leu Leu Cys Gly Ala Val Leu Leu Asp
                20                  25                  30

Thr Arg Trp Ile Val Thr Ala Ala His Cys Phe Asp Lys Phe Gly Lys
            35                  40                  45

Leu Val Asn Ile Thr Val Leu Gly Glu His Asp Phe Ser Glu Lys
        50                  55                  60

Glu Gly Thr Glu Gln Val Arg Leu Val Glu Gln Val Ile Met Pro Asn
65                  70                  75                  80

Lys Tyr Thr Arg Gly Arg Thr Asp His Asp Ile Ala Leu Val Arg Leu
                85                  90                  95

His Arg Pro Val Thr Phe Thr Asp Tyr Val Val Pro Leu Cys Leu Pro
            100                 105                 110

Glu Arg Ala Phe Ser Glu Asn Thr Leu Ala Ser Ile Arg Phe Ser Arg
        115                 120                 125

Val Ser Gly Trp Gly Gln Leu Leu Asp Arg Gly Ala Thr Ala Leu Glu
130                 135                 140

Leu Met Val Ile Glu Val Pro Arg Leu Met Thr Gln Asp Cys Leu Glu
145                 150                 155                 160

His Ala Lys His Ser Ala Asn Thr Pro Arg Ile Thr Glu Asn Met Phe
                165                 170                 175

Cys Ala Gly Tyr Met Asp Gly Thr Lys Asp Ala Cys Lys Gly Asp Ser
            180                 185                 190

Gly Gly Pro His Ala Thr His Tyr His Gly Thr Trp Tyr Leu Thr Gly
            195                 200                 205

Val Val Ser Trp Gly Glu Gly Cys Ala Ala Ile Gly His Ile Gly Val
            210                 215                 220

Tyr Thr Arg Val Ser Gln Tyr Ile Asp Trp Leu Val Lys Tyr Met Asp
225                 230                 235                 240

Ser Lys Leu Arg Val Gly Ile Ser Arg Val Ser Leu Leu
                245                 250

<210> SEQ ID NO 9
<211> LENGTH: 253
<212> TYPE: PRT
<213> ORGANISM: Unknown
```

```
<220> FEATURE:
<223> OTHER INFORMATION: Rabbit

<400> SEQUENCE: 9

Ile Val Gly Gly Lys Val Cys Pro Lys Gly Glu Cys Pro Trp Gln Ala
1               5                   10                  15

Ala Leu Met Asn Gly Ser Thr Leu Leu Cys Gly Gly Ser Leu Leu Asp
            20                  25                  30

Thr His Trp Val Val Ser Ala Ala His Cys Phe Asp Lys Leu Ser Ser
        35                  40                  45

Leu Arg Asn Leu Thr Ile Val Leu Gly Glu His Asp Leu Ser Glu His
    50                  55                  60

Glu Gly Asp Glu Gln Val Arg His Val Ala Gln Leu Ile Met Pro Asp
65                  70                  75                  80

Lys Tyr Val Pro Gly Lys Thr Asp His Asp Ile Ala Leu Leu Arg Leu
                85                  90                  95

Leu Gln Pro Ala Ala Leu Thr Asn Asn Val Val Pro Leu Cys Leu Pro
            100                 105                 110

Glu Arg Asn Phe Ser Glu Ser Thr Leu Ala Thr Ile Arg Phe Ser Arg
            115                 120                 125

Val Ser Gly Trp Gly Gln Leu Leu Tyr Arg Gly Ala Leu Ala Arg Glu
        130                 135                 140

Leu Met Ala Ile Asp Val Pro Arg Leu Met Thr Gln Asp Cys Val Glu
145                 150                 155                 160

Gln Ser Glu His Lys Pro Gly Ser Pro Glu Val Thr Gly Asn Met Phe
                165                 170                 175

Cys Ala Gly Tyr Leu Asp Gly Ser Lys Asp Ala Cys Lys Gly Asp Ser
            180                 185                 190

Gly Gly Pro His Ala Thr Ser Tyr His Gly Thr Trp Tyr Leu Thr Gly
        195                 200                 205

Val Val Ser Trp Gly Glu Gly Cys Ala Ala Val Gly His Val Gly Val
    210                 215                 220

Tyr Thr Arg Val Ser Arg Tyr Thr Glu Trp Leu Ser Arg Leu Met Arg
225                 230                 235                 240

Ser Lys Leu His His Gly Ile Gln Arg His Pro Phe Pro
                245                 250
```